United States Patent
Armstrong et al.

(10) Patent No.: US 6,703,347 B2
(45) Date of Patent: Mar. 9, 2004

(54) ISOTHIAZOLE DERIVATIVES AND THEIR USE AS PESTICIDES

(75) Inventors: Sarah Armstrong, Berkshire (GB); Nigel John Barnes, Berkshire (GB); Susan Patricia Barnett, Berkshire (GB); Eric Daniel Clarke, Berkshire (GB); Patrick Jelf Crowley, Berkshire (GB); Torquil Eoghan Macleod Fraser, Berkshire (GB); David John Hughes, Berkshire (GB); Christopher John Mathews, Berkshire (GB); Roger Salmon, Berkshire (GB); Stephen Christopher Smith, Berkshire (GB); Russell Viner, Berkshire (GB); William Guy Whittingham, Berkshire (GB); John Williams, Berkshire (GB); Alan John Whittle, Berkshire (GB); William Roderick Mound, Berkshire (GB); Christopher John Urch, Berkshire (GB); Brian Leslie Pilkington, deceased, late of Berkshire (GB), by Joan Pilkington, executor

(73) Assignee: Syngenta Limited (GB)

( * ) Notice: Subject to any disclaimer, the term of this patent is extended or adjusted under 35 U.S.C. 154(b) by 36 days.

(21) Appl. No.: 10/182,425

(22) PCT Filed: Jan. 26, 2001

(86) PCT No.: PCT/GB01/00338

§ 371 (c)(1),
(2), (4) Date: Nov. 7, 2002

(87) PCT Pub. No.: WO01/55144

PCT Pub. Date: Aug. 2, 2001

(65) Prior Publication Data

US 2003/0207926 A1 Nov. 6, 2003

(30) Foreign Application Priority Data

Jan. 28, 2000 (GB) .................................. 0002037

(51) Int. Cl.$^7$ ..................... C07D 417/12; C07D 417/14; H01N 43/80

(52) U.S. Cl. ..................... 504/225; 504/269; 514/233.8; 514/367; 514/372; 544/133; 548/180; 548/206; 548/214; 548/212

(58) Field of Search ................................. 548/206, 180, 548/212; 514/367, 372; 504/269

(56) References Cited

U.S. PATENT DOCUMENTS

| 5,972,843 | A | 10/1999 | Heil et al. |
| 6,008,366 | A | 12/1999 | Heil et al. |
| 6,544,989 | B2 | * 4/2003 | Mathews et al. ........ 514/233.8 |

FOREIGN PATENT DOCUMENTS

| WO | WO 95 31448 | 11/1995 |
| WO | WO 98 02424 | 1/1998 |
| WO | WO 00 06566 | 2/2000 |
| WO | 2001055139 | * 8/2001 |
| WO | 2001055141 | * 8/2001 |
| WO | 2001055142 | * 8/2001 |
| WO | 2001055143 | * 8/2001 |

* cited by examiner

*Primary Examiner*—Joseph K. McKane
*Assistant Examiner*—Andrea D. Small
(74) *Attorney, Agent, or Firm*—Rose M. Allen

(57) ABSTRACT

A compound of formula (I), where A is optionally substituted alkylene, alkenylene, alkynylene, cycloalkylene, alkylenoxy, oxy($C_{1-6}$)alkylene, alkylenthio, thio($C_{1-6}$)alkylene, $C_{1-6}$alkylenamino, amino($C_{1-6}$)alkylene, [$C_{1-6}$alkyleneoxy($C_{1-6}$)alkylene], [$C_{1-6}$alkylenethio($C_{1-6}$)alkylene], [$_{1-6}$alkylenesulfinyl($C_{1-6}$)alkylene], [$C_{1-6}$alkylenesulfonyl($C_{1-6}$)alkylene] or [$C_{1-6}$alkyleneamino($C_{1-6}$)alkylene]; provided that A is not $CH_2$ or $CH_2O$; B is N,N-oxide or $CR^8$; Y is O, S or $NR^9$; Z is O, S or $NR^{10}$; and $R^1, R^2, R^3, R^4, R^5, R^6, R^7, R^8, R^9, R^{10}$ are specified radicals; compositions containing them; process for making them; and their use as insecticides or fungicides.

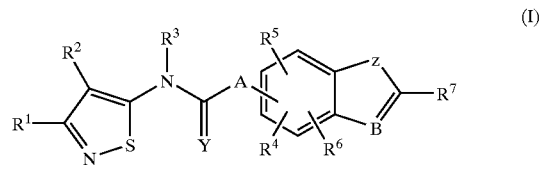

(I)

12 Claims, No Drawings

ISOTHIAZOLE DERIVATIVES AND THEIR USE AS PESTICIDES

This application is a 371 of PCT/GB01/00338 Jan. 26, 2001.

The present invention relates to azole derivatives, to processes for preparing them, to fungicidal, insecticidal, acaricidal, molluscicidal and nematicidal compositions comprising them, to methods of using them to combat fungal diseases (especially fungal diseases of plants) and to methods of using them to combat and control insect, acarine, mollusc and nematode pests.

Azole and azine derivatives are disclosed in WO95/31448, WO97/18198, WO98/02424, WO98/05670 and WO98/17630.

The present invention provides a compound of formula (I):

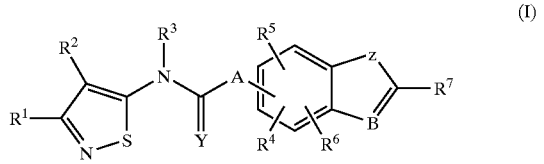

where A is optionally substituted $C_{1-6}$ alkylene, optionally substituted $C_{2-6}$ alkenylene, optionally substituted $C_{2-6}$ alkynylene, optionally substituted cycloalkylene, optionally substituted $C_{1-6}$ alkylenoxy, optionally substituted oxy($C_{1-6}$) alkylene, optionally substituted $C_{1-6}$ alkylenethio, optionally substituted thio($C_{1-6}$)alkylene, optionally substituted $C_{1-6}$ alkylenamino, optionally substituted amino($C_{1-6}$)alkylene, optionally substituted [$C_{1-6}$ alkyleneoxy($C_{1-6}$)alkylene], optionally substituted [$C_{1-6}$ alkylenethio($C_{1-6}$)alkylene], optionally substituted [$C_{1-6}$ alkylenesulfinyl($C_{1-6}$)alkylene], optionally substituted [$C_{1-6}$ alkylenesulfonyl($C_{1-6}$)alkylene] or optionally substituted [$C_{1-6}$ alkyleneamino($C_{1-6}$) alkylene]; provided that A is not $CH_2$ or $CH_2O$; B is N,N-oxide or $CR^8$; Y is O, S or $NR^9$; Z is O, S or $NR^{10}$; $R^1$ is hydrogen, halogen, optionally substituted $C_{1-6}$ alkyl, optionally substituted $C_{2-6}$ alkenyl, optionally substituted $C_{2-6}$ alkynyl, optionally substituted $C_{1-6}$ alkoxy, optionally substituted $C_{1-6}$ alkylthio, optionally substituted $C_{3-7}$ cycloalkyl, cyano, nitro or $SF_5$; $R^2$ is hydrogen, halogen, optionally substituted $C_{1-6}$ alkyl, optionally substituted $C_{2-6}$ alkenyl, optionally substituted $C_{1-6}$ alkynyl, optionally substituted $C_{1-6}$ alkoxy, optionally substituted $C_{1-6}$ alkylthio, optionally substituted $C_{1-6}$ alkylsulfinyl, optionally substituted $C_{1-6}$ alkylsulfonyl, cyano, nitro, formyl, optionally substituted $C_{1-6}$ alkylcarbonyl, optionally substituted $C_{1-6}$ alkoxycarbonyl, $SF_5$ or $R^{11}ON=C(R^{12})$; or $R^1$ and $R^2$ together with the atoms to which they are attached may be joined to form a five, six or seven-membered saturated or unsaturated, carbocyclic or heterocyclic ring which may contain one or two heteroatoms selected from O, N or S and which is optionally substituted by $C_{1-6}$ alkyl, $C_{1-6}$ haloalkyl or halogen; $R^3$ is hydrogen, optionally substituted $C_{1-10}$ alkyl, optionally substituted [$C_{2-6}$ alkenyl($C_{1-6}$)alkyl], optionally substituted [$C_{2-6}$ alkynyl($C_{1-6}$)alkyl], optionally substituted $C_{3-7}$ cycloalkyl, optionally substituted $C_{1-10}$ alkylcarbonyl, optionally substituted $C_{1-10}$ alkoxycarbonyl, formyl, optionally substituted $C_{1-10}$ alkylaminocarbonyl, optionally substituted di($C_{1-10}$)alkylaminocarbonyl, optionally substituted phenoxycarbonyl, optionally substituted $C_{1-6}$ alkylthio, optionally substituted $C_{1-6}$ alkylsulfinyl, optionally substituted $C_{1-6}$ alkylsulfonyl, optionally substituted $C_{1-6}$ arylthio, optionally substituted $C_{1-6}$ arylsulfinyl, optionally substituted $C_{1-6}$ arylsulfonyl or $R^{13}R^{14}NS(O)_p$; p is 0, 1 or 2; $R^4$, $R^5$ and $R^6$ are, independently, hydrogen, halogen, optionally substituted $C_{1-6}$ alkyl, optionally substituted $C_{1-6}$ alkoxy, optionally substituted $C_{1-6}$ alkylthio, optionally substituted $C_{1-6}$ alkylsulfinyl, optionally substituted $C_{1-6}$ alkylsulfonyl, cyano, nitro, optionally substituted $C_{1-6}$ alkylcarbonyl, optionally substituted $C_{1-6}$ alkoxycarbonyl or $SF_5$; $R^7$ is hydrogen, halogen, cyano, optionally substituted $C_{1-20}$ alkyl, optionally substituted $C_{2-20}$ alkenyl, optionally substituted $C_{2-20}$ alkynyl, optionally substituted $C_{3-7}$ cycloalkyl, optionally substituted $C_{5-6}$ cycloalkenyl, formyl, optionally substituted $C_{1-20}$ alkoxycarbonyl, optionally substituted $C_{1-20}$ alkylcarbonyl, aminocarbonyl, optionally substituted $C_{1-20}$ alkylaminocarbonyl, optionally substituted di($C_{1-20}$)alkylaminocarbonyl, optionally substituted aryloxycarbonyl, optionally substituted arylcarbonyl, optionally substituted arylaminocarbonyl optionally substituted N—($C_{1-6}$)alkyl-N-arylaminocarbonyl, optionally substituted diarylaminocarbonyl, optionally substituted heteroaryloxycarbonyl, optionally substituted heteroarylcarbonyl, optionally substituted heteroarylaminocarbonyl, optionally substituted N—($C_{1-6}$) alkyl-N-heteroarylaminocarbonyl, optionally substituted diheteroarylaminocarbonyl, optionally substituted phenyl, optionally substituted heteroaryl, optionally substituted heterocyclyl, SH, optionally substituted $C_{1-20}$ alkylthio, optionally substituted $C_{1-20}$ alkylsulfinyl, optionally substituted $C_{1-20}$ alkylsulfonyl, optionally substituted arylthio, optionally substituted arylsulfinyl, optionally substituted arylsulfonyl, $R^{15}O$, $R^{16}R^{17}N$ or $R^{18}ON=C(R^{19})$; $R^8$ is hydrogen, halogen, nitro, cyano, optionally substituted $C_{1-8}$ alkyl, optionally substituted $C_{2-6}$ alkenyl, optionally substituted $C_{2-6}$ alkynyl, optionally substituted $C_{3-7}$ cycloalkyl, optionally substituted $C_{1-6}$ alkoxycarbonyl, optionally substituted $C_{1-6}$ alkylcarbonyl, optionally substituted $C_{1-6}$ alkylaminocarbonyl, optionally substituted di($C_{1-6}$) alkylaminocarbonyl, optionally substituted phenyl or optionally substituted heteroaryl; $R^9$ is hydrogen, cyano, nitro, optionally substituted $C_{1-6}$ alkyl, optionally substituted $C_{3-7}$ cycloalkyl, optionally substituted ($C_{2-4}$)alkenyl ($C_{1-6}$)alkyl, optionally substituted ($C_{2-6}$)alkynyl($C_{1-6}$)alkyl, optionally substituted phenyl, optionally substituted heteroaryl, optionally substituted $C_{1-6}$ alkylcarbonyl, optionally substituted $C_{1-6}$ alkoxycarbonyl, optionally substituted $C_{1-6}$ alkylamino, optionally substituted di($C_{1-6}$) alkylamino, optionally substituted $C_{1-6}$ alkylcarbonylamino, optionally substituted $C_{1-6}$ alkoxycarbonylamino, optionally substituted $C_{1-6}$ alkoxy, optionally substituted $C_{1-6}$ alkylthio, optionally substituted $C_{1-6}$ alkylsulfinyl, optionally substituted $C_{1-6}$ alkylsulfonyl, optionally substituted arylthio, optionally substituted arylsulfinyl, optionally substituted arylsulfonyl or $C_{1-6}$ alkylcarbonyloxy; $R^{10}$ is hydrogen, cyano, optionally substituted $C_{1-8}$ alkyl, optionally substituted [$C_{2-6}$ alkenyl($C_{1-6}$)alkyl], optionally substituted [$C_{2-6}$ alkyl($C_{1-6}$)alkyl], optionally substituted $C_{3-7}$ cycloalkyl, optionally substituted [$C_{3-7}$ cycloalkyl($C_{1-6}$) alkyl], $C_{1-6}$ alkoxy($C_{1-6}$)alkyl, optionally substituted $C_{1-6}$ alkoxycarbonyl, optionally substituted $C_{1-6}$ alkylcarbonyl, optionally substituted $C_{1-6}$ alkylaminocarbonyl, optionally substituted di($C_{1-6}$)alkylaminocarbonyl, optionally substituted phenyl, optionally substituted heteroaryl, optionally substituted alkylsulfonyl or optionally substituted arylsulfonyl; $R^{11}$ and $R^{18}$ are, independently, hydrogen, optionally substituted phenyl ($C_{1-2}$)alkyl or optionally substituted $C_{1-20}$ alkyl; $R^{12}$ and $R^{19}$ are, independently, hydrogen, optionally substituted phenyl or optionally substituted $C_{1-6}$ alkyl; $R^{13}$ and $R^{14}$ are, independently, optionally substituted $C_{1-6}$ alkyl;

or $R^{13}$ and $R^{14}$ together with the N atom to which they are attached form a five, six or seven-membered heterocyclic ring which may contain one or two further heteroatoms selected from O, N and S and which is optionally substituted by one or two independently selected $C_{1-6}$ alkyl groups; $R^{15}$ is hydrogen, optionally substituted $C_{1-20}$ alkyl, optionally substituted [$C_{2-20}$ alkenyl($C_{1-6}$)alkyl], optionally substituted [$C_{2-20}$ alkynyl($C_{1-6}$)alkyl], optionally substituted $C_{3-7}$ cycloalkyl, optionally substituted aryl, optionally substituted heteroaryl, optionally substituted heterocyclyl, ($C_{1-6}$)alkylCH=N, optionally substituted arylCH=N, optionally substituted [aryl($C_{1-6}$)alkyl]CH=N, optionally substituted heteroarylCH=N, optionally substituted [heterocyclyl($C_{1-6}$)alkyl]CH=N, optionally substituted arylC(CH$_3$)=N, optionally substituted heteroarylC(CH$_3$)=N or optionally substituted di($C_{1-6}$)alcylC=N; and $R^{16}$ and $R^{17}$ are, independently, hydrogen, optionally substituted $C_{1-20}$ alkyl, optionally substituted $C_{3-7}$ cycloalkyl, optionally substituted [$C_{2-20}$ alkenyl($C_{1-6}$)alkyl], optionally substituted [$C_{2-20}$ alkynyl($C_{1-6}$)alkyl], optionally substituted $C_{1-20}$ alkoxycarbonyl, optionally substituted phenoxycarbonyl, formyl, optionally substituted $C_{1-20}$ alkylcarbonyl, optionally substituted $C_{1-20}$ alkylsulfonyl or optionally substituted phenylsulfonyl.

One group of preferred compounds of formula (I) is a group wherein A is optionally substituted $C_{1-6}$ alkylene, optionally substituted $C_{2-6}$ alkenylene, optionally substituted $C_{2-6}$ alkynylene, optionally substituted $C_{1-6}$ alkylenoxy, optionally substituted oxy($C_{1-6}$)alkylene, optionally substituted $C_{1-6}$ alkylenethio, optionally substituted thio($C_{1-6}$)alkylene, optionally substituted $C_{1-6}$ alkylenamino, optionally substituted amino-($C_{1-6}$)alkylene, optionally substituted [$C_{1-6}$ alkyleneoxy($C_{1-6}$)aklylene], optionally substituted [$C_{1-6}$ alkylenethio($C_{1-6}$)alkylene], optionally substituted [$C_{1-6}$ alkylenesulfinyl($C_{1-6}$)alkylene], optionally substituted [$C_{1-6}$ alkylenesulfonyl($C_{1-6}$)alkylene] or optionally substituted [$C_{1-6}$ alkyleneamino($C_{1-6}$) alkylene], provided that A is not CH$_2$ or CH$_2$O; B is N,N-oxide or CR$^8$; Y is O, S or NR$^9$; Z is O, S or NR$^{10}$; $R^3$ is hydrogen, optionally substituted $C_{1-10}$ alkyl, optionally substituted [$C_{2-6}$ alkenyl($C_{1-6}$)alkyl], optionally substituted [$C_{2-6}$ alkynyl($C_{1-6}$)alkyl], optionally substituted $C_{3-7}$ cycloalkyl, optionally substituted $C_{1-10}$ alkylcarbonyl, optionally substituted $C_{1-10}$ alkoxycarbonyl, formyl, optionally substituted $C_{1-10}$ alkylaminocarbonyl, optionally substituted di($C_{1-10}$)alkylaminocarbonyl, optionally substituted phenoxycarbonyl, optionally substituted $C_{1-6}$ alkylthio, optionally substituted $C_{1-6}$ alkylsulfinyl, optionally substituted $C_{1-6}$ alkylsulfonyl, optionally substituted $C_{1-6}$ arylthio, optionally substituted $C_{1-6}$ arylsulfinyl, optionally substituted $C_{1-6}$ arylsulfonyl or $R^{13}R^{14}$NS; $R^4$, $R^5$ and $R^6$ are, independently, hydrogen, halogen, optionally substituted $C_{1-6}$ alkyl, optionally substituted $C_{1-6}$ alkoxy, optionally substituted $C_{1-6}$ alkylthio, optionally substituted $C_{1-6}$ alkylsulfinyl, optionally substituted $C_{1-6}$ alkylsulfonyl, cyano, nitro, optionally substituted $C_{1-6}$ alkylcarbonyl, optionally substituted $C_{1-6}$ alkoxycarbonyl or SF$_5$; $R^7$ is hydrogen, halogen, cyano, optionally substituted $C_{1-20}$ alkyl, optionally substituted $C_{2-20}$ alkenyl, optionally substituted $C_{2-20}$ alkynyl, optionally substituted $C_{3-7}$ cycloalkyl, optionally substituted $C_{5-6}$ cycloalkenyl, formyl, optionally substituted $C_{1-20}$ alkoxycarbonyl, optionally substituted $C_{1-20}$ alkylcarbonyl, aminocarbonyl, optionally substituted $C_{1-20}$ alkylaminocarbonyl, optionally substituted di($C_{1-20}$)alkylaminocarbonyl, optionally substituted aryloxycarbonyl, optionally substituted arylcarbonyl, optionally substituted arylaminocarbonyl, optionally substituted N-alkyl-N-arylamimocarbonyl, optionally substituted diarylaminocarbonyl, optionally substituted heteroaryloxycarbonyl, optionally substituted heteroarylcarbonyl, optionally substituted heteroarylaminocarbonyl, optionally substituted alkylheteroarylaminocarbonyl, optionally substituted diheteroarylaminocarbonyl, optionally substituted phenyl, optionally substituted heteroaryl, optionally substituted heterocyclyl, $R^{15}$O, HS, optionally substituted $C_{1-20}$ alkylthio, optionally substituted $C_{1-20}$ alkylsulfinyl, optionally substituted $C_{1-20}$ alkylsulfonyl, optionally substituted arylthio, optionally substituted arylsulfinyl, optionally substituted arylsulfonyl, $R^{16}R^{17}$N or $R^{18}$ON=C($R^{19}$); $R^1$ is hydrogen, halogen, optionally substituted $C_{1-6}$ alkyl, optionally substituted $C_{2-6}$ alkenyl, optionally substituted $C_{2-6}$ alkynyl, optionally substituted $C_{1-6}$ alkoxy, optionally substituted $C_{1-6}$ alkylthio, optionally substituted $C_{3-7}$ cycloalkyl, cyano, nitro or SF$_5$; $R^2$ is hydrogen, halogen, optionally substituted $C_{1-6}$ alkyl, optionally substituted $C_{2-6}$ alkenyl, optionally substituted $C_{2-6}$ alkyl, optionally substituted $C_{1-6}$ alkoxy, optionally substituted $C_{1-6}$ alkylthio, optionally substituted $C_{1-6}$ alkylsulfinyl, optionally substituted $C_{1-6}$ alkylsulfonyl, cyano, nitro, formyl, $R^{11}$ON=C($R^{12}$), optionally substituted $C_{1-6}$ alkylcarbonyl, optionally substituted $C_{1-6}$ alkoxycarbonyl or SF$_5$; or $R^1$ and $R^2$ together with the atoms to which they are attached may be joined to form a five, six or seven-membered saturated or unsaturated ring carbocylic or heterocyclic ring which may contain one or two heteroatoms selected from O, N or S and which may be optionally substituted by $C_{1-6}$ alkyl, $C_{1-6}$ haloalkyl or halogen; $R^9$ is hydrogen, cyano, nitro, optionally substituted $C_{1-6}$ alkyl, optionally substituted $C_{3-7}$ cycloalkyl, optionally substituted ($C_{2-6}$)alkenyl($C_{1-6}$)alkyl, optionally substituted ($C_{2-6}$)alkynyl($C_{1-6}$)alkyl, optionally substituted phenyl, optionally substituted heteroaryl, optionally substituted $C_{1-6}$ alkylcarbonyl, optionally substituted $C_{1-6}$ alkoxycarbonyl, optionally substituted $C_{1-6}$ alkylamino, optionally substituted di($C_{1-6}$)alkylamino, optionally substituted $C_{1-6}$ alkylcarbonylamino, optionally substituted $C_{1-6}$ alkoxycarbonylamino, optionally substituted $C_{1-6}$ alkoxy, optionally substituted $C_{1-6}$ alkylthio, optionally substituted $C_{1-6}$ alkylsulfinyl, optionally substituted $C_{1-6}$ alkylsulfonyl, optionally substituted arylthio, optionally substituted arylsulfinyl, optionally substituted arylsulfonyl or $C_{1-6}$ acyloxy, $R^{10}$ is hydrogen, cyano, optionally substituted $C_{1-8}$ alkyl, optionally substituted [$C_{2-6}$ alkenyl($C_{1-6}$)alkyl], optionally substituted [$C_{2-6}$ alkynyl($C_{1-6}$)alkyl], optionally substituted $C_{3-7}$ cycloalkyl, optionally substituted [$C_{3-7}$ cycloalkyl($C_{1-6}$)alkyl], $C_{1-6}$ alkoxy($C_{1-6}$)alkyl, optionally substituted $C_{1-6}$ alkoxycarbonyl, optionally substituted $C_{1-6}$ alkylcarbonyl, optionally substituted $C_{1-6}$ alkylaminocarbonyl, optionally substituted di($C_{1-6}$)alkylaminocarbonyl, optionally substituted phenyl, optionally substituted heteroaryl, optionally substituted alkylsulfonyl or optionally substituted arylsulfonyl; $R^8$ is hydrogen, halogen, nitro, cyano, optionally substituted $C_{1-8}$ alkyl, optionally substituted $C_{2-6}$ alkenyl, optionally substituted $C_{2-6}$ alkynyl, optionally substituted $C_{1-6}$ cycloalkyl, optionally substituted $C_{1-6}$ alkoxycarbonyl, optionally substituted $C_{1-6}$ alkylcarbonyl, optionally substituted $C_{1-6}$ alkylaminocarbonyl, optionally substituted di($C_{1-6}$)alkylaminocarbonyl, optionally substituted phenyl or optionally substituted heteroaryl; $R^{13}$ and $R^{14}$ are, independently, optionally substituted CC$_{1-6}$ alkyl or $R^{13}$ and $R^{14}$ together with the N atom to which they are attached form a five, six or seven-membered heterocyclic ring which may contain one or two further heteroatoms selected from O, N or S and which may be optionally substituted by one or two $C_{1-6}$ alkyl groups; $R^{15}$ is hydrogen, optionally substituted $C_{1-20}$ alkyl, optionally substituted [$C_{2-20}$ alkenyl ($C_{1-6}$)alkyl], optionally substituted [$C_{1-20}$ alkynyl($C_{1-6}$) alkyl], optionally substituted $C_{3-7}$ cycloalkyl, optionally substituted aryl, optionally substituted heteroaryl, optionally substituted [heterocyclyl($C_{1-6}$)alkylCH=N] or di($C_{1-6}$) alkylC=N; $R^{16}$ and $R^{17}$ are, independently, hydrogen, optionally substituted $C_{1-20}$ alkyl, optionally substituted $C_{3-7}$ cycloalkyl, optionally substituted [$C_{2-20}$ alkenyl($C_{1-6}$) alkyl], optionally substituted [$C_{2-20}$ alkynyl($C_{1-6}$)alkyl], optionally substituted $C_{1-20}$ alkoxycarbonyl, optionally substituted phenoxycarbonyl, formyl, optionally substituted $C_{1-20}$ alkylcarbonyl, optionally substituted $C_{1-20}$ alkylsulfonyl or optionally substituted phenylsulfonyl; or $R^{16}$ and $R^{17}$ together with the N atom to which they are attached form a five, six or seven-membered heterocyclic ring which may contain one or two further heteroatoms selected from O, N or S and which may be optionally substituted by one or two $C_{1-6}$ alkyl groups; $R^{19}$ and $R^{12}$ are independently hydrogen, optionally substituted phenyl or optionally substituted $C_{1-6}$ alkyl; and $R^{18}$ and $R^{11}$ are, independently, hydrogen, optionally substituted phenyl ($C_{1-2}$)alkyl or optionally substituted $C_{1-20}$ alkyl.

The compounds of formula (I) may exist in different geometric or optical isomers or tautomeric forms. This invention covers all such isomers and tautomers and mixtures thereof in all proportions as well as isotopic forms such as deuterated compounds.

When present, optional substituents on alkylene, alkenylene or alkynylene moieties include (subject to valency constraints) one or more of hydroxy, halogen, $C_{1-6}$ alkyl, $C_{1-6}$ haloalkyl, $C_{1-6}$ cyanoalkyl, $C_{1-6}$ alkoxy($C_{1-6}$) alkyl, $C_{1-6}$ alkoxy, cyano, =O, =NR$^{20}$ and =CR$^{21}$R$^{22}$; and, especially, one or more of halogen, $C_{1-6}$ alkyl, $C_{1-6}$ haloalkyl, $C_{1-6}$ cyanoalkyl $C_{1-6}$ alkoxy($C_{1-6}$) alkyl, $C_{1-6}$ alkoxy, cyano, =O, =NR$^{20}$ and =CR$^{21}$R$^{22}$; wherein R$^{20}$ is $C_{1-6}$ alkyl, $C_{1-6}$ haloalkyl, OR$^{23}$ or NR$^{24}$R$^{25}$; where R$^{21}$ and R$^{22}$ are, independently, hydrogen, $C_{1-6}$ alkyl, $C_{1-6}$ alkoxy, $C_{1-6}$ haloalkyl, cyano, $C_{1-6}$ alkoxycarbonyl, $C_{1-6}$ alkylcarbonyl or NR$^{26}$R$^{27}$; R$^{23}$ is $C_{1-6}$ alkyl, $C_{1-6}$ haloalkyl or phenyl($C_{1-2}$)alkyl; R$^{24}$ and R$^{25}$ are, independently, hydrogen, $C_{1-8}$ alkyl, $C_{3-7}$ cycloalkyl, $C_{2-6}$ alkenyl($C_{1-6}$) alkyl, $C_{2-6}$ alkynyl($C_{1-6}$)alkyl, $C_{2-6}$ haloalkyl, $C_{1-6}$ alkoxy ($C_{1-6}$)alkyl, $C_{1-6}$ alkoxycarbonyl($C_{1-6}$)alkyl, carboxy($C_{1-6}$) alkyl or phenyl($C_{1-2}$)alkyl; or R$^{24}$ and R$^{25}$ together with the N atom to which they are attached form a five, six or seven-membered heterocyclic ring which may contain one or two further hetero atoms selected from O, N or S and which is optionally substituted by one or two $C_{1-6}$ alkyl groups; R$^{26}$ and R$^{27}$ are, independently, hydrogen, $C_{1-8}$ alkyl, $C_{3-7}$ cycloalkyl, $C_{2-6}$ alkenyl($C_{1-6}$)alkyl, $C_{2-6}$ alkynyl ($C_{1-6}$)alkyl, $C_{2-6}$ haloalkyl, $C_{1-6}$ alkoxy($C_{1-6}$)alkyl, $C_{1-6}$ alkoxycarbonyl($C_{1-6}$)alkyl, carboxy($C_{1-6}$)alkyl or phenyl ($C_{1-2}$)alkyl; or R$^{26}$ and R$^{27}$ together with the N atom to which they are attached form a five, six or seven-membered heterocyclic ring which may contain one or two further heteroatoms selected from O, N or S and which is optionally substituted by one or two $C_{1-6}$ alkyl groups.

Each alkyl moiety is a straight or branched chain and is, for example, methyl, ethyl, n-propyl, n-butyl, n-pentyl, n-hexyl, isopropyl, n-butyl, sec-butyl, isobutyl, tert-butyl or neopentyl.

When present, the optional substituents on an alkyl moiety include one or more of halogen, nitro, cyano, NCS—, $C_{3-7}$ cycloalkyl (itself optionally substituted with $C_{1-6}$ alkyl or halogen), $C_{5-7}$ cycloalkenyl (itself optionally substituted with $C_{1-6}$ alkyl or halogen), hydroxy, $C_{1-10}$ alkoxy, $C_{1-10}$ alkoxy($C_{1-10}$)alkoxy, tri($C_{1-4}$)alkylsilyl($C_{1-6}$)alkoxy, $C_{1-6}$ alkoxycarbonyl($C_{1-10}$)alkoxy, $C_{1-10}$ haloalkoxy, aryl($C_{1-4}$) alkoxy (where the aryl group is optionally substituted), $C_{3-7}$ cycloalkyloxy (where the cycloalkyl group is optionally substituted with $C_{1-6}$ alkyl or halogen), $C_{1-10}$ alkenyloxy, $C_{1-10}$ alkynyloxy, SH, $C_{1-10}$ alkylthio, $C_{1-10}$ haloalkylthio, aryl($C_{1-4}$)alkylthio (where the aryl group is optionally substituted), $C_{3-7}$ cycloalkylthio (where the cycloalkyl group is optionally substituted with $C_{1-6}$ alkyl or halogen), tri($C_{1-4}$)alkylsilyl($C_{1-6}$)alkylthio, arylthio (where the aryl group is optionally substituted), $C_{1-6}$ alkylsulfonyl, $C_{1-6}$ haloalkylsulfonyl, $C_{1-6}$ alkylsulfinyl, $C_{1-6}$ haloalkylsulfinyl, arylsulfonyl (where the aryl group may be further optionally substituted), tri($C_{1-4}$)alkylsilyl, aryldi($C_{1-4}$)alkylsilyl, ($C_{1-4}$) alkyldiarylsilyl, triarylsilyl, $C_{1-10}$ alkylcarbonyl, HO$_2$C, $C_{1-10}$ alkoxycarbonyl, aminocarbonyl, $C_{1-6}$ alkylaminocarbonyl, di($C_{1-6}$ alkyl)aminocarbonyl, NC—($C_{1-3}$ alkyl)-N—($C_{1-3}$ alkoxy)aminocarbonyl, $C_{1-6}$ alkylcarbonyloxy, arylcarbonyloxy (where the aryl group is optionally substituted), di($C_{1-6}$)alkylaminocarbonyloxy, aryl (itself optionally substituted), heteroaryl (itself optionally substituted), heterocyclyl (itself optionally substituted with $C_{1-6}$ alkyl or halogen), aryloxy (where the aryl group is optionally substituted), heteroaryloxy, (where the heteroaryl group is optionally substituted), heterocyclyloxy (where the heterocyclyl group is optionally substituted with $C_{1-6}$ alkyl or halogen), amino, $C_{1-6}$ alkylamino, di($C_{1-6}$)alkylamino, $C_{1-6}$ alkylcarbonylamino and N—($C_{1-6}$)alkylcarbonyl-N—($C_{1-6}$)alkylamino.

Alkenyl and alkynyl moieties can be in the form of straight or branched chains, and the alkenyl moieties, where appropriate, can be of either the (E) or (Z)-configuration. Examples are vinyl, allyl and propargyl.

When present, the optional substituents on alkenyl or alkynyl include those optional substituents given above for an alkyl moiety.

In the context of this specification acyl is optionally substituted $C_{1-6}$ alkylcarbonyl (for example acetyl), optionally substituted $C_{2-6}$ alkenylcarbonyl, optionally substituted $C_{2-6}$ alkynylcarbonyl, optionally substituted arylcarbonyl (for example benzoyl) or optionally substituted heteroarylcarbonyl.

Halogen is fluorine, chlorine, bromine or iodine.

Haloalkyl groups are alkyl groups which are substituted with one or more of the same or different halogen atoms and are, for example, CF$_3$, CF$_2$Cl, CF$_3$CH$_2$ or CHF$_2$CH$_2$.

Aryl includes naphthyl, anthracyl, fluorenyl and indenyl but is preferably phenyl.

The term heteroaryl refers to an aromatic ring containing up to 10 atoms including one or more heteroatoms (preferably one or two heteroatoms) selected from O, S and N. Examples of such rings include pyridine, pyrimidine, furan, quinoline, quinazoline, pyrazole, thiophene, thiazole, oxazole and isoxazole.

The terms heterocycle and heterocyclyl refer to a non-aromatic ring containing up to 10 atoms including one or more (preferably one or two) heteroatoms selected from O, S and N. Examples of such rings include 1,3-dioxolane, tetrahydrofuran and morpholine.

When present, the optional substituents on heterocyclyl include $C_{1-6}$ alkyl as well as those optional substituents given above for an alkyl moiety.

Cycloalkyl includes cyclopropyl, cyclopentyl and cyclohexyl.

Cycloalkenyl includes cyclopentenyl and cyclohexenyl.

When present, the optional substituents on cycloalkyl or cycloalkenyl include $C_{1-3}$ alkyl as well as those optional substituents given above for an alkyl moiety.

Carbocyclic rings include aryl, cycloalkyl and cycloalkenyl groups.

When present, the optional substituents on aryl or heteroaryl are selected, independently, from halogen, nitro, cyano, NCS—, $C_{1-6}$ alkyl, $C_{1-6}$ haloalkyl, $C_{1-6}$ alkoxy($C_{1-6}$)alkyl, $C_{2-6}$ alkenyl, $C_{2-6}$ haloalkenyl, $C_{2-6}$ alkynyl, $C_{3-7}$ cycloalkyl (itself optionally substituted with $C_{1-6}$ alkyl or halogen), $C_{5-7}$ cycloalkenyl (itself optionally substituted with $C_{1-6}$ alkyl or halogen), hydroxy, $C_{1-10}$ alkoxy, $C_{1-10}$ alkoxy($C_{1-10}$)alkoxy, tri($C_{1-4}$)alkylsilyl($C_{1-6}$)alkoxy, $C_{1-6}$ alkoxycarbonyl($C_{1-10}$)alkoxy, $C_{1-10}$ haloalkoxy, aryl($C_{1-4}$)alkoxy (where the aryl group is optionally substituted), $C_{3-7}$ cycloalkyloxy (where the cycloalkyl group is optionally substituted with $C_{1-6}$ alkyl or halogen), $C_{1-10}$ alkenyloxy, $C_{1-10}$ alkynyloxy, SH, $C_{1-10}$ alkylthio, $C_{1-10}$ haloalkylthio, aryl($C_{1-4}$)alkylthio (where the aryl group may be further optionally substituted), $C_{3-7}$ cycloalkylthio (where the cycloalkyl group is optionally substituted with $C_{1-6}$ alkyl or halogen), tri($C_{1-4}$)alkylsilyl($C_{1-6}$)alkylthio, arylthio (where the aryl group is optionally substituted), $C_{1-6}$ alkylsulfonyl, $C_{1-6}$ haloalkylsulfonyl, $C_{1-6}$ alkylsulfinyl, $C_{1-6}$ haloalkylsulfinyl, arylsulfonyl (where the aryl group is optionally substituted), tri($C_{1-4}$)alkylsilyl, aryldi($C_{1-4}$)alkylsilyl, ($C_{1-4}$)alkyldiarylsilyl, triarylsilyl, $C_{1-10}$ alkylcarbonyl, $HO_2C$, $C_{1-10}$ alkoxycarbonyl, aminocarbonyl, $C_{1-6}$ alkylaminocarbonyl, di($C_{1-6}$ alkyl)aminocarbonyl, N—($C_{1-3}$ alkyl)-N—($C_{1-3}$ alkoxy)aminocarbonyl, $C_{1-6}$ alkylcarbonyloxy, arylcarbonyloxy (where the aryl group is optionally substituted), di($C_{1-6}$)alkylaminocarbonyloxy, aryl (itself optionally substituted), heteroaryl (which itself may be further optionally substituted), heterocyclyl (itself optionally substituted with $C_{1-6}$ alkyl or halogen), aryloxy (where the aryl group is optionally substituted), heteroaryloxy (where the heteroaryl group is optionally substituted), heterocyclyloxy (where the heterocyclyl group is optionally substituted with $C_{1-6}$ alkyl or halogen), amino, $C_{1-6}$ alkylamino, di($C_{1-6}$)alkylamino, $C_{1-6}$ alkylcarbonylamino and N—($C_{1-6}$)alkylcarbonyl-N—($C_{1-6}$)alkylamino.

For substituted phenyl moieties, heterocyclyl and heteroaryl groups it is preferred that one or more substituents are independently selected from halogen, $C_{1-6}$ alkyl, $C_{1-6}$ haloalkyl, $C_{1-6}$ alkoxy($C_{1-6}$)alkyl, $C_{1-6}$ alkoxy, $C_{1-6}$ haloalkoxy, $C_{1-6}$ alkylthio, $C_{1-6}$ haloalkylthio, $C_{1-6}$ alkylsulfinyl, $C_{1-6}$ haloalkylsulfinyl, $C_{1-6}$ alkylsulfonyl, $C_{1-6}$ haloalkylsulfonyl, $C_{2-6}$ alkenyl, $C_{2-6}$ haloalkenyl, $C_{2-6}$ alkynyl, $C_{3-7}$ cycloalkyl, nitro, cyano, $CO_2H$, $C_{1-6}$ alkylcarbonyl, $C_{1-6}$ alkoxycarbonyl, $R^{28}R^{29}N$ or $R^{30}R^{31}NC(O)$; wherein $R^{28}$, $R^{29}$, $R^{30}$ and $R^{31}$ are, independently, hydrogen or $C_{1-6}$ alkyl.

Haloalkenyl groups are alkenyl groups which are substituted with one or more of the same or different halogen atoms.

It is to be understood that dialkylamino substituents include those where the dialkyl groups together with the N atom to which they are attached form a five, six or seven-membered heterocyclic ring which may contain one or two further heteroatoms selected from O, N or S and which is optionally substituted by one or two independently selected ($C_{1-6}$)alkyl groups. When heterocyclic rings are formed by joining two groups on an N atom, the resulting rings are suitably pyrrolidine, piperidine, thiomorpholine and morpholine each of which may be substituted by one or two independently selected ($C_{1-6}$) alkyl groups.

Preferably the optional substituents on an alkyl moiety include one or more of halogen, nitro, cyano, $HO_2C$, $C_{1-6}$ alkoxy (itself optionally substituted by $C_{1-10}$ alkoxy), aryl ($C_{1-4}$)alkoxy, $C_{1-10}$ alkylthio, $C_{1-10}$ alkylcarbonyl, $C_{1-10}$ alkoxycarbonyl, $C_{1-6}$ alkylaminocabonyl, di($C_{1-6}$ alkyl)aminocarbonyl, ($C_{1-6}$)alkylcarbonyloxy, optionally substituted phenyl, heteroaryl, aryloxy, arylcarbonyloxy, heteroaryloxy, heterocyclyl, heterocyclyloxy, $C_{3-7}$ cycloalkyl (itself optionally substituted with ($C_{1-6}$)alkyl or halogen), $C_{3-7}$ cycloalkyloxy, $C_{5-7}$ cycloakenyl, $C_{1-6}$ alkylsulfonyl, $C_{1-6}$ alkylsulfyl, tri($C_{1-4}$)alkylsilyl, tri($C_{1-4}$)alkylsilyl($C_{1-6}$)alkoxy, aryldi($C_{1-4}$)alkylsilyl, ($C_{1-4}$) alkyldiarylsilyl and triarylsilyl.

Preferably the optional substituents on alkenyl or alkynyl include one or more of halogen, aryl and $C_{3-7}$ cycloalkyl.

It is more preferred that heterocyclyl is optionally substituted by $C_{1-6}$ alkyl.

Preferably the optional substituents for cycloalkyl include halogen, cyano and $C_{1-3}$ alkyl.

Preferably the optional substituents for cycloalkenyl include $C_{1-3}$ alkyl, halogen and cyano.

In a further aspect, the present invention provides a compound of formula (IA):

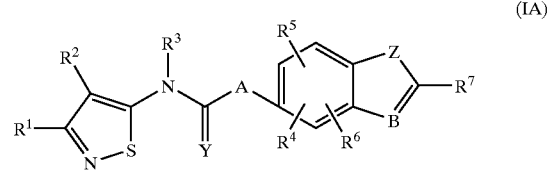

(IA)

wherein A, B, Y, Z, $R^1$, $R^2$, $R^3$, $R^4$, $R^5$, $R^6$ and $R^7$ are as defined above for a compound of formula (I).

More preferred compounds of formula (IA) are those wherein $R^1$ is hydrogen, halogen, $C_{1-6}$ alkyl, $C_{2-6}$ alkenyl, $C_{2-6}$ alkynyl, $C_{1-6}$ cyanoalkyl, $C_{1-6}$ haloalkyl, $C_{1-6}$ alkoxy, $C_{1-6}$ haloalkoxy, $C_{1-6}$ alkylthio, $C_{1-6}$ haloalkylthio, $C_{3-6}$ cycloalkyl, $C_{3-7}$ cycloalkyl($C_{1-4}$)alkyl, $C_{1-6}$ alkoxy($C_{1-6}$)alkyl, cyano, nitro or $SF_5$; A is $C_{1-6}$ alkylene, $C_{1-6}$ alkenylene, $C_{1-6}$ alkylenoxy, oxy($C_{1-6}$)alkylene, $C_{1-6}$ alkylenethio or $C_{1-6}$ alkylenethio, each of which is optionally substituted by $C_{1-3}$ alkyl, $C_{1-3}$ haloalkyl, $C_{1-3}$ cyanoalkyl, halogen, $C_{1-3}$ alkoxy, $C_{1-6}$ alkoxycarbonyl, cyano, =O, =NR$^{20}$ or =CR$^{21}R^{22}$, provided that A is not $CH_2$ or $CH_2O$; B is N or $CR^8$; Y is O, S or $NR^9$; Z is O, S or $NR^{10}$; $R^3$ is hydrogen, $C_{1-10}$ alkyl, benzyloxymethyl, benzoyloxymethyl, $C_{1-6}$alkoxy($C_{1-6}$)alkyl, $C_{2-6}$ alkenyl ($C_{1-6}$)alkyl (especially allyl), $C_{2-6}$ alkynyl($C_{1-6}$)alkyl (especially propargyl), $C_{1-10}$ alkylcarbonyl or $C_{1-10}$ alkoxycarbonyl (especially isobutoxycarbonyl); $R^4$, $R^5$ and $R^6$ are independently selected from hydrogen, halogen, $C_{1-6}$ alkyl, $C_{1-6}$ alkoxy, $C_{1-6}$ haloalkoxy, $C_{1-6}$ alkylthio, $C_{1-6}$ haloalkylthio, $C_{1-6}$ alkylsulfinyl, $C_{1-6}$ haloalkylsulfinyl, $C_{1-6}$ alkylsulfonyl, $C_{1-6}$ haloalkylsulfonyl, $C_{1-6}$ haloalkyl, cyano, nitro, $C_{1-6}$ alkylcarbonyl, $C_{1-6}$ alkoxycarbonyl or $SF_5$; $R^7$ is cyano, $C_{1-8}$ alkyl, $C_{1-6}$ haloalkyl, $C_{1-6}$ cyanoalkyl, $C_{2-6}$ alkenyl, $C_{2-6}$ alkynyl, $C_{3-7}$ cycloalkyl, $C_{3-7}$ halocycloalkyl, $C_{3-7}$ cyanocycloalkyl, $C_{1-3}$ alkyl($C_{3-7}$)cycoalkyl, $C_{1-3}$ alkyl($C_{3-7}$)halocycloalkyl, $C_{5-6}$ cycloalkenyl, $C_{3-7}$ cycloalkyl($C_{1-6}$)alkyl, $C_{5-6}$ cycloalkenyl($C_{1-6}$)alkyl, $C_{2-6}$ haloalkenyl, $C_{1-6}$ cyanoalkenyl, $C_{1-6}$ alkoxy($C_{1-6}$)alkyl, $C_{3-6}$ alkenyloxy ($C_{1-6}$)alkyl, $C_{3-6}$ alkynyloxy($C_{1-6}$)alkyl, aryloxy($C_{1-6}$)alkyl, formyl, $C_{1-6}$ carboxyalkyl, $C_{1-6}$ alkylcarbonyl($C_{1-6}$)alkyl, $C_{2-6}$ alkenylcarbonyl($C_{1-6}$)alkyl, $C_{2-6}$ alkynylcarbonyl($C_{1-6}$) alkyl, $C_{1-6}$ alkoxycarbonyl($C_{1-6}$)alkyl, $C_{3-6}$ alkenyloxycarbonyl($C_{1-6}$)alkyl, $C_{3-6}$ alkynyloxycarbonyl($C_{1-6}$)alkyl, aryloxycarbonyl($C_{1-6}$)alkyl, $C_{1-6}$ alkylthio($C_{1-6}$)alkyl, $C_{1-6}$ alkylsulfinyl($C_{1-6}$)alkyl, $C_{1-6}$ alkylsulfonyl($C_{1-6}$)alkyl, aminocarbonyl($C_{1-6}$)alkyl, aminocarbonyl($C_{2-6}$)

alkenyl, aminocarbonyl($C_{2-6}$)alkynyl, $C_{1-6}$ alkylaminocarbonyl($C_{1-6}$)alkyl, di($C_{1-6}$)alkylaminocarbonyl ($C_{1-6}$)alkyl, $C_{1-6}$alkylaminocarbonyl($C_{1-6}$)alkenyl, di($C_{1-6}$) alkylaminocarbonyl($C_{1-6}$)alkenyl, alkylaminocarbonyl ($C_{1-6}$)alkynyl, di($C_{1-6}$)alkylaminocarbonyl($C_{1-6}$)alkynyl, $C_{1-6}$ alkoxycarbonyl, $C_{1-6}$ alkylcarbonyl, aminocarbonyl, $C_{1-6}$ alkylaminocarbonyl, di($C_{1-6}$)alkylaminocarbonyl, phenyl (optionally substituted by halo, nitro, cyano, $C_{1-6}$ alkyl, $C_{1-6}$ haloalkyl, $C_{1-6}$ alkoxy or $C_{1-6}$ haloalkoxy), phenyl ($C_{1-4}$)alkyl (wherein the phenyl group is optionally substituted by halo, nitro, cyano, $C_{1-6}$ alkyl, $C_{1-6}$ haloalcyl, $C_{1-6}$ alkoxy or $C_{1-6}$ haloalkoxy), phenyl($C_{2-4}$)alkenyl, (wherein the phenyl group is optionally substituted by halo, nitro, cyano, $C_{1-6}$ alkyl, $C_{1-6}$ haloalkyl, $C_{1-6}$ alkoxy or $C_{1-6}$ haloalkoxy), heteroaryl (optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyl (optionally substituted by halo, nitro, cyano, $C_{1-6}$ alkyl, $C_{1-6}$ haloalkyl, $C_{1-6}$ alkoxy or $C_{1-6}$ haloalkoxy), heteroaryl($C_{1-4}$)alkyl (where the heteroaryl may be substituted by halo, nitro, cyano, $C_{1-6}$ alkyl, $C_{1-6}$ haloalkyl, $C_{1-6}$ alkoxy or $C_{1-6}$ haloalkoxy), heterocyclyl ($C_{1-4}$)alkyl (where the heterocyclyl may be substituted by halo, cyano, $C_{1-6}$ alkyl, $C_{1-6}$ haloalkyl, $C_{1-6}$ alkoxy or $C_{1-6}$ haloalkoxy), $R^{15}O$, $C_{1-8}$ alkylthio, $R^{16}R^{17}N$ or $R^{18}ON=C$ ($R^{19}$); $R^2$ is hydrogen, halogen, $C_{1-6}$ alkyl, $C_{2-6}$ alkenyl, $C_{1-6}$ alkynyl, $C_{1-6}$ haloalkyl, $C_{1-6}$ alkoxy, $C_{1-6}$ alkoxy($C_{1-6}$)alkyl, $C_{1-6}$ haloalkoxy, $C_{1-6}$ alkylthio, $C_{1-6}$ haloalkylthio, $C_{1-6}$ alkylsulfinyl, $C_{1-6}$ haloalkylsufinyl, $C_{1-6}$ alkylsulfonyl, $C_{1-6}$ haloalkylsulfonyl, $C_{1-6}$ haloalkyl, cyano, nitro, formyl, $CH=NOR^{11}$, $C_{1-6}$ alkylcarbonyl, $C_{1-6}$ alkoxycarbonyl or $SF_5$; or together $R^1$ and $R^2$ together with the atoms to which they are attached may be joined to form a five, six or seven-membered saturated or unsaturated ring carbocylic or heterocyclic ring which may contain one or two hetero atoms selected from O, N or S and which may be optionally substituted by $C_{1-6}$ alkyl, $C_{1-6}$ haloalkyl or halogen; $R^9$ is cyano, nitro, $C_{1-6}$ alkyl, $C_{1-6}$ haloalkyl, $C_{3-7}$ cycloalkyl, $C_{3-7}$ cycloalkyl($C_{1-6}$)alkyl, $CH_2(C_{2-6})$ alkenyl, $CH_2(C_{2-6})$alknyl, phenyl (optionally substituted by halo, nitro, cyano, $C_{1-6}$ alkyl, $C_{1-6}$ haloalkyl, $C_{1-6}$ alkoxy or $C_{1-6}$ haloalkoxy) heteroaryl (optionally substituted by halo, nitro, cyano, $C_{1-6}$ alkyl, $C_{1-6}$ haloalkyl, $C_{1-6}$ alkoxy or $C_{1-6}$ haloalkoxy), $C_{1-6}$ alkylcarbonyl, $C_{1-6}$ alkoxycarbonyl, $C_{1-6}$ alkylamino, di($C_{1-6}$)alkylamino, $C_{1-6}$ alkylcarbonylamino, $C_{1-6}$ alkoxycarbonylamino, $C_{1-6}$ alkoxy, $C_{1-6}$ alkylthio, $C_{1-6}$ alkylsulfinyl, $C_{1-6}$ alkylsulfonyl, $C_{1-6}$ haloalkylthio, $C_{1-6}$ haloalkylsulfinyl, $C_{1-6}$ haloalkylsulfonyl, arylthio, arylsulfinyl, arylsulfonyl or $OCO(C_{1-6})$alkyl; $R^{10}$ is hydrogen, $C_{1-8}$ alkyl, $C_{1-6}$ haloalkyl, $C_{1-6}$ cyanoalkyl, $C_{2-6}$ alkenyl, $C_{2-6}$ alkynyl, $C_{3-7}$ cycloalkyl, $C_{2-6}$ haloalkenyl, $C_{3-7}$ cycloalkyl($C_{1-6}$)alkyl, $C_{1-6}$ alkoxy($C_{1-6}$)alkyl, $C_{1-6}$ alkoxycarbonyl, $C_{1-6}$ alkylcarbonyl, $C_{1-6}$ alkylaminocarbonyl, di($C_{1-6}$)alkylaminocarbonyl, phenyl (optionally substituted by halo, nitro, cyano, $C_{1-6}$ alkyl, $C_{1-6}$ haloalkyl, $C_{1-6}$ alkoxy or $C_{1-6}$ haloalkoxy) or heteroaryl (optionally substituted by halo, nitro, cyano, $C_{1-6}$ alkyl, $C_{1-6}$ haloalkyl, $C_{1-6}$ alkoxy or $C_{1-6}$ haloalkoxy); $R^{20}$ is $C_{1-6}$ alkyl, $OR^{23}$ or $NR^{24}R^{25}$; $R^{21}$ is hydrogen, $C_{1-6}$ alkyl or $C_{1-6}$ haloalkyl; $R^{22}$ is hydrogen, $C_{1-6}$ alkyl, $C_{1-6}$ haloalkyl, $C_{1-6}$ alkoxy, cyano, $C_{1-6}$ alkoxycarbonyl, $C_{1-6}$ alkylcarbonyl or $NR^{26}R^{27}$; $R^8$ is hydrogen, halogen, nitro, cyano, $C_{1-8}$ alkyl, $C_{1-6}$ haloalkyl, $C_{1-6}$ cyanoalkyl, $C_{2-6}$ alkenyl, $C_{2-6}$ alkynyl, $C_{3-7}$ cycloalkyl, $C_{2-6}$ haloalkenyl $C_{3-7}$ cycloalkyl($C_{1-6}$)alkyl, $C_{1-6}$ alkoxy($C_{1-6}$)alkyl, $C_{1-6}$ alkoxycarbonyl, $C_{1-6}$ alkylcarbonyl, $C_{1-6}$ alkylamninocarbonyl, di($C_{1-6}$) alkylaminocarbonyl, $C_{1-6}$ alkoxycarbonyl($C_{1-6}$)alkyl, $C_{1-6}$ alkylcarbonyl($C_{1-6}$)alkyl, $C_{1-6}$ alkylaminocarbonyl($C_{1-6}$) alkyl, di($C_{1-6}$)alkylaminocarbonyl($C_{1-6}$)alkyl, phenyl (optionally substituted by halo, nitro, cyano, $C_{1-6}$ alkyl, $C_{1-6}$ haloalkyl, $C_{1-6}$ alkoxy or $C_{1-6}$ haloalkoxy), phenyl($C_{1-6}$) alkyl (wherein the phenyl group is optionally substituted by halo, nitro, cyano, $C_{1-6}$ alkyl, $C_{1-6}$ haloalkyl, $C_{1-6}$ alkoxy or $C_{1-6}$ haloalkoxy), heteroaryl (optionally substituted by halo, nitro, cyano, $C_{1-6}$ alkyl, $C_{1-6}$ haloalkyl, $C_{1-6}$ alkoxy or $C_{1-6}$ haloalkoxy) or heteroaryl($C_{1-6}$)alkyl (wherein the heteroaryl group is optionally substituted by halo, nitro, cyano, $C_{1-6}$ alkyl, $C_{1-6}$ haloalkyl, $C_{1-6}$ alkoxy or $C_{1-6}$ haloalkoxy); $R^{23}$ is $C_{1-6}$ alkyl or optionally substituted phenyl($C_{1-2}$)alkyl; $R^{24}$ and $R^{25}$ are, independently, hydrogen, $C_{1-8}$ alkyl or phenyl (optionally substituted by halo, nitro, cyano, $C_{1-6}$ alkyl, $C_{1-6}$ haloalkyl, $C_{1-6}$ alkoxy or $C_{1-6}$ haloalkoxy); $R^{15}$ is hydrogen, $C_{1-8}$ alkyl, $C_{1-6}$ haloalkyl, $C_{1-6}$ cyanoalkyl, $C_{2-6}$ alkenyl, $C_{2-6}$ alkynyl, $C_{1-6}$ alkoxy($C_{1-6}$)alkyl, phenyl($C_{1-4}$)alkyl (wherein the phenyl group is optionally substituted by halo, nitro, cyano, $C_{1-6}$ alkyl, $C_{1-6}$ haloalkyl, $C_{1-6}$ alkoxy or $C_{1-6}$ haloalkoxy), heteroaryl($C_{1-4}$)alkyl (wherein the heteroaryl group is optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyl (optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyl($C_{1-4}$)alkyl (wherein the heterocyclyl group is optionally substituted by halo, nitro, cyano, $C_{1-6}$ alkyl, $C_{1-6}$ haloalkyl, $C_{1-6}$ alkoxy or $C_{1-6}$ haloalkoxy), $C_{1-6}$ alkoxycarbonyl($C_{1-6}$)alkyl or $N=C(CH_3)_2$; $R^{19}$ is $C_{1-6}$ alkyl, $C_{1-6}$ haloalkyl or phenyl (optionally substituted by halo, nitro, cyano, $C_{1-6}$ alkyl, $C_{1-6}$ haloalkyl, $C_{1-6}$ alkoxy or $C_{1-6}$ haloalkoxy); $R^{16}$ and $R^{17}$ are, independently, hydrogen, $C_{1-8}$ alkyl $C_{3-7}$ cycloalkyl, $C_{3-6}$ alkenyl, $C_{3-6}$ alkynyl, $C_{3-7}$ cycloalkyl($C_{1-4}$)alkyl, $C_{2-6}$ haloalkenyl, $C_{1-6}$ alkoxy($C_{1-6}$) alkyl, $C_{1-6}$ alkoxycarbonyl, or $R^{16}$ and $R^{17}$ together with the N atom to which they are attached form a five, six or seven-membered heterocyclic ring which may contain one or two further hetero atoms selected from O, N or S and which may be optionally substituted by one or two $C_{1-6}$ alkyl groups; $R^{18}$ and $R^{11}$ are, independently, $C_{1-6}$ alkyl or phenyl ($C_{1-2}$)alkyl (wherein the phenyl group is optionally substituted by halo, nitro, cyano, $C_{1-6}$ alkyl, $C_{1-6}$ haloalkyl, $C_{1-6}$ alkoxy or $C_{1-6}$ haloalkoxy); and $R^{26}$ and $R^{27}$ are, independently, hydrogen, $C_{1-8}$ alkyl, $C_{3-7}$ cycloalkyl, $C_{3-6}$ alkenyl, $C_{3-6}$ alkynyl, $C_{2-6}$ haloalkyl, $C_{1-6}$ alkoxy($C_{1-6}$) alkyl, $C_{1-6}$ alkoxycarbonyl($C_{1-6}$)alkyl, carboxy($C_{1-6}$)alkyl or phenyl($C_{1-2}$)alkyl; or $R^{26}$ and $R^{27}$ together with the N atom to which they are attached form a five, six or seven-membered heterocyclic ring which may contain one or two further heteroatoms selected from O, N or S and which may be optionally substituted by one or two $C_{1-6}$ alkyl groups.

It is preferred that A is $C_{1-6}$ alkylene, $C_{1-6}$ alkenylene, $C_{1-6}$ alkylenoxy, oxy($C_{1-6}$)alkylene or $C_{1-6}$ alkylenamino, each of which is optionally substituted by $C_{1-3}$ alkyl, $C_{1-3}$ haloalkyl, $C_{1-3}$ cyanoalkyl, halogen, $C_{1-3}$ alkoxy, $C_{1-6}$ alkoxycarbonyl, cyano, $=O$, $=NR^{20}$ or $=CR^{21}R^{22}$; where $R^{20}$ is $C_{1-6}$ alkyl, $OR^{23}$ or $NR^{24}R^{25}$; $R^{23}$ is $C_{1-6}$ alkyl or phenyl($C_{1-2}$)alkyl (where the phenyl group is optionally substituted by halo, nitro, cyano, $C_{1-6}$ alkyl, $C_{1-6}$ haloalkyl, $C_{1-6}$ alkoxy or $C_{1-6}$ haloalkoxy); $R^{24}$ and $R^{25}$ are, independently, $C_{1-8}$ alkyl or phenyl (which may be optionally substituted by halo, nitro, cyano, $C_{1-6}$ alkyl, $C_{1-6}$ haloalkyl, $C_{1-6}$ alkoxy or $C_{1-6}$ haloalkoxy); $R^{21}$ is hydrogen, $C_{1-6}$ alkyl or $C_{1-6}$ haloalkyl; $R^{22}$ is hydrogen, $C_{1-6}$ alkyl, $C_{1-6}$ haloalkyl, $C_{1-6}$ alkoxy, cyano, $C_{1-6}$ alkoxycarbonyl, $C_{1-6}$ alkylcarbonyl or $NR^{26}R^{27}$; and $R^{26}$ and $R^{27}$ are, independently, hydrogen, $C_{1-8}$ alkyl, $C_{3-7}$ cycloalkyl, $C_{3-6}$ alkenyl, $C_{3-6}$ alkynyl, $C_{2-6}$ haloalkyl, $C_{1-6}$ alkoxy($C_{1-6}$)alkyl, $C_{1-6}$ alkoxycarbonyl($C_{1-6}$)alkyl, carboxy $(C_{1-6})$alkyl or phenyl$(C_{1-2})$alkyl; or $R^{26}$ and $R^{27}$ together with the N atom to which they are attached form a five, six or seven-membered heterocyclic ring which may contain one or two further heteroatoms selected from O, N or S and which may be optionally substituted by one or two $C_{1-6}$ alkyl groups; provided that A is not $CH_2$ or $CH_2O$.

A is more preferably $C_{1-4}$ alkylene (optionally substituted by halogen, $C_{1-3}$ alkyl or $C_{1-3}$ alkoxy, —C(O)— or $C_{1-4}$ alkyleneoxy (which may be optionally substituted by $C_{1-3}$ alkyl); provided that A is not $CH_2$ or $CH_2O$.

It is even more preferred that A is $C_{1-2}$ alkyl-substituted $C_{1-4}$ alkylene, fluoro-substituted $C_{1-4}$ alkylene, methoxy-substituted $C_{1-4}$ alkylene, —C(O)— or $C_{2-4}$ alkyleneoxy; still more preferably A is $C_{1-2}$ alkyl-substituted $C_{1-4}$ alkylene, fluoro-substituted $C_{1-4}$ alkylene or methoxy-substituted $C_{1-4}$ alkylene.

It is further preferred that A is $CH(CH_3)CH_2$, $CH_2CH(CH_3)$, $CH(CH_3)$, CHF, $CH(OCH_3)$ or $CH(CH_3)O$; further preferred that A is $CH(CH_3)CH_2$, $CH_2CH(CH_3)$, $CH(CH_3)$, CHF or $CH(CH_3)O$; it is especially preferred that A is CHF, $CH(OCH_3)$ or $CH(CH_3)$; and most preferably A is CHF or $CH(CH_3)$.

One group of preferred compounds is that where A is optionally fluoro-substituted $C_{1-4}$ alkylene, —C(O)— or $C_{2-4}$ alkyleneoxy, provided that A is not $CH_2$.

B is preferably N.

Y is preferably O or S.

Y is more preferably O.

Z is preferably O or S.

Z is more preferably O.

It is preferred that $R^1$ is hydrogen, halogen, $C_{1-6}$ alkyl, $C_{1-6}$ cyanoalkyl, $C_{1-6}$ haloalkyl, $C_{3-7}$ cycloalkyl$(C_{1-4})$alkyl, $C_{1-6}$ alkoxy$(C_{1-6})$alkyl, $C_{2-6}$ alkenyl, $C_{2-6}$ alkynyl, $C_{1-6}$ alkoxy, $C_{1-6}$ haloalkoxy, $C_{1-6}$ alkylthio, $C_{1-6}$ haloalkylthio, $C_{3-6}$ cycloalkyl, cyano, nitro or $SF_5$.

$R^1$ is more preferably hydrogen, halogen, $C_{1-6}$ alkyl, $C_{2-6}$ alkenyl, $C_{1-6}$ haloalkyl, $C_{1-6}$ alkoxy, $C_{1-6}$ haloalkoxy, $C_{1-6}$ alkylthio, $C_{1-6}$ haloalkylthio, $C_{3-6}$ cycloalkyl, cyano, nitro or $SF_5$.

It is even more preferred that $R^1$ is hydrogen, halogen, $C_{1-6}$ alkyl, $C_{1-6}$ haloalkyl, $C_{1-6}$ alkoxy$(C_{1-6})$alkyl, $C_{2-6}$ alkenyl, $C_{1-6}$ alkoxy, $C_{1-6}$ haloalkoxy, $C_{1-6}$ alkylthio, $C_{1-6}$ haloalkylthio, $C_{3-6}$ cycloalkyl or cyano.

It is most preferred that $R^1$ is halogen, $C_{1-6}$ alkyl, $C_{1-6}$ haloalkyl, $C_{1-6}$ alkoxy or $C_{1-6}$ haloalkoxy.

It is preferred that $R^2$ is hydrogen, halogen, $C_{1-6}$ alkyl, $C_{1-6}$ haloalkyl, $C_{1-6}$ alkoxy$(C_{1-6})$alkyl, $C_{2-6}$ alkenyl, $C_{1-6}$ alkynyl, $C_{1-6}$ alkoxy, $C_{1-6}$ haloalkoxy, $C_{1-6}$ alkylthio, $C_{1-6}$ haloalkylthio, $C_{1-6}$ alkylsulfinyl, $C_{1-6}$ haloalkylsulfinyl, $C_{1-6}$ alkylsulfonyl, $C_{1-6}$ haloalkylsulfonyl, cyano, nitro, formyl, $C_{1-6}$ alkylcarbonyl, $C_{1-6}$ alkoxycarbonyl or CH=NOR$^{11}$ or $SF_5$; or $R^1$ and $R^2$ together with the atoms to which they are attached may be joined to form a five, six or seven-membered saturated or unsaturated, carbocylic or heterocyclic ring which may contain one or two heteroatoms selected from O, N or S and which is optionally substituted by $C_{1-6}$ alkyl, $C_{1-6}$ haloalkyl or halogen; where $R^{11}$ is phenyl$(C_{1-2})$ alkyl (wherein the phenyl group is optionally substituted by halo, nitro, cyano, $C_{1-6}$ alkyl, $C_{1-6}$ haloalkyl, $C_{1-6}$ alkoxy or $C_{1-6}$ haloalkoxy) or $C_{1-6}$ alkyl.

It is more preferred that $R^2$ is hydrogen, halogen, $C_{1-6}$ alkyl, $C_{1-6}$ haloalkyl, $C_{1-6}$ alkoxy $(C_{1-6})$alkyl, $C_{1-6}$ alkoxy, $C_{1-6}$ haloalkoxy, $C_{1-6}$ alkylthio or $SF_5$; or $R^1$ and $R^2$ together with the atoms to which they are attached form a cyclopentane or benzene ring optionally substituted by $C_{1-6}$ alkyl, $C_{1-6}$ haloalkyl or halogen.

$R^2$ is even more preferably hydrogen, halogen, $C_{1-6}$ alkyl, $C_{1-6}$ haloalkyl, $C_{1-6}$ alkoxy, $C_{1-6}$ haloalkoxy, $C_{1-6}$ alkoxy $(C_{1-6})$alkyl, $C_{1-6}$ alkylthio or $SF_5$; or $R^1$ and $R^2$ together with the atoms to which they are attached form a benzene ring optionally substituted by $C_{1-6}$ alkyl, $C_{1-6}$ haloalkyl or halogen; or alternatively the ring may be a cyclopentane ring.

It is further preferred that $R^2$ is hydrogen, halogen, $C_{1-6}$ alkyl, $C_{1-6}$ haloalkyl, $C_{1-6}$ alkoxy$(C_{1-6})$alkyl, $C_{1-6}$ alkoxy, $C_{1-6}$ haloalkoxy, or $R^1$ and $R^2$ together with the atoms to which they are attached form a cyclopentane ring optionally substituted by $C_{1-6}$ alkyl, $C_{1-6}$ haloalkyl or halogen.

$R^2$ is most preferably halogen, $C_{1-6}$ alkyl, $C_{1-6}$ haloalkyl, $C_{1-6}$ alkoxy, $C_{1-6}$ alkoxy$(C_{1-6})$alkyl or $C_{1-6}$ haloalkoxy.

It is preferred that $R^3$ is hydrogen, $C_{1-10}$ alkyl, $C_{1-6}$ alkylcarbonyloxy$(C_{1-6})$alkyl, benzoyloxymethyl (where the phenyl ring is optionally substituted with halogen or $C_{1-4}$ alkyl), $C_{1-6}$ alkoxy$(C_{1-6})$alkyl (where the alkyl group is optionally substituted by aryl or $C_{1-4}$ alkoxycarbonyl), $C_{2-6}$ alkenyloxy$(C_{1-4})$alkyl, $C_{2-6}$ alkynyloxy$(C_{1-4})$alkyl, benzyloxy$(C_{1-4})$alkyl (where the phenyl ring is optionally substituted with halogen or $C_{1-4}$ alkyl), $C_{3-7}$ cycloalkyl $(C_{1-4})$alkyl, heteroaryl$(C_{1-3})$alkyl (where the heteroaryl group is optionally substituted with halogen), tri$(C_{1-4})$ alkylsilyl$(C_{1-6})$alkyl, $C_{2-6}$ alkenyl$(C_{1-6})$alkyl (especially allyl), $C_{2-6}$ haloalkenyl$(C_{1-6})$alkyl, $C_{1-4}$ alkoxycarbonyl $(C_{2-6})$alkenyl$(C_{1-6})$alkyl, $C_{2-6}$ alkynyl$(C_{1-6})$alkyl, tri$(C_{1-6})$ alkylsilyl$(C_{2-6})$alkynyl$(C_{1-6})$alkyl or $C_{1-10}$ alkylcarbonyl.

It is further preferred that $R^3$ is hydrogen, $C_{1-6}$ alkyl, $C_{1-6}$ alkylcarbonyloxymethyl, benzoyloxymethyl (where the phenyl ring is optionally substituted with halogen or $C_{1-4}$ alkyl), $C_{1-6}$ alkoxymethyl, $C_{2-6}$ alkenyloxymethyl, $C_{2-6}$ alkynyloxymethyl, benzyloxymethyl (where the phenyl ring is optionally substituted with halogen or $C_{1-4}$ alkyl), $C_{2-6}$ alkynyl$(C_{1-6})$alkyl (especially propargyl) or $C_{1-10}$ alkylcarbonyl.

$R^3$ is more preferably hydrogen, $C_{1-6}$ alkyl, $C_{1-6}$ alkoxy $(C_{1-6})$alkyl, benzyloxymethyl or benzoyloxymethyl; or alternatively $R^3$ may be $C_{1-6}$ alkylcarbonyloxymediyl.

It is most preferred that $R^3$ is hydrogen, $C_{1-6}$ alkyl, $C_{1-6}$ alkylcarbonyloxymethyl or $C_{1-6}$ alkoxymethyl.

It is preferred that $R^4$, $R^5$ and $R^6$ are, independently, hydrogen, halogen, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ haloalkylthio, $C_{1-6}$ alkylsulfinyl, $C_{1-6}$ haloalkylsulfinyl, $C_{1-6}$ alkylsulfonyl, $C_{1-6}$ haloalkylsulfonyl, cyano, nitro, $C_{1-6}$ alkylcarbonyl or $C_{1-6}$ alkoxycarbonyl.

It is more preferred that $R^4$, $R^5$ and $R^6$ are, independently, hydrogen, halogen or $C_{1-3}$ alkyl.

It is even more preferred that $R^4$, $R^5$ and $R^6$ are, independently, hydrogen or halogen (especially fluorine).

It is preferred that $R^7$ is cyano, $C_{1-8}$ alkyl, $C_{1-8}$ haloalkyl, $C_{1-8}$ cyanoalkyl, $C_{3-7}$ cycloalkyl$(C_{1-6})$alkyl, $C_{5-6}$ cycloalkenyl$(C_{1-6})$alkyl, $C_{1-6}$ alkoxy$(C_{1-6})$alkyl, $C_{3-6}$ alkenyloxy$(C_{1-6})$alkyl, $C_{3-6}$ alkynyoxy$(C_{1-6})$alkyl, aryloxy $(C_{1-6})$alkyl, $C_{1-6}$ carboxyalkyl, $C_{1-6}$ alkylcarbonyl$(C_{1-6})$ alkyl, $C_{2-6}$ alkenylcarbonyl$(C_{1-6})$alkyl, $C_{2-6}$ alkynylcarbonyl$(C_{1-6})$alkyl, $C_{1-6}$ alkoxycarbonyl$(C_{1-6})$ alkyl, $C_{3-6}$ alkenyloxycarbonyl$(C_{1-6})$alkyl, $C_{3-6}$ alkynyloxycarbonyl$(C_{1-6})$alkyl, aryloxycarbonyl$(C_{1-6})$alkyl, $C_{1-6}$ alkylthio$(C_{1-6})$alkyl, $C_{1-6}$ alkylsulfinyl$(C_{1-6})$alkyl, $C_{1-6}$ alkylsulfonyl$(C_{1-6})$alkyl, aminocarbonyl$(C_{1-6})$alkyl, $C_{1-6}$ alkylaminocarbonyl$(C_{1-6})$alkyl, di$(C_{1-6})$alkylaminocarbonyl $(C_{1-6})$alkyl, phenyl$(C_{1-4})$alkyl (wherein the phenyl group is optionally substituted by halo, nitro, cyano, $C_{1-6}$ alkyl, $C_{1-6}$ haloalkyl, $C_{1-6}$ alkoxy or $C_{1-6}$ haloalkoxy), heteroaryl $(C_{1-4})$alkyl (where the heteroaryl group is optionally substituted by halo, nitro, cyano, $C_{1-6}$, alkyl, $C_{1-6}$ haloalkyl, $C_{1-6}$ alkoxy or $C_{1-6}$ haloalkoxy), heterocyclyl$(C_{1-4})$alkyl (where the heterocyclyl group is optionally substituted by halo, cyano, $C_{1-6}$ alkyl, $C_{1-6}$ haloalkyl, $C_{1-6}$ alkoxy or $C_{1-6}$ haloalkoxy), $C_{2-6}$ alkenyl, $C_{2-6}$ haloalkenyl, $C_{1-6}$ cyanoalkenyl, $C_{5-6}$ cycloalkenyl, aminocarbonyl($C_{2-6}$) alkenyl, $C_{1-6}$ alkylaminocarbonyl($C_{1-6}$)alkenyl, di($C_{1-6}$) alkylaminocarbonyl($C_{1-6}$)alkenyl, phenyl($C_{2-4}$)alkenyl (wherein the phenyl group is optionally substituted by halo, nitro, cyano, $C_{1-6}$ alkyl, $C_{1-6}$ haloalkyl, $C_{1-6}$ alkoxy or $C_{1-6}$ haloalkoxy), $C_{2-6}$ alkynyl, aminocarbonyl-($C_{2-6}$)alkynyl, alkylaminocarbonyl($C_{1-6}$)alkynyl, di($C_{1-6}$) alkylaminocarbonyl($C_{1-6}$)alkynyl, $C_{3-7}$ cycloalkyl, $C_{3-7}$ halocycloalkyl, $C_{3-7}$ cyanocycloalkyl, $C_{1-3}$ alkyl($C_{3-7}$) cycloalkyl, $C_{1-3}$ alkyl($C_{3-7}$)halocycloalkyl, $C_{5-6}$ cycloalkenyl, formyl, $C_{1-6}$ alkoxycarbonyl, $C_{1-6}$ alkylcarbonyl, aminocarbonyl, $C_{1-6}$ alkylaminocarbonyl, di($C_{1-6}$)alkylaminocarbonyl, phenyl (optionally substituted by halo, nitro, cyano, $C_{1-6}$ alkyl, $C_{1-6}$ haloalkyl, $C_{1-6}$ alkoxy or $C_{1-6}$ haloalkoxy), heteroaryl (optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyl (optionally substituted by halo, nitro, cyano, $C_{1-6}$ alkyl, $C_{1-6}$ haloalkyl, $C_{1-6}$ alkoxy or $C_{1-6}$ haloalkoxy), $C_{1-8}$ alkylthio, $R^{15}O$, $R^{16}R^{17}N$ or $R^{18}ON=C(R^{19})$; where $R^{15}$ is hydrogen, $C_{1-8}$ alkyl, $C_{1-6}$ haloalkyl, $C_{1-6}$ cyanoalkyl, $C_{1-6}$ alkoxy($C_{1-6}$)alkyl, phenyl ($C_{1-4}$)alkyl, (wherein the phenyl group is optionally substituted by halo, nitro, cyano, $C_{1-6}$ alkyl, $C_{1-6}$ haloalkyl, $C_{1-6}$ alkoxy or $C_{1-6}$ haloalkoxy), heteroaryl($C_{1-4}$)alkyl (wherein the heteroaryl group is optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyl($C_{1-4}$)alkyl (wherein the heterocyclyl group is optionally substituted by halo, nitro, cyano, $C_{1-6}$ alkyl, $C_{1-6}$ haloalkyl, $C_{1-6}$ alkoxy or $C_{1-6}$ haloalkoxy), $C_{1-6}$ alkoxycarbonyl($C_{1-6}$)alkyl, $C_{2-6}$ alkenyl, $C_{2-6}$ alkynyl or $N=C(CH_3)_2$; $R^{19}$ is phenyl (optionally substituted by halo, nitro, cyano, $C_{1-6}$ alkyl, $C_{1-6}$ haloalkyl, $C_{1-6}$ alkoxy or $C_{1-6}$ haloalkoxy), $C_{1-6}$ alkyl or $C_{1-6}$ haloalkyl; $R^{16}$ and $R^{17}$ are, independently, hydrogen, $C_{1-8}$ alkyl, $C_{3-7}$cycloalkyl($C_{1-4}$)alkyl, $C_{2-6}$ haloalkyl, $C_{1-6}$ alkoxy($C_{1-6}$)alkyl, $C_{3-7}$ cycloalkyl, $C_{3-6}$ alkenyl, $C_{3-6}$ alkynyl or $C_{1-6}$ alkoxycarbonyl; and $R^{18}$ is phenyl($C_{1-2}$)alkyl (wherein the phenyl group is optionally substituted by halo, nitro, cyano, $C_{1-6}$ alkyl, $C_{1-6}$ haloalkyl, $C_{1-6}$ alkoxy or $C_{1-6}$ haloalkoxy) or $C_{1-6}$ alkyl.

$R^7$ is more preferably $C_{1-8}$ alkyl, $C_{1-6}$ haloalkyl, $C_{1-6}$ cyanoalkyl, $C_{2-6}$ alkenyl, $C_{2-6}$ alkynyl, $C_{3-7}$ cycloalkyl, $C_{3-7}$ halocycloalkyl, $C_{3-7}$ cyanocycloalkyl $C_{1-3}$ alkyl($C_{3-7}$) cycoalkyl, $C_{1-3}$ alkyl($C_{3-7}$)halocycloalkyl, $C_{5-6}$ cycloalkenyl, $C_{3-7}$ cycloalkyl($C_{1-6}$)alkyl, $C_{5-6}$ cycloalkenyl ($C_{1-6}$)alkyl, $C_{2-6}$ haloalkenyl, $C_{1-6}$cyanoalkenyl, $C_{1-6}$ alkoxy ($C_{1-6}$)alkyl, $C_{3-6}$ alkenyloxy($C_{1-6}$)alkyl, $C_{3-6}$ alkynyloxy ($C_{1-6}$)alkyl, aryloxy($C_{1-6}$)alkyl, $C_{1-6}$ carboxyalkyl, $C_{1-6}$ alkylcarbonyl($C_{1-6}$)alkyl, $C_{2-6}$ alkenylcarbonyl($C_{1-6}$)alkyl, $C_{2-6}$ alkyncarbonyl($C_{1-6}$)alkyl, $C_{1-6}$ alkoxycarbonyl($C_{1-6}$) alkyl, $C_{3-6}$ alkenyloxycarbonyl($C_{1-6}$)alkyl, $C_{3-6}$ alkynyloxycarbonyl($C_{1-6}$)alkyl, aryloxycarbonyl($C_{1-6}$)alkyl, $C_{1-6}$ alkylthio($C_{1-6}$)alkyl, $C_{1-6}$ alkylsulfinyl($C_{1-6}$)alkyl, $C_{1-6}$ alkylsulfonyl($C_{1-6}$)alkyl, aminocarbonyl($C_{1-6}$)alkyl, aminocarbonyl($C_{2-6}$)alkenyl, aminocarbonyl($C_{2-6}$)alkynyl, $C_{1-6}$ alkylaminocarbonyl($C_{1-6}$)alkyl, di($C_{1-6}$) alkylaminocarbonyl($C_{1-6}$)alkyl, $C_{1-6}$ alkylaminocarbonyl ($C_{1-6}$)alkenyl, di($C_{1-6}$)alkylaminocarbonyl($C_{1-6}$)alkenyl, alkylaminocarbonyl($C_{1-6}$)alkynyl, di($C_{1-6}$) alkylaminocarbonyl($C_{1-6}$)alkynyl, phenyl (optionally substituted by halo, nitro, cyano, $C_{1-6}$ alkyl, $C_{1-6}$ haloalkyl, $C_{1-6}$ alkoxy or $C_{1-6}$ haloalkoxy), phenyl($C_{1-4}$)alkyl (wherein the phenyl group is optionally substituted by halo, nitro, cyano, $C_{1-6}$ alkyl, $C_{1-6}$ haloalkyl, $C_{1-6}$ alkoxy or $C_{1-6}$ haloalkoxy), phenyl($C_{2-4}$)alkenyl, (wherein the phenyl group is optionally substituted by halo, nitro, cyano, $C_{1-6}$ alkyl, $C_{1-6}$ haloalkyl, $C_{1-6}$ alkoxy or $C_{1-6}$ haloalkoxy), heteroaryl (optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyl (wherein the heterocyclyl group is optionally substituted by halo, nitro, cyano, $C_{1-6}$ alkyl, $C_{1-6}$ haloalkyl, $C_{1-6}$ alkoxy or $C_{1-6}$ haloalkoxy), heteroaryl($C_{1-4}$)alkyl (wherein the heteroaryl group is optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyl($C_{1-4}$)alkyl (wherein the heterocyclyl group is optionally substituted by halo, nitro, cyano, $C_{1-6}$ alkyl, $C_{1-6}$ haloalkyl, $C_{1-6}$ alkoxy or $C_{1-6}$ haloalkoxy), $R^{15}O$, $C_{1-8}$ alkylthio, $R^{16}R^{17}N$ or $R^{18}ON=C(R^{19})$; where $R^{15}$ is $C_{1-8}$ alkyl, $C_{1-6}$ haloalkyl; $R^{19}$ is $C_{1-6}$ alkyl, $C_{1-6}$ haloalkyl or phenyl (optionally substituted by halo, nitro, cyano, $C_{1-6}$ alkyl, $C_{1-6}$ haloalkyl, $C_{1-6}$ alkoxy or $C_{1-6}$ haloalkoxy); $R^{16}$ and $R^{17}$ are, independently, hydrogen, $C_{1-8}$ alkyl, $C_{3-7}$ cycloalkyl, $C_{3-6}$ alkenyl, $C_{3-6}$ alkynyl, $C_{3-7}$ cycloalkyl ($C_{1-4}$)alkyl, $C_{2-6}$ haloalkyl, $C_{1-6}$ alkoxy($C_{1-6}$)alkyl, $C_{1-6}$ alkoxycarbonyl, or $R^{16}$ and $R^{17}$ together with the N atom to which they are attached form a five, six or seven-membered heterocyclic ring which may contain one or two further heteroatoms selected from O, N or S and which may be optionally substituted by one or two $C_{1-6}$ alkyl groups; and $R^{18}$ is $C_{1-6}$ alkyl or phenyl($C_{1-2}$)alkyl (wherein the phenyl group is optionally substituted by halo, nitro, cyano, $C_{1-6}$ alkyl, $C_{1-6}$ haloalkyl, $C_{1-6}$ alkoxy or $C_{1-6}$ haloalkoxy); and $R^7$ is more preferably $C_{1-8}$ alkyl, $C_{1-8}$ haloalkyl, $C_{1-8}$ cyanoalkyl, $C_{3-7}$ cycloalkyl, $C_{1-3}$ alkyl($C_{3-7}$)cycloalkyl, $C_{1-6}$ alkoxy($C_{1-6}$)alkyl, heterocyclyl (wherein the heterocylyl group is optionally substituted by halo, nitro, cyano, $C_{1-6}$ alkyl, $C_{1-6}$ haloalkyl, $C_{1-6}$ alkoxy or $C_{1-6}$ haloalkoxy) or $R16R^{17}N$; where $R^{16}$ and $R^{17}$ are, independently, $C_{1-8}$ alkyl or together with the N atom to which they are attached form a five, six or seven-membered heterocyclic ring which may contain one or two further heteroatoms selected from O, N or S and which may be optionally substituted by one or two $C_{1-6}$ alkyl groups.

It is further preferred that $R^7$ is $C_{1-8}$ alkyl, $C_{1-8}$ haloalkyl, $C_{1-8}$ cyanoalkyl, $C_{3-7}$ cycloalkyl($C_{1-6}$)alkyl, $C_{5-6}$ cycloalkenyl($C_{1-6}$)alkyl, $C_{1-6}$ alkoxy($C_{1-6}$)alkyl, $C_{3-6}$ alkenyloxy($C_{1-6}$)alkyl, $C_{3-6}$ alkynyloxy($C_{1-6}$)alkyl, aryloxy ($C_{1-6}$)alkyl, $C_{1-6}$ carboxyalkyl, $C_{1-6}$ alkylcarbonyl($C_{1-6}$) alkyl, $C_{2-6}$ alkenylcarbonyl($C_{1-6}$)alkyl, $C_{2-6}$ alkynylcarbonyl($C_{1-6}$)alkyl, $C_{1-6}$ alkoxycarbonyl($C_{1-6}$) alkyl, $C_{3-6}$ alkenyloxycarbonyl($C_{1-6}$)alkyl, $C_{3-6}$ alkynyloxycarbonyl-($C_{1-6}$)alkyl, aryloxycarbonyl($C_{1-6}$) alkyl, $C_{1-6}$ alkylthio($C_{1-6}$)alkyl, $C_{1-6}$ alkylsulfinyl($C_{1-6}$) alkyl, $C_{1-6}$ alkylsulfonyl($C_{1-6}$)alkyl, aminocarbonyl($C_{1-6}$) alkyl, $C_{1-6}$ alkylaminocarbonyl($C_{1-6}$)alkyl, di($C_{1-6}$) alkylaminocarbonyl($C_{1-6}$)alkyl, phenyl($C_{1-6}$)alkyl (wherein the phenyl group is optionally substituted by halo, nitro, cyano, $C_{1-6}$ alkyl, $C_{1-6}$ haloalkyl, $C_{1-6}$ alkoxy or $C_{1-6}$ haloalkoxy), heteroaryl($C_{1-4}$)alkyl (wherein the heteroaryl group is optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyl($C_{1-4}$)alkyl (wherein the heterocyclyl group is optionally substituted by halo, nitro, cyano, $C_{1-6}$ alkyl, $C_{1-6}$ haloalkyl, $C_{1-6}$ alkoxy or $C_{1-6}$ haloalkoxy), $C_{2-6}$ alkenyl, $C_{2-6}$ haloalkenyl, $C_{1-6}$ cyanoalkenyl, $C_{5-6}$ cycloalkenyl, aminocarbonyl($C_{2-6}$)alkenyl, $C_{1-6}$ alkylaminocarbonyl ($C_{1-6}$)alkenyl, di($C_{1-6}$)alkylaminocarbonyl($C_{1-6}$)alkenyl, phenyl($C_{2-4}$)alkenyl (wherein the phenyl group is optionally substituted by halo, nitro, cyano, $C_{1-6}$ alkyl, $C_{1-6}$ haloalkyl, $C_{1-6}$ alkoxy or $C_{1-6}$ haloalkoxy), $C_{2-6}$ alkynyl, aminocarbonyl($C_{2-6}$)alkynyl, alkylaminocarbonyl($C_{1-6}$) alkynyl, di($C_{1-6}$)alkylaminocarbonyl($C_{1-6}$)alkynyl, $C_{3-7}$ cycloalkyl, $C_{3-7}$ halocycloalkyl, $C_{3-7}$ cyanocycloalkyl, $C_{1-3}$ alkyl(C$_{3-7}$)cycloalkyl, C$_{1-3}$ alkyl(C$_{3-7}$)halocycloalkyl, phenyl (optionally substituted by halo, nitro, cyano, C$_{1-6}$ alkyl, C$_{1-6}$ haloalkyl, C$_{1-6}$ alkoxy or C$_{1-6}$ haloalkoxy), heteroaryl (optionally substituted by halo, nitro, cyano, C$_{1-6}$ alkyl, C$_{1-6}$ haloalkyl, C$_{1-6}$ alkoxy or C$_{1-6}$ haloalkoxy), heterocyclyl (optionally substituted by halo, nitro, cyano, C$_{1-6}$ alkyl, C$_{1-6}$ haloalkyl, C$_{1-6}$ alkoxy or C$_{1-6}$ haloalkoxy), C$_{1-8}$ alkylthio, R$^{15}$O, R$^{16}$R$^{17}$N or R$^{18}$ON=C(R$^{19}$); where R$^{15}$ is C$_{1-8}$ alkyl or C$_{1-6}$ haloalkyl; R$^{19}$ is phenyl (optionally substituted by halo, nitro, cyano, C$_{1-6}$ alkyl, C$_{1-6}$ haloalkyl, C$_{1-6}$ alkoxy or C$_{1-6}$ haloalkoxy), C$_{1-6}$ alkyl or C$_{1-6}$ haloalkyl; R$^{16}$ and R$^{17}$ are, independently, hydrogen, C$_{1-8}$ alkyl, C$_{3-7}$ cycloalkyl (C$_{1-4}$)alkyl, C$_{2-6}$ haloalkyl, C$_{1-6}$ alkoxy(C$_{1-6}$)alkyl, C$_{3-7}$ cycloalkyl, C$_{3-6}$ alkenyl, C$_{3-6}$ alkenyl or C$_{1-6}$ alkoxycarbonyl; and R$^{18}$ is phenyl(C$_{1-2}$)alkyl (wherein the phenyl group is optionally substituted by halo, nitro, cyano, C$_{1-6}$ alkyl, C$_{1-6}$ haloalkyl, C$_{1-6}$ alkoxy or C$_{1-6}$ haloalkoxy) or C$_{1-6}$ alkyl.

It is even more preferred that R$^7$ is C$_{1-8}$ alkyl, C$_{1-8}$ haloalkyl, C$_{1-8}$ cyanoalkyl, C$_{1-6}$ alkoxy (C$_{1-6}$) alkyl, C$_{3-7}$ cycloalkyl, C$_{1-3}$ alkyl (C$_{3-7}$) cycloalkyl, heterocyclyl (optionally substituted by halo, nitro, cyano, C$_{1-6}$ alkyl, C$_{1-6}$ haloalkyl C$_{1-6}$ alkoxy or C$_{1-6}$ haloalkoxy) or di(C$_{1-8}$) alkylamino.

It is yet more preferred that R$^7$ is C$_{1-8}$ alkyl, C$_{1-8}$ haloalkyl, C$_{1-8}$ cyanoalkyl, C$_{1-6}$ alkoxy (C$_{1-6}$) alkyl, C$_{3-7}$ cycloalkyl, C$_{1-3}$ alkyl (C$_{3-7}$) cycloalkyl, heterocyclyl (optionally substituted by C$_{1-6}$ alkyl) or di(C$_{1-8}$)alkylamino.

R$^7$ is most preferably C$_{1-8}$ alkyl, C$_{1-8}$ haloalkyl, C$_{1-8}$ cyanoalkyl, C$_{3-7}$ cycloalkyl, C$_{1-3}$ alkyl(C$_{3-7}$)cycloalkyl, C$_{1-6}$ alkoxy(C$_{1-6}$)alkyl or R$^{16}$R$^{17}$N; where R$^{16}$ and R$^{17}$ are, independently, C$_{1-8}$ alkyl or together with the N atom to which they are attached form a five, six or seven-membered heterocyclic ring which may contain one further heteroatom selected from O, N or S and which may be optionally substituted by one or two C$_{1-6}$ alkyl groups.

It is preferred that R$^8$ is hydrogen, halogen, nitro, cyano, C$_{1-8}$ alkyl, C$_{1-6}$ haloalkyl, C$_{1-6}$ cyanoalkyl, C$_{3-7}$ cycloalkyl (C$_{1-6}$)alkyl, C$_{1-6}$ alkoxy(C$_{1-6}$)alkyl, C$_{1-6}$ alkoxycarbonyl (C$_{1-6}$)alkyl, C$_{1-6}$ alkylcarbonyl(C$_{1-6}$)alkyl, C$_{1-6}$ alkylaminocarbonyl(C$_{1-6}$)alkyl, di(C$_{1-6}$)alkylaminocarbonyl(C$_{1-6}$)alkyl, phenyl(C$_{1-6}$)alkyl (wherein the phenyl group is optionally substituted by halo, nitro, cyano, C$_{1-6}$ alkyl, C$_{1-6}$ haloalkyl, C$_{1-6}$ alkoxy or C$_{1-6}$ haloalkoxy), heteroaryl(C$_{1-6}$)alkyl (wherein the heteroaryl group is optionally substituted by halo, nitro, cyano, C$_{1-6}$ alkyl, C$_{1-6}$ haloalkyl, C$_{1-6}$ alkoxy or C$_{1-6}$ haloalkoxy), C$_{2-6}$ alkenyl, C$_{2-6}$ haloalkenyl, C$_{2-6}$ alkynyl, C$_{3-7}$ cycloalkyl, C$_{1-6}$ alkoxycarbonyl, C$_{1-6}$ alkylcarbonyl, C$_{1-6}$ alkylaminocarbonyl, di(C$_{1-6}$)alkylaminocarbonyl, phenyl (optionally substituted by halo, nitro, cyano, C$_{1-6}$ alkyl, C$_{1-6}$ haloalkyl, C$_{1-6}$ alkoxy or C$_{1-6}$ haloalkoxy) or heteroaryl (optionally substituted by halo, nitro, cyano, C$_{1-6}$ alkyl, C$_{1-6}$ haloalkyl, C$_{1-6}$ alkoxy or C$_{1-6}$ haloalkoxy).

It is more preferred that R$^8$ is hydrogen, halogen, C$_{1-8}$ alkyl or C$_{1-6}$ haloalkyl.

It is preferred that R$^9$ is cyano, nitro, C$_{1-6}$ alkyl, C$_{1-6}$ haloalkyl, C$_{3-7}$ cycloalkyl(C$_{1-6}$)alkyl, C$_{3-7}$ cycloalkyl, CH$_2$(C$_{2-6}$)alkenyl, CH$_2$(C$_{2-6}$)alkynyl, phenyl (optionally substituted by halo, nitro, cyano, C$_{1-6}$ alkyl, C$_{1-6}$ haloalkyl, C$_{1-6}$ alkoxy or C$_{1-6}$ haloalkoxy), heteroaryl (optionally substituted by halo, nitro, cyano, C$_{1-6}$ alkyl, C$_{1-6}$ haloalkyl, C$_{1-6}$ alkoxy or C$_{1-6}$ haloalkoxy), C$_{1-6}$ alkylcarbonyl, C$_{1-6}$ alkoxycarbonyl, C$_{1-6}$ alkylamino, di(C$_{1-6}$)alkylamino, C$_{1-6}$ alkylcarbonylamino, C$_{1-6}$ alkoxycarbonylamino, C$_{1-6}$ alkoxy, C$_{1-6}$ alkylthio, C$_{1-6}$ haloalkylthio, C$_{1-6}$ alkylsulfinyl, C$_{1-6}$ haloalkylsulfinyl, C$_{1-6}$ alkylsulfonyl, C$_{1-6}$ haloalkylsulfonyl, arylthio, arylsulfinyl, arylsulfonyl or (C$_{1-6}$)alkylcarbonyloxy.

It is preferred that R$^{10}$ is hydrogen, C$_{1-8}$ alkyl, C$_{1-6}$ haloalkyl, C$_{1-6}$ cyanoalkyl, C$_{2-6}$ alkenyl, C$_{2-6}$ haloalkenyl, C$_{2-6}$ alkynyl, C$_{3-7}$ cycloalkyl, C$_{3-7}$ cycloalkyl(C$_{1-6}$)alkyl, C$_{1-6}$ alkoxy(C$_{1-6}$)alkyl, C$_{1-6}$ alkoxycarbonyl, C$_{1-6}$ alkylcarbonyl, C$_{1-6}$ alkylaminocarbonyl, di(C$_{1-6}$) alkylaminocarbonyl, phenyl (optionally substituted by halo, nitro, cyano, C$_{1-6}$ alkyl, C$_{1-6}$ haloalkyl, C$_{1-6}$ alkoxy or C$_{1-6}$ haloalkoxy) or heteroaryl (optionally substituted by halo, nitro, cyano, C$_{1-6}$ alkyl, C$_{1-6}$ haloalkyl, C$_{1-6}$ alkoxy or C$_{1-6}$ haloalkoxy).

It is more preferred that R$^{10}$ is hydrogen, C$_{1-8}$ alkyl or C$_{1-6}$ haloalkyl.

The compounds in Tables 1–102 illustrate compounds of the invention.

Table 1 provides 160 compounds of formula (1)

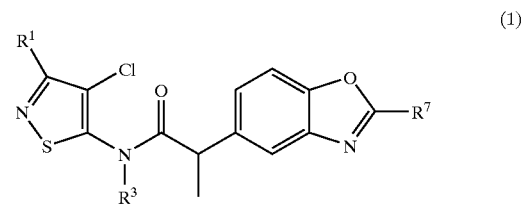

(1)

wherein R$^1$, R$^3$ and R$^7$ are defined in Table 1.

TABLE 1

| Compound No. | R$^1$ | R$^3$ | R$^7$ |
|---|---|---|---|
| 1 | CH$_3$ | H | CH$_3$ |
| 2 | CH$_3$ | H | CH$_2$CH$_3$ |
| 3 | CH$_3$ | H | CH$_2$CH$_2$CH$_3$ |
| 4 | CH$_3$ | H | CH(CH$_3$)$_2$ |
| 5 | CH$_3$ | H | C(CH$_3$)$_3$ |
| 6 | CH$_3$ | H | CH$_2$CH(CH$_3$)$_2$ |
| 7 | CH$_3$ | H | CH$_2$C(CH$_3$)$_3$ |
| 8 | CH$_3$ | H | CH$_2$CF$_3$ |
| 9 | CH$_3$ | H | CF$_2$CF$_3$ |
| 10 | CH$_3$ | H | CF$_2$CF$_2$CF$_3$ |
| 11 | CH$_3$ | CH$_3$ | CH$_3$ |
| 12 | CH$_3$ | CH$_3$ | CH$_2$CH$_3$ |
| 13 | CH$_3$ | CH$_3$ | CH$_2$CH$_2$CH$_3$ |
| 14 | CH$_3$ | CH$_3$ | CH(CH$_3$)$_2$ |
| 15 | CH$_3$ | CH$_3$ | C(CH$_3$)$_3$ |
| 16 | CH$_3$ | CH$_3$ | CH$_2$CH(CH$_3$)$_2$ |
| 17 | CH$_3$ | CH$_3$ | CH$_2$C(CH$_3$)$_3$ |
| 18 | CH$_3$ | CH$_3$ | CH$_2$CF$_3$ |
| 19 | CH$_3$ | CH$_3$ | CF$_2$CF$_3$ |
| 20 | CH$_3$ | CH$_3$ | CF$_2$CF$_2$CF$_3$ |
| 21 | CH$_3$ | CH$_2$CH$_3$ | CH$_3$ |
| 22 | CH$_3$ | CH$_2$CH$_3$ | CH$_2$CH$_3$ |
| 23 | CH$_3$ | CH$_2$CH$_3$ | CH$_2$CH$_2$CH$_3$ |
| 24 | CH$_3$ | CH$_2$CH$_3$ | CH(CH$_3$)$_2$ |
| 25 | CH$_3$ | CH$_2$CH$_3$ | C(CH$_3$)$_3$ |
| 26 | CH$_3$ | CH$_2$CH$_3$ | CH$_2$CH(CH$_3$)$_2$ |
| 27 | CH$_3$ | CH$_2$CH$_3$ | CH$_2$C(CH$_3$)$_3$ |
| 28 | CH$_3$ | CH$_2$CH$_3$ | CH$_2$CF$_3$ |
| 29 | CH$_3$ | CH$_2$CH$_3$ | CF$_2$CF$_3$ |
| 30 | CH$_3$ | CH$_2$CH$_3$ | CF$_2$CF$_2$CF$_3$ |
| 31 | CH$_3$ | CH$_2$CH$_2$CH$_3$ | CH$_3$ |
| 32 | CH$_3$ | CH$_2$CH$_2$CH$_3$ | CH$_2$CH$_3$ |
| 33 | CH$_3$ | CH$_2$CH$_2$CH$_3$ | CH$_2$CH$_2$CH$_3$ |
| 34 | CH$_3$ | CH$_2$CH$_2$CH$_3$ | CH(CH$_3$)$_2$ |
| 35 | CH$_3$ | CH$_2$CH$_2$CH$_3$ | C(CH$_3$)$_3$ |
| 36 | CH$_3$ | CH$_2$CH$_2$CH$_3$ | CH$_2$CH(CH$_3$)$_2$ |
| 37 | CH$_3$ | CH$_2$CH$_2$CH$_3$ | CH$_2$C(CH$_3$)$_3$ |
| 38 | CH$_3$ | CH$_2$CH$_2$CH$_3$ | CH$_2$CF$_3$ |
| 39 | CH$_3$ | CH$_2$CH$_2$CH$_3$ | CF$_2$CF$_3$ |
| 40 | CH$_3$ | CH$_2$CH$_2$CH$_3$ | CF$_2$CF$_2$CF$_3$ |
| 41 | CH$_3$ | CH$_2$CH=CH$_2$ | CH$_3$ |
| 42 | CH$_3$ | CH$_2$CH=CH$_2$ | CH$_2$CH$_3$ |
| 43 | CH$_3$ | CH$_2$CH=CH$_2$ | CH$_2$CH$_2$CH$_3$ |
| 44 | CH$_3$ | CH$_2$CH=CH$_2$ | CH(CH$_3$)$_2$ |

TABLE 1-continued

| Compound No. | R¹ | R³ | R⁷ |
|---|---|---|---|
| 45 | CH₃ | CH₂CH=CH₂ | C(CH₃)₃ |
| 46 | CH₃ | CH₂CH=CH₂ | CH₂CH(CH₃)₂ |
| 47 | CH₃ | CH₂CH=CH₂ | CH₂C(CH₃)₃ |
| 48 | CH₃ | CH₂CH=CH₂ | CH₂CF₃ |
| 49 | CH₃ | CH₂CH=CH₂ | CF₂CF₃ |
| 50 | CH₃ | CH₂CH=CH₂ | CF₂CF₂CF₃ |
| 51 | CH₃ | CH₂C.CH | CH₃ |
| 52 | CH₃ | CH₂C.CH | CH₂CH₃ |
| 53 | CH₃ | CH₂C.CH | CH₂CH₂CH₃ |
| 54 | CH₃ | CH₂C.CH | CH(CH₃)₂ |
| 55 | CH₃ | CH₂C.CH | C(CH₃)₃ |
| 56 | CH₃ | CH₂C.CH | CH₂CH(CH₃)₂ |
| 57 | CH₃ | CH₂C.CH | CH₂C(CH₃)₃ |
| 58 | CH₃ | CH₂C.CH | CH₂CF₃ |
| 59 | CH₃ | CH₂C.CH | CF₂CF₃ |
| 60 | CH₃ | CH₂C.CH | CF₂CF₂CF₃ |
| 61 | CH₃ | CH₂OCH₃ | CH₃ |
| 62 | CH₃ | CH₂OCH₃ | CH₂CH₃ |
| 63 | CH₃ | CH₂OCH₃ | CH₂CH₂CH₃ |
| 64 | CH₃ | CH₂OCH₃ | CH(CH₃)₂ |
| 65 | CH₃ | CH₂OCH₃ | C(CH₃)₃ |
| 66 | CH₃ | CH₂OCH₃ | CH₂CH(CH₃)₂ |
| 67 | CH₃ | CH₂OCH₃ | CH₂C(CH₃)₃ |
| 68 | CH₃ | CH₂OCH₃ | CH₂CF₃ |
| 69 | CH₃ | CH₂OCH₃ | CF₂CF₃ |
| 70 | CH₃ | CH₂OCH₃ | CF₂CF₂CF₃ |
| 71 | CH₃ | CH₂OCH₂CH₃ | CH₃ |
| 72 | CH₃ | CH₂OCH₂CH₃ | CH₂CH₃ |
| 73 | CH₃ | CH₂OCH₂CH₃ | CH₂CH₂CH₃ |
| 74 | CH₃ | CH₂OCH₂CH₃ | CH(CH₃)₂ |
| 75 | CH₃ | CH₂OCH₂CH₃ | C(CH₃)₃ |
| 76 | CH₃ | CH₂OCH₂CH₃ | CH₂CH(CH₃)₂ |
| 77 | CH₃ | CH₂OCH₂CH₃ | CH₂C(CH₃)₃ |
| 78 | CH₃ | CH₂OCH₂CH₃ | CH₂CF₃ |
| 79 | CH₃ | CH₂OCH₂CH₃ | CF₂CF₃ |
| 80 | CH₃ | CH₂OCH₂CH₃ | CF₂CF₂CF₃ |
| 81 | CH₂CH₃ | H | CH₃ |
| 82 | CH₂CH₃ | H | CH₂CH₃ |
| 83 | CH₂CH₃ | H | CH₂CH₂CH₃ |
| 84 | CH₂CH₃ | H | CH(CH₃)₂ |
| 85 | CH₂CH₃ | H | C(CH₃)₃ |
| 86 | CH₂CH₃ | H | CH₂CH(CH₃)₂ |
| 87 | CH₂CH₃ | H | CH₂C(CH₃)₃ |
| 88 | CH₂CH₃ | H | CH₂CF₃ |
| 89 | CH₂CH₃ | H | CF₂CF₃ |
| 90 | CH₂CH₃ | H | CF₂CF₂CF₃ |
| 91 | CH₂CH₃ | CH₃ | CH₃ |
| 92 | CH₂CH₃ | CH₃ | CH₂CH₃ |
| 93 | CH₂CH₃ | CH₃ | CH₂CH₂CH₃ |
| 94 | CH₂CH₃ | CH₃ | CH(CH₃)₂ |
| 95 | CH₂CH₃ | CH₃ | C(CH₃)₃ |
| 96 | CH₂CH₃ | CH₃ | CH₂CH(CH₃)₂ |
| 97 | CH₂CH₃ | CH₃ | CH₂C(CH₃)₃ |
| 98 | CH₂CH₃ | CH₃ | CH₂CF₃ |
| 99 | CH₂CH₃ | CH₃ | CF₂CF₃ |
| 100 | CH₂CH₃ | CH₃ | CF₂CF₂CF₃ |
| 101 | CH₂CH₃ | CH₂CH₃ | CH₃ |
| 102 | CH₂CH₃ | CH₂CH₃ | CH₂CH₃ |
| 103 | CH₂CH₃ | CH₂CH₃ | CH₂CH₂CH₃ |
| 104 | CH₂CH₃ | CH₂CH₃ | CH(CH₃)₂ |
| 105 | CH₂CH₃ | CH₂CH₃ | C(CH₃)₃ |
| 106 | CH₂CH₃ | CH₂CH₃ | CH₂CH(CH₃)₂ |
| 107 | CH₂CH₃ | CH₂CH₃ | CH₂C(CH₃)₃ |
| 108 | CH₂CH₃ | CH₂CH₃ | CH₂CF₃ |
| 109 | CH₂CH₃ | CH₂CH₃ | CF₂CF₃ |
| 110 | CH₂CH₃ | CH₂CH₃ | CF₂CF₂CF₃ |
| 111 | CH₂CH₃ | CH₂CH₂CH₃ | CH₃ |
| 112 | CH₂CH₃ | CH₂CH₂CH₃ | CH₂CH₃ |
| 113 | CH₂CH₃ | CH₂CH₂CH₃ | CH₂CH₂CH₃ |
| 114 | CH₂CH₃ | CH₂CH₂CH₃ | CH(CH₃)₂ |
| 115 | CH₂CH₃ | CH₂CH₂CH₃ | C(CH₃)₃ |
| 116 | CH₂CH₃ | CH₂CH₂CH₃ | CH₂CH(CH₃)₂ |
| 117 | CH₂CH₃ | CH₂CH₂CH₃ | CH₂C(CH₃)₃ |
| 118 | CH₂CH₃ | CH₂CH₂CH₃ | CH₂CF₃ |
| 119 | CH₂CH₃ | CH₂CH₂CH₃ | CF₂CF₃ |
| 120 | CH₂CH₃ | CH₂CH₂CH₃ | CF₂CF₂CF₃ |
| 121 | CH₂CH₃ | CH₂CH=CH₂ | CH₃ |
| 122 | CH₂CH₃ | CH₂CH=CH₂ | CH₂CH₃ |
| 123 | CH₂CH₃ | CH₂CH=CH₂ | CH₂CH₂CH₃ |
| 124 | CH₂CH₃ | CH₂CH=CH₂ | CH(CH₃)₂ |
| 125 | CH₂CH₃ | CH₂CH=CH₂ | C(CH₃)₃ |
| 126 | CH₂CH₃ | CH₂CH=CH₂ | CH₂CH(CH₃)₂ |
| 127 | CH₂CH₃ | CH₂CH=CH₂ | CH₂C(CH₃)₃ |
| 128 | CH₂CH₃ | CH₂CH=CH₂ | CH₂CF₃ |
| 129 | CH₂CH₃ | CH₂CH=CH₂ | CF₂CF₃ |
| 130 | CH₂CH₃ | CH₂CH=CH₂ | CF₂CF₂CF₃ |
| 131 | CH₂CH₃ | CH₂C.CH | CH₃ |
| 132 | CH₂CH₃ | CH₂C.CH | CH₂CH₃ |
| 133 | CH₂CH₃ | CH₂C.CH | CH₂CH₂CH₃ |
| 134 | CH₂CH₃ | CH₂C.CH | CH(CH₃)₂ |
| 135 | CH₂CH₃ | CH₂C.CH | C(CH₃)₃ |
| 136 | CH₂CH₃ | CH₂C.CH | CH₂CH(CH₃)₂ |
| 137 | CH₂CH₃ | CH₂C.CH | CH₂C(CH₃)₃ |
| 138 | CH₂CH₃ | CH₂C.CH | CH₂CF₃ |
| 139 | CH₂CH₃ | CH₂C.CH | CF₂CF₃ |
| 140 | CH₂CH₃ | CH₂C.CH | CF₂CF₂CF₃ |
| 141 | CH₂CH₃ | CH₂OCH₃ | CH₃ |
| 142 | CH₂CH₃ | CH₂OCH₃ | CH₂CH₃ |
| 143 | CH₂CH₃ | CH₂OCH₃ | CH₂CH₂CH₃ |
| 144 | CH₂CH₃ | CH₂OCH₃ | CH(CH₃)₂ |
| 145 | CH₂CH₃ | CH₂OCH₃ | C(CH₃)₃ |
| 146 | CH₂CH₃ | CH₂OCH₃ | CH₂CH(CH₃)₂ |
| 147 | CH₂CH₃ | CH₂OCH₃ | CH₂C(CH₃)₃ |
| 148 | CH₂CH₃ | CH₂OCH₃ | CH₂CF₃ |
| 149 | CH₂CH₃ | CH₂OCH₃ | CF₂CF₃ |
| 150 | CH₂CH₃ | CH₂OCH₃ | CF₂CF₂CF₃ |
| 151 | CH₂CH₃ | CH₂OCH₂CH₃ | CH₃ |
| 152 | CH₂CH₃ | CH₂OCH₂CH₃ | CH₂CH₃ |
| 153 | CH₂CH₃ | CH₂OCH₂CH₃ | CH₂CH₂CH₃ |
| 154 | CH₂CH₃ | CH₂OCH₂CH₃ | CH(CH₃)₂ |
| 155 | CH₂CH₃ | CH₂OCH₂CH₃ | C(CH₃)₃ |
| 156 | CH₂CH₃ | CH₂OCH₂CH₃ | CH₂CH(CH₃)₂ |
| 157 | CH₂CH₃ | CH₂OCH₂CH₃ | CH₂C(CH₃)₃ |
| 158 | CH₂CH₃ | CH₂OCH₂CH₃ | CH₂CF₃ |
| 159 | CH₂CH₃ | CH₂OCH₂CH₃ | CF₂CF₃ |
| 160 | CH₂CH₃ | CH₂OCH₂CH₃ | CF₂CF₂CF₃ |

TABLE 2

Table 2 provides 160 compounds of formula (2)

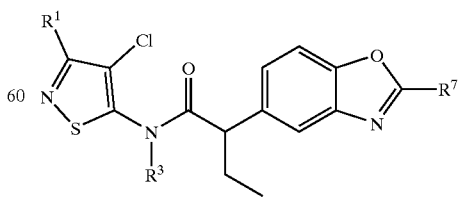

(2)

wherein R¹, R³ and R⁷ are as defined in Table 1.

TABLE 3

Table 3 provides 160 compounds of formula (3)

(3)

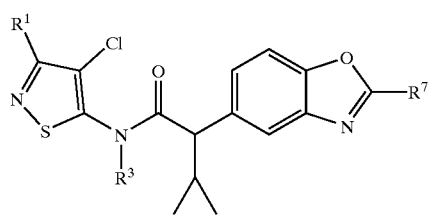

wherein $R^1$, $R^3$ and $R^7$ are as defined in Table 1.

TABLE 4

Table 4 provides 160 compounds of formula (4)

(4)

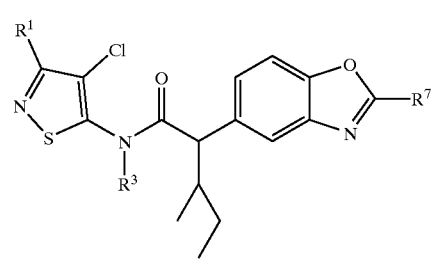

wherein $R^1$, $R^3$ and $R^7$ are as defined in Table 1.

TABLE 5

Table 5 provides 160 compounds of formula (5)

(5)

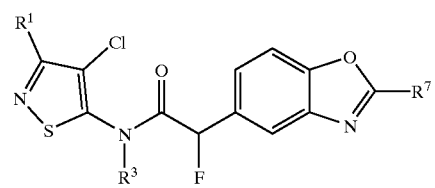

wherein $R^1$, $R^3$ and $R^7$ are as defined in Table 1.

TABLE 6

Table 6 provides 160 compounds of formula (6)

(6)

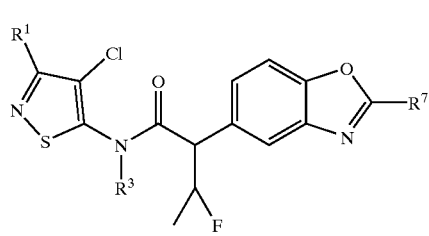

wherein $R^1$, $R^3$ and $R^7$ are as defined in Table 1.

TABLE 7

Table 7 provides 160 compounds of formula (7)

(7)

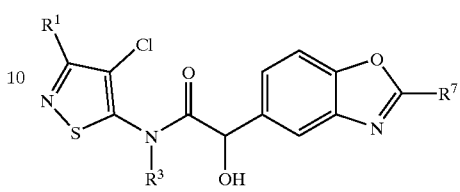

wherein $R^1$, $R^3$ and $R^7$ are as defined in Table 1.

TABLE 8

Table 8 provides 160 compounds of formula (8)

(8)

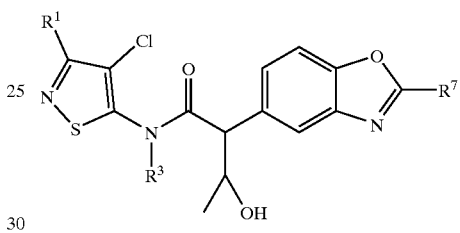

wherein $R^1$, $R^3$ and $R^7$ are as defined in Table 1.

TABLE 9

Table 9 provides 160 compounds of formula (9)

(9)

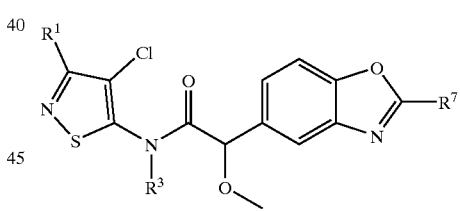

wherein $R^1$, $R^3$ and $R^7$ are as defined in Table 1.

TABLE 10

Table 10 provides 160 compounds of formula (10)

(10)

wherein $R^1$, $R^3$ and $R^7$ are as defined in Table 1.

TABLE 11

Table 11 provides 160 compounds of formula (11)

(11)

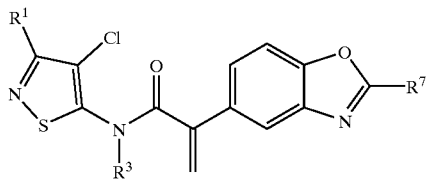

wherein R¹, R³ and R⁷ are as defined in Table 1.

TABLE 12

Table 12 provides 160 compounds of formula (12)

(12)

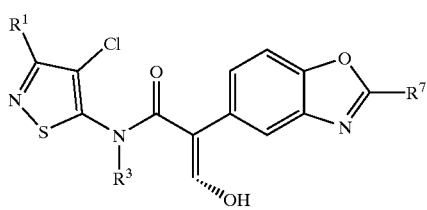

wherein R¹, R³ and R⁷ are as defined in Table 1.

TABLE 13

Table 13 provides 160 compounds of formula (13)

(13)

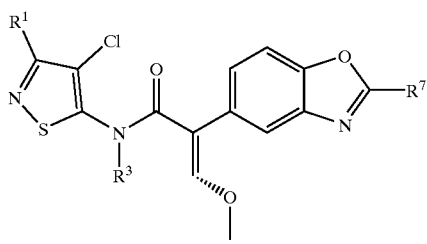

wherein R¹, R³ and R⁷ are as defined in Table 1.

TABLE 14

Table 14 provides 160 compounds of formula (14)

(14)

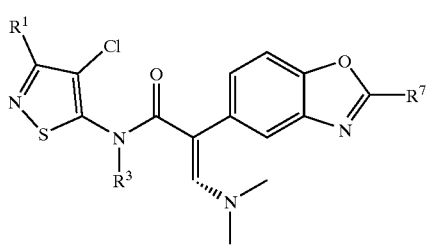

wherein R¹, R³ and R⁷ are as defined in Table 1.

TABLE 15

Table 15 provides 160 compounds of formula (15)

(15)

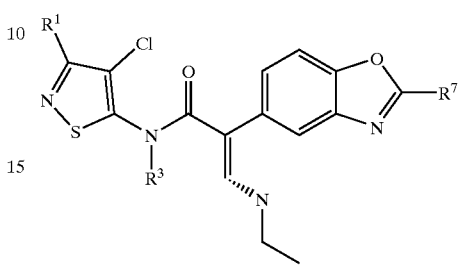

wherein R¹, R³ and R⁷ are as defined in Table 1.

TABLE 16

Table 16 provides 160 compounds of formula (16)

(16)

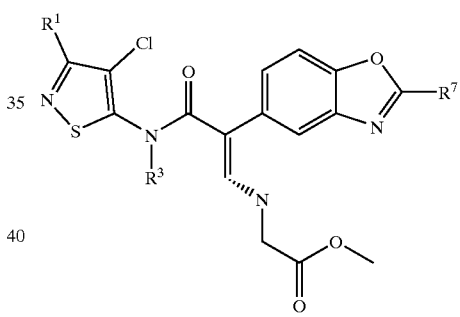

wherein R¹, R³ and R⁷ are as defined in Table 1.

TABLE 17

Table 17 provides 160 compounds of formula (17)

(17)

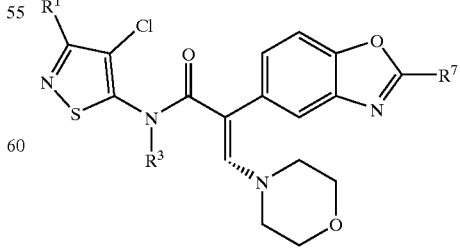

wherein R¹, R³ and R⁷ are as defined in Table 1.

TABLE 18

Table 18 provides 160 compounds of formula (18)

(18)

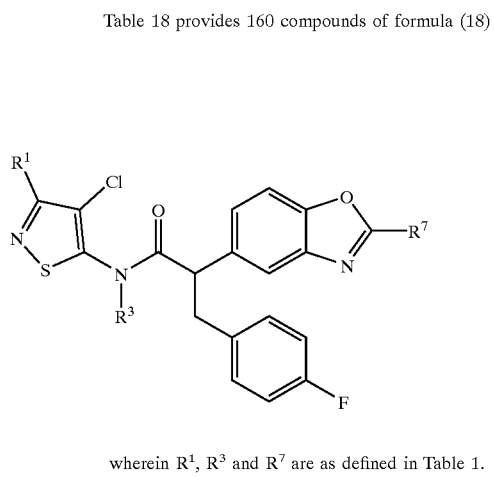

wherein $R^1$, $R^3$ and $R^7$ are as defined in Table 1.

TABLE 19

Table 19 provides 160 compounds of formula (19)

(19)

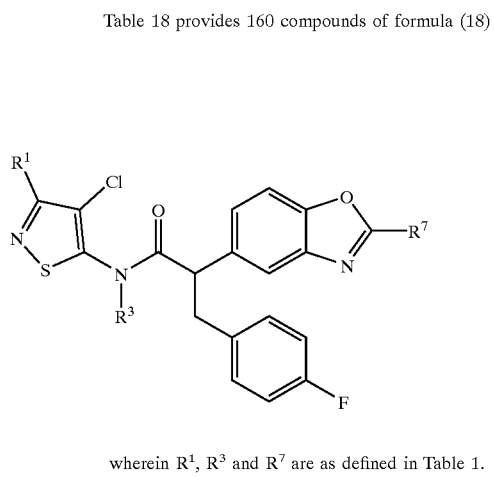

wherein $R^1$, $R^3$ and $R^7$ are as defined in Table 1.

TABLE 20

Table 20 provides 160 compounds of formula (20)

(20)

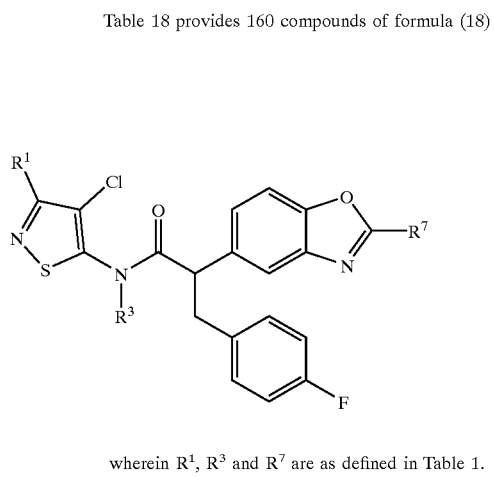

wherein $R^1$, $R^3$ and $R^7$ are as defined in Table 1.

TABLE 21

Table 21 provides 160 compounds of formula (21)

(21)

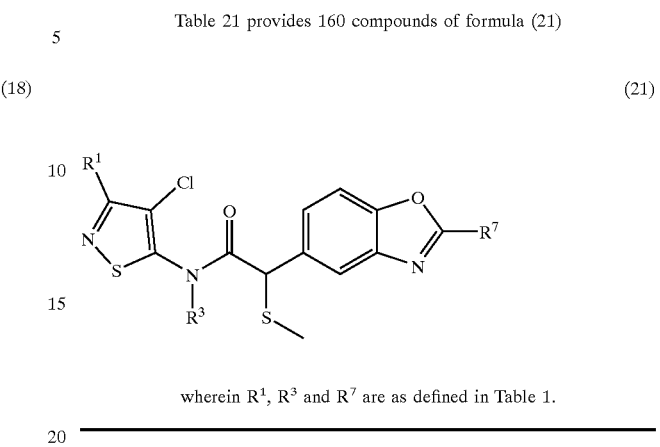

wherein $R^1$, $R^3$ and $R^7$ are as defined in Table 1.

TABLE 22

Table 22 provides 160 compounds of formula (22)

(22)

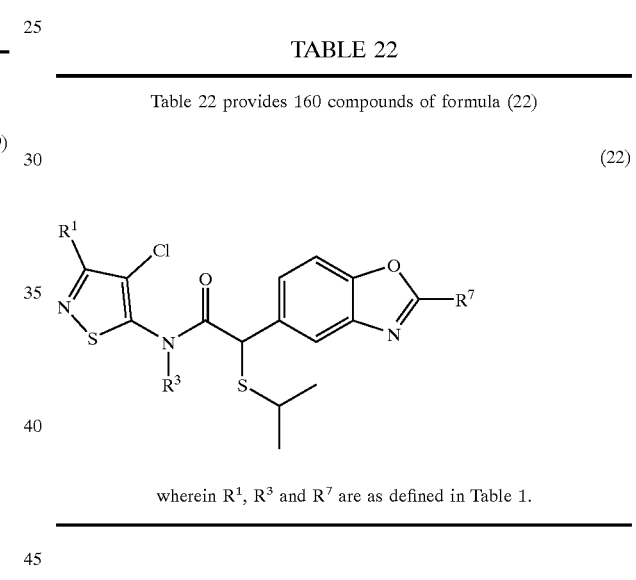

wherein $R^1$, $R^3$ and $R^7$ are as defined in Table 1.

TABLE 23

Table 23 provides 160 compounds of formula (23)

(23)

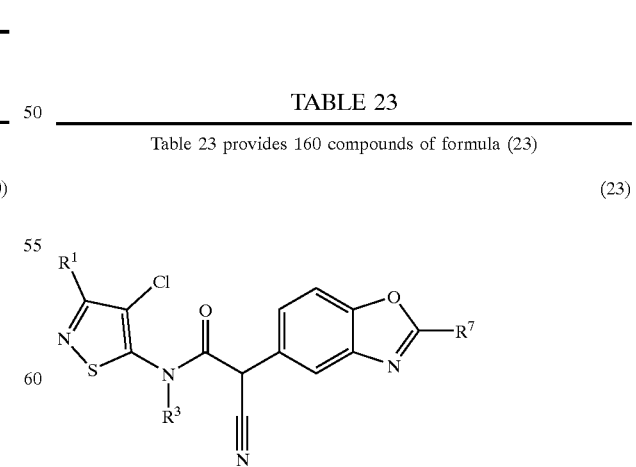

wherein $R^1$, $R^3$ and $R^7$ are as defined in Table 1.

TABLE 24

Table 24 provides 160 compounds of formula (24)

(24)

wherein R¹, R³ and R⁷ are as defined in Table 1.

TABLE 25

Table 25 provides 160 compounds of formula (25)

(25)

wherein R¹, R³ and R⁷ are as defined in Table 1.

TABLE 26

Table 26 provides 160 compounds of formula (26)

(26)

wherein R¹, R³ and R⁷ are as defined in Table 1.

TABLE 27

Table 27 provides 160 compounds of formula (27)

(27)

wherein R¹, R³ and R⁷ are as defined in Table 1.

TABLE 28

Table 28 provides 160 compounds of formula (28)

(28)

wherein R¹, R³ and R⁷ are as defined in Table 1.

TABLE 29

Table 29 provides 160 compounds of formula (29)

(29)

TABLE 30

Table 30 provides 160 compounds of formula (30)

(30)

wherein R$^1$, R$^3$ and R$^7$ are as defined in Table 1.

TABLE 31

Table 31 provides 160 compounds of formula (31)

(31)

wherein R$^1$, R$^3$ and R$^7$ are as defined in Table 1.

TABLE 32

Table 32 provides 160 compounds of formula (32)

(32)

wherein R$^1$, R$^3$ and R$^7$ are as defined in Table 1.

TABLE 33

Table 33 provides 160 compounds of formula (33)

(33)

wherein R$^1$, R$^3$ and R$^7$ are as defined in Table 1.

TABLE 34

Table 34 provides 160 compounds of formula (34)

(34)

wherein R$^1$, R$^3$ and R$^7$ are as defined in Table 1.

TABLE 35

Table 35 provides 160 compounds of formula (35)

(35)

wherein R$^1$, R$^3$ and R$^7$ are as defined in Table 1.

TABLE 36

Table 36 provides 160 compounds of formula (36)

(36)

wherein R$^1$, R$^3$ and R$^7$ are as defined in Table 1.

TABLE 37

Table 37 provides 160 compounds of formula (37)

(37)

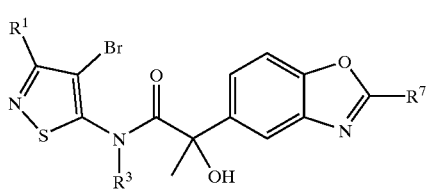

wherein R¹, R³ and R⁷ are as defined in Table 1.

TABLE 38

Table 38 provides 160 compounds of formula (38)

(38)

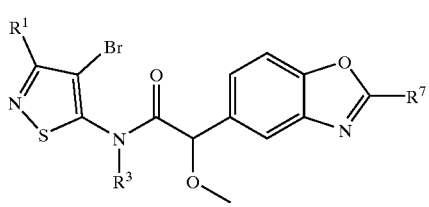

wherein R¹, R³ and R⁷ are as defined in Table 1.

TABLE 39

Table 39 provides 160 compounds of formula (39)

(39)

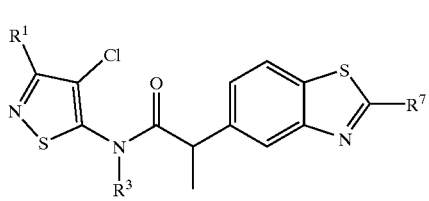

wherein R¹, R³ and R⁷ are as defined in Table 1.

TABLE 40

Table 40 provides 160 compounds of formula (40)

(40)

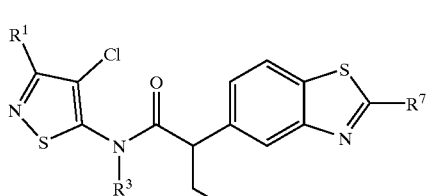

wherein R¹, R³ and R⁷ are as defined in Table 1.

TABLE 41

Table 41 provides 160 compounds of formula (41)

(41)

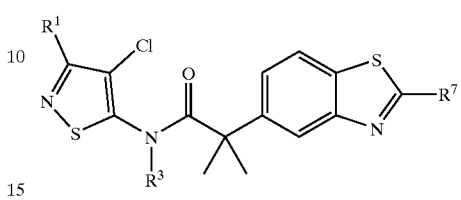

wherein R¹, R³ and R⁷ are as defined in Table 1.

TABLE 42

Table 42 provides 160 compounds of formula (42)

(42)

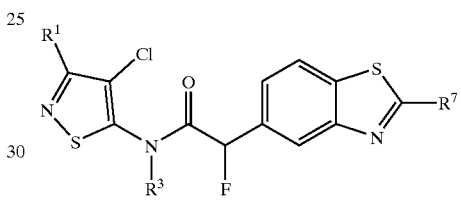

wherein R¹, R³ and R⁷ are as defined in Table 1.

TABLE 43

Table 43 provides 160 compounds of formula (43)

(43)

wherein R¹, R³ and R⁷ are as defined in Table 1.

TABLE 44

Table 44 provides 160 compounds of formula (44)

(44)

wherein R¹, R³ and R⁷ are as defined in Table 1.

TABLE 45

Table 45 provides 160 compounds of formula (45)

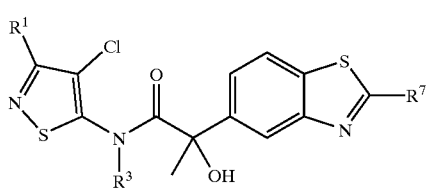
(45)

wherein R¹, R³ and R⁷ are as defined in Table 1.

TABLE 46

Table 46 provides 160 compounds of formula (46)

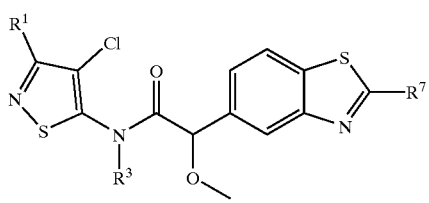
(46)

wherein R¹, R³ and R⁷ are as defined in Table 1.

TABLE 47

Table 47 provides 160 compounds of formula (47)

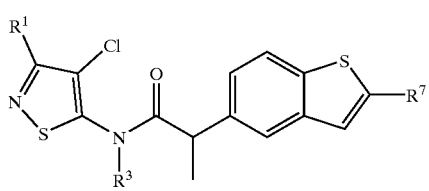
(47)

wherein R¹, R³ and R⁷ are as defined in Table 1.

TABLE 48

Table 48 provides 160 compounds of formula (48)

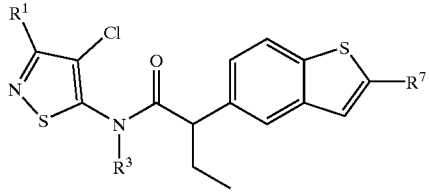
(48)

wherein R¹, R³ and R⁷ are as defined in Table 1.

TABLE 49

Table 49 provides 160 compounds of formula (49)

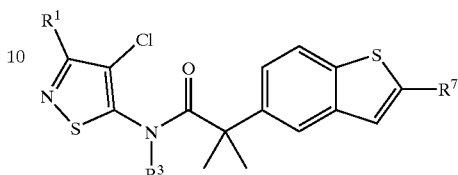
(49)

wherein R¹, R³ and R⁷ are as defined in Table 1.

TABLE 50

Table 50 provides 160 compounds of formula (50)

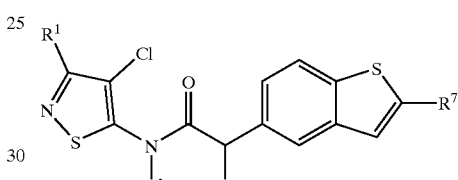
(50)

wherein R¹, R³ and R⁷ are as defined in Table 1.

TABLE 51

Table 51 provides 160 compounds of formula (51)

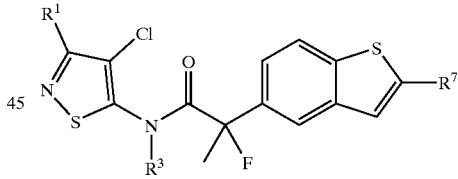
(51)

wherein R¹, R³ and R⁷ are as defined in Table 1.

TABLE 52

Table 52 provides 160 compounds of formula (52)

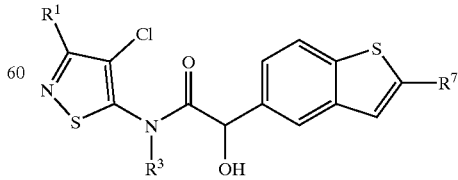
(52)

wherein R¹, R³ and R⁷ are as defined in Table 1.

TABLE 53

Table 53 provides 160 compounds of formula (53)

(53)

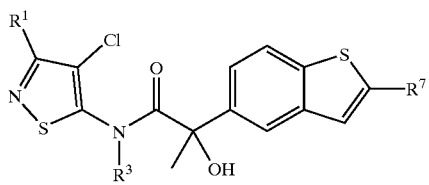

wherein R¹, R³ and R⁷ are as defined in Table 1.

TABLE 54

Table 54 provides 160 compounds of formula (54)

(54)

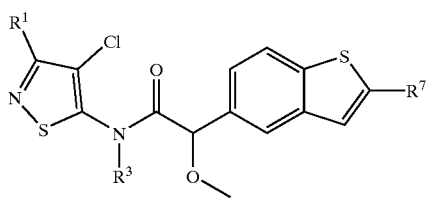

wherein R¹, R³ and R⁷ are as defined in Table 1.

TABLE 55

Table 55 provides 160 compounds of formula (55)

(55)

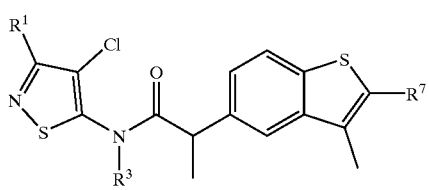

wherein R¹, R³ and R⁷ are as defined in Table 1.

TABLE 56

Table 56 provides 160 compounds of formula (56)

(56)

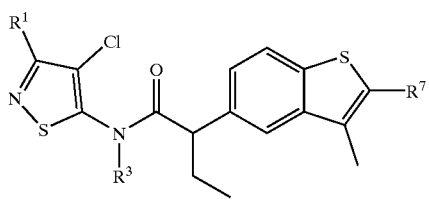

wherein R¹, R³ and R⁷ are as defined in Table 1.

TABLE 57

Table 57 provides 160 compounds of formula (57)

(57)

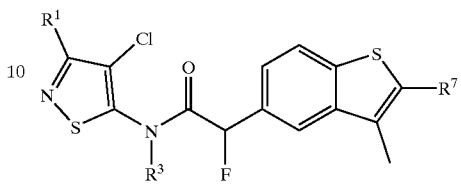

wherein R¹, R³ and R⁷ are as defined in Table 1.

TABLE 58

Table 58 provides 160 compounds of formula (58)

(58)

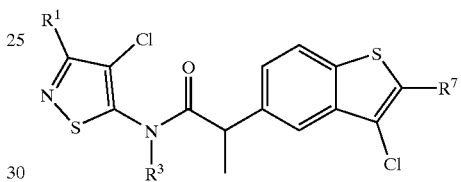

wherein R¹, R³ and R⁷ are as defined in Table 1.

TABLE 59

Table 59 provides 160 compounds of formula (59)

(59)

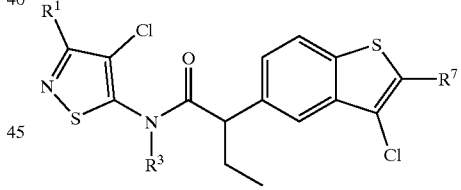

wherein R¹, R³ and R⁷ are as defined in Table 1.

TABLE 60

Table 60 provides 160 compounds of formula (60)

(60)

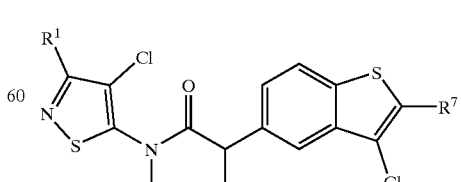

wherein R¹, R³ and R⁷ are as defined in Table 1.

TABLE 61

Table 61 provides 160 compounds of formula (61)

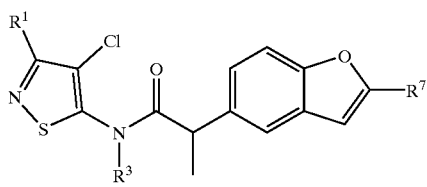
(61)

wherein R¹, R³ and R⁷ are as defined in Table 1.

TABLE 62

Table 62 provides 160 compounds of formula (62)

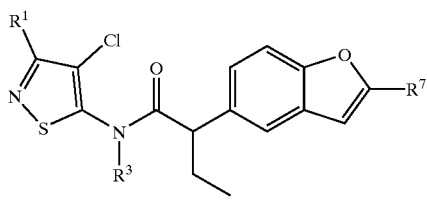
(62)

wherein R¹, R³ and R⁷ are as defined in Table 1.

TABLE 63

Table 63 provides 160 compounds of formula (63)

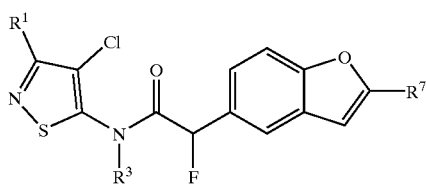
(63)

wherein R¹, R³ and R⁷ are as defined in Table 1.

TABLE 64

Table 64 provides 160 compounds of formula (64)

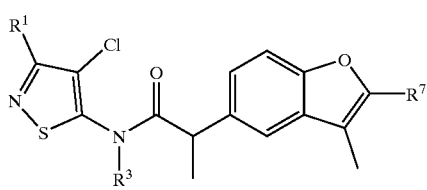
(64)

wherein R¹, R³ and R⁷ are as defined in Table 1.

TABLE 65

Table 65 provides 160 compounds of formula (65)

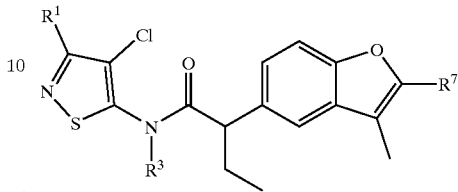
(65)

wherein R¹, R³ and R⁷ are as defined in Table 1.

TABLE 66

Table 66 provides 160 compounds of formula (66)

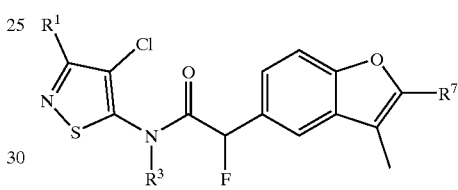
(66)

wherein R¹, R³ and R⁷ are as defined in Table 1.

TABLE 67

Table 67 provides 160 compounds of formula (67)

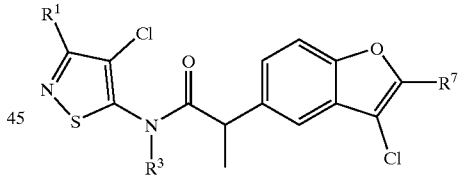
(67)

wherein R¹, R³ and R⁷ are as defined in Table 1.

TABLE 68

Table 68 provides 160 compounds of formula (68)

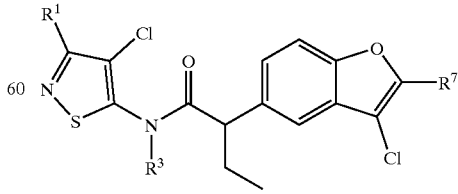
(68)

wherein R¹, R³ and R⁷ are as defined in Table 1.

TABLE 69

Table 69 provides 160 compounds of formula (69)

(69)

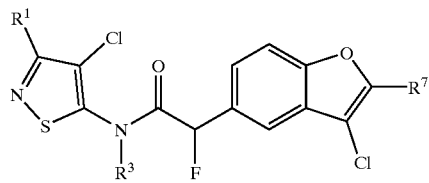

wherein R¹, R³ and R⁷ are as defined in Table 1.

TABLE 70

Table 70 provides 160 compounds of formula (70)

(70)

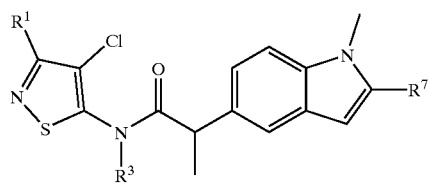

wherein R¹, R³ and R⁷ are as defined in Table 1.

TABLE 71

Table 71 provides 160 compounds of formula (71)

(71)

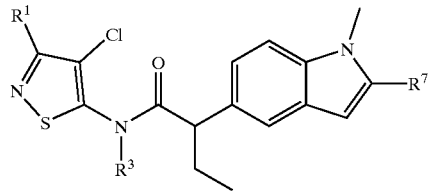

wherein R¹, R³ and R⁷ are as defined in Table 1.

TABLE 72

Table 72 provides 160 compounds of formula (72)

(72)

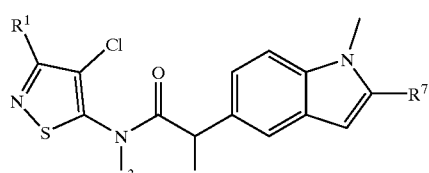

wherein R¹, R³ and R⁷ are as defined in Table 1.

TABLE 73

Table 73 provides 160 compounds of formula (73)

(73)

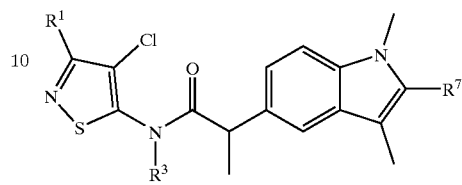

wherein R¹, R³ and R⁷ are as defined in Table 1.

TABLE 74

Table 74 provides 160 compounds of formula (74)

(74)

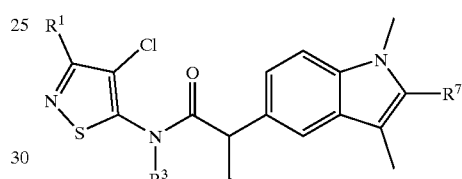

wherein R¹, R³ and R⁷ are as defined in Table 1.

TABLE 75

Table 75 provides 160 compounds of formula (75)

(75)

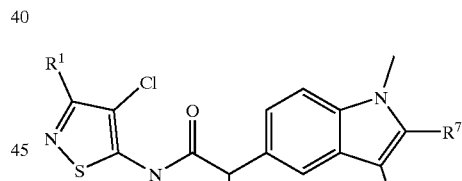

wherein R¹, R³ and R⁷ are as defined in Table 1.

TABLE 76

Table 76 provides 160 compounds of formula (76)

(76)

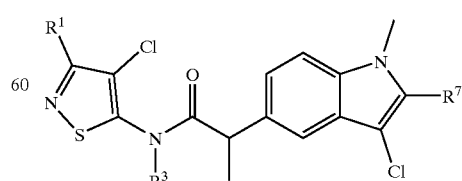

wherein R¹, R³ and R⁷ are as defined in Table 1.

TABLE 77

Table 77 provides 160 compounds of formula (77)

(77)

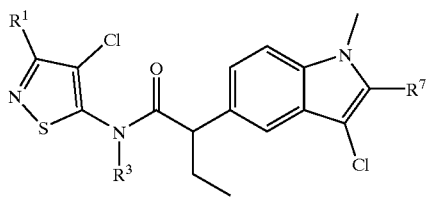

wherein R¹, R³ and R⁷ are as defined in Table 1.

TABLE 78

Table 78 provides 160 compounds of formula (78)

(78)

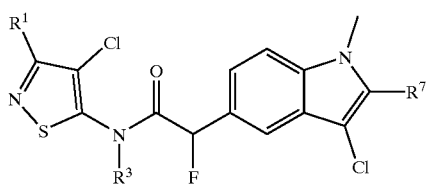

wherein R¹, R³ and R⁷ are as defined in Table 1.

TABLE 79

Table 79 provides 160 compounds of formula (79)

(79)

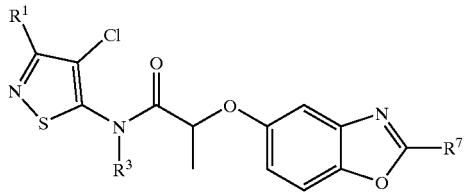

wherein R¹, R³ and R⁷ are as defined in Table 1.

TABLE 80

Table 80 provides 160 compounds of formula (80)

(80)

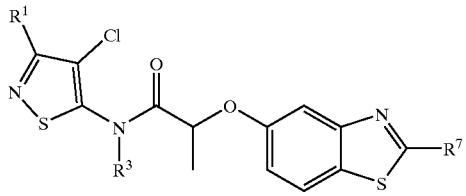

wherein R¹, R³ and R⁷ are as defined in Table 1.

TABLE 81

Table 81 provides 160 compounds of formula (81)

(81)

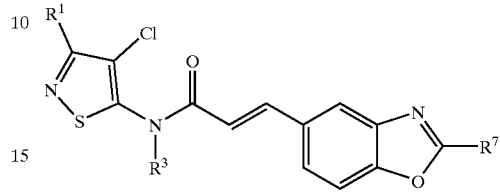

wherein R¹, R³ and R⁷ are as defined in Table 1.

TABLE 82

Table 82 provides 160 compounds of formula (82)

(82)

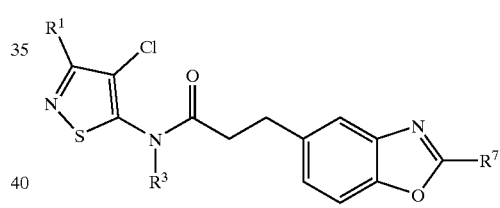

wherein R¹, R³ and R⁷ are as defined in Table 1.

TABLE 83

Table 83 provides 160 compounds of formula (83)

(83)

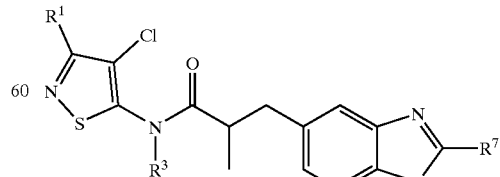

wherein R¹, R³ and R⁷ are as defined in Table 1.

TABLE 84

Table 84 provides 160 compounds of formula (84)

(84)

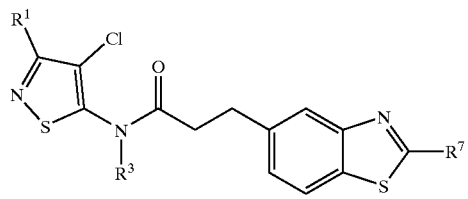

wherein $R^1$, $R^3$ and $R^7$ are as defined in Table 1.

TABLE 85

Table 85 provides 160 compounds of formula (85)

(85)

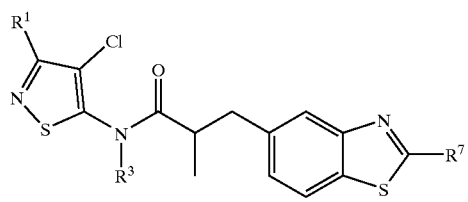

wherein $R^1$, $R^3$ and $R^7$ are as defined in Table 1.

TABLE 86

Table 86 provides 160 compounds of formula (86)

(86)

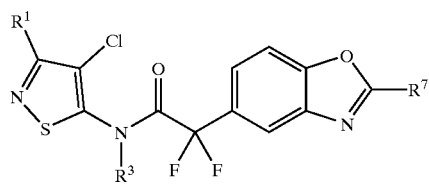

wherein $R^1$, $R^3$ and $R^7$ are as defined in Table 1.

TABLE 87

Table 87 provides 160 compounds of formula (87)

(87)

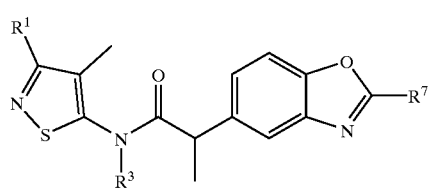

wherein $R^1$, $R^3$ and $R^7$ are as defined in Table 1.

TABLE 88

Table 88 provides 160 compounds of formula (88)

(88)

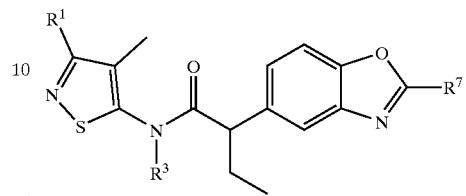

wherein $R^1$, $R^3$ and $R^7$ are as defined in Table 1.

TABLE 89

Table 89 provides 160 compounds of formula (89)

(89)

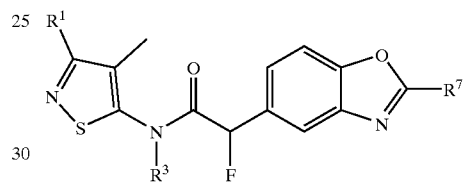

wherein $R^1$, $R^3$ and $R^7$ are as defined in Table 1.

TABLE 90

Table 90 provides 160 compounds of formula (90)

(90)

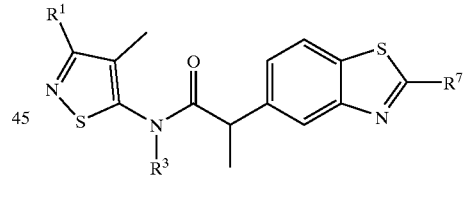

wherein $R^1$, $R^3$ and $R^7$ are as defined in Table 1.

TABLE 91

Table 91 provides 160 compounds of formula (91)

(91)

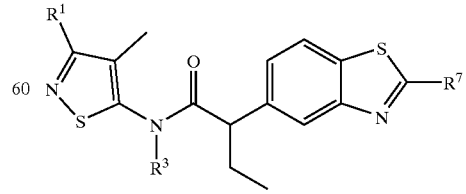

wherein $R^1$, $R^3$ and $R^7$ are as defined in Table 1.

TABLE 92

Table 92 provides 160 compounds of formula (92)

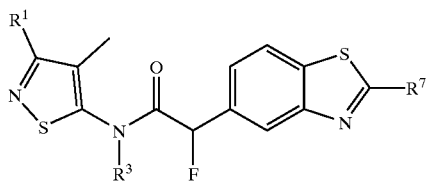

wherein R¹, R³ and R⁷ are as defined in Table 1.

TABLE 93

Table 93 provides 160 compounds of formula (93)

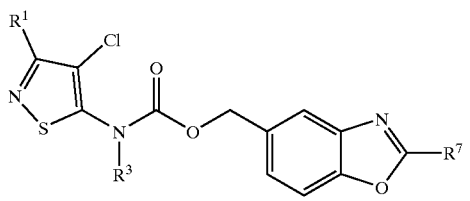

wherein R¹, R³ and R⁷ are as defined in Table 1.

TABLE 94

Table 94 provides 160 compounds of formula (94)

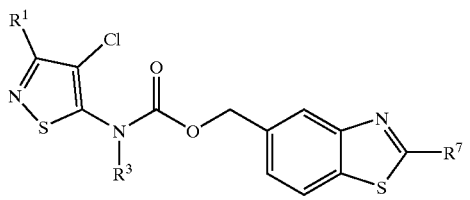

wherein R¹, R³ and R⁷ are as defined in Table 1.

Table 95 provides 80 compounds of formula (95)

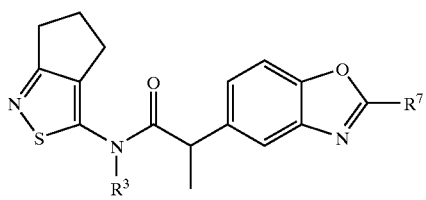

wherein R³ and R⁷ are defined in Table 95.

TABLE 95

| Compound No. | R³ | R⁷ |
| --- | --- | --- |
| 1 | H | $CH_3$ |
| 2 | H | $CH_2CH_3$ |
| 3 | H | $CH_2CH_2CH_3$ |
| 4 | H | $CH(CH_3)_2$ |
| 5 | H | $C(CH_3)_3$ |
| 6 | H | $CH_2CH(CH_3)_2$ |
| 7 | H | $CH_2C(CH_3)_3$ |
| 8 | H | $CH_2CF_3$ |
| 9 | H | $CF_2CF_3$ |
| 10 | H | $CF_2CF_2CF_3$ |
| 11 | $CH_3$ | $CH_3$ |
| 12 | $CH_3$ | $CH_2CH_3$ |
| 13 | $CH_3$ | $CH_2CH_2CH_3$ |
| 14 | $CH_3$ | $CH(CH_3)_2$ |
| 15 | $CH_3$ | $C(CH_3)_3$ |
| 16 | $CH_3$ | $CH_2CH(CH_3)_2$ |
| 17 | $CH_3$ | $CH_2C(CH_3)_3$ |
| 18 | $CH_3$ | $CH_2CF_3$ |
| 19 | $CH_3$ | $CF_2CF_3$ |
| 20 | $CH_3$ | $CF_2CF_2CF_3$ |
| 21 | $CH_2CH_3$ | $CH_3$ |
| 22 | $CH_2CH_3$ | $CH_2CH_3$ |
| 23 | $CH_2CH_3$ | $CH_2CH_2CH_3$ |
| 24 | $CH_2CH_3$ | $CH(CH_3)_2$ |
| 25 | $CH_2CH_3$ | $C(CH_3)_3$ |
| 26 | $CH_2CH_3$ | $CH_2CH(CH_3)_2$ |
| 27 | $CH_2CH_3$ | $CH_2C(CH_3)_3$ |
| 28 | $CH_2CH_3$ | $CH_2CF_3$ |
| 29 | $CH_2CH_3$ | $CF_2CF_3$ |
| 30 | $CH_2CH_3$ | $CF_2CF_2CF_3$ |
| 31 | $CH_2CH_2CH_3$ | $CH_3$ |
| 32 | $CH_2CH_2CH_3$ | $CH_2CH_3$ |
| 33 | $CH_2CH_2CH_3$ | $CH_2CH_2CH_3$ |
| 34 | $CH_2CH_2CH_3$ | $CH(CH_3)_2$ |
| 35 | $CH_2CH_2CH_3$ | $C(CH_3)_3$ |
| 36 | $CH_2CH_2CH_3$ | $CH_2CH(CH_3)_2$ |
| 37 | $CH_2CH_2CH_3$ | $CH_2C(CH_3)_3$ |
| 38 | $CH_2CH_2CH_3$ | $CH_2CF_3$ |
| 39 | $CH_2CH_2CH_3$ | $CF_2CF_3$ |
| 40 | $CH_2CH_2CH_3$ | $CF_2CF_2CF_3$ |
| 41 | $CH_2CH=CH_2$ | $CH_3$ |
| 42 | $CH_2CH=CH_2$ | $CH_2CH_3$ |
| 43 | $CH_2CH=CH_2$ | $CH_2CH_2CH_3$ |
| 44 | $CH_2CH=CH_2$ | $CH(CH_3)_2$ |
| 45 | $CH_2CH=CH_2$ | $C(CH_3)_3$ |
| 46 | $CH_2CH=CH_2$ | $CH_2CH(CH_3)_2$ |
| 47 | $CH_2CH=CH_2$ | $CH_2C(CH_3)_3$ |
| 48 | $CH_2CH=CH_2$ | $CH_2CF_3$ |
| 49 | $CH_2CH=CH_2$ | $CF_2CF_3$ |
| 50 | $CH_2CH=CH_2$ | $CF_2CF_2CF_3$ |
| 51 | $CH_2C.CH$ | $CH_3$ |
| 52 | $CH_2C.CH$ | $CH_2CH_3$ |
| 53 | $CH_2C.CH$ | $CH_2CH_2CH_3$ |
| 54 | $CH_2C.CH$ | $CH(CH_3)_2$ |
| 55 | $CH_2C.CH$ | $C(CH_3)_3$ |
| 56 | $CH_2C.CH$ | $CH_2CH(CH_3)_2$ |
| 57 | $CH_2C.CH$ | $CH_2C(CH_3)_3$ |
| 58 | $CH_2C.CH$ | $CH_2CF_3$ |
| 59 | $CH_2C.CH$ | $CF_2CF_3$ |
| 60 | $CH_2C.CH$ | $CF_2CF_2CF_3$ |
| 61 | $CH_2OCH_3$ | $CH_3$ |
| 62 | $CH_2OCH_3$ | $CH_2CH_3$ |
| 63 | $CH_2OCH_3$ | $CH_2CH_2CH_3$ |
| 64 | $CH_2OCH_3$ | $CH(CH_3)_2$ |
| 65 | $CH_2OCH_3$ | $C(CH_3)_3$ |
| 66 | $CH_2OCH_3$ | $CH_2CH(CH_3)_2$ |
| 67 | $CH_2OCH_3$ | $CH_2C(CH_3)_3$ |
| 68 | $CH_2OCH_3$ | $CH_2CF_3$ |
| 69 | $CH_2OCH_3$ | $CF_2CF_3$ |
| 70 | $CH_2OCH_3$ | $CF_2CF_2CF_3$ |
| 71 | $CH_2OCH_2CH_3$ | $CH_3$ |
| 72 | $CH_2OCH_2CH_3$ | $CH_2CH_3$ |
| 73 | $CH_2OCH_2CH_3$ | $CH_2CH_2CH_3$ |
| 74 | $CH_2OCH_2CH_3$ | $CH(CH_3)_2$ |
| 75 | $CH_2OCH_2CH_3$ | $C(CH_3)_3$ |

TABLE 95-continued

| Compound No. | $R^3$ | $R^7$ |
|---|---|---|
| 76 | $CH_2OCH_2CH_3$ | $CH_2CH(CH_3)_2$ |
| 77 | $CH_2OCH_2CH_3$ | $CH_2C(CH_3)_3$ |
| 78 | $CH_2OCH_2CH_3$ | $CH_2CF_3$ |
| 79 | $CH_2OCH_2CH_3$ | $CF_2CF_3$ |
| 80 | $CH_2OCH_2CH_3$ | $CF_2CF_2CF_3$ |

TABLE 96

Table 96 provides 80 compounds of formula (96)

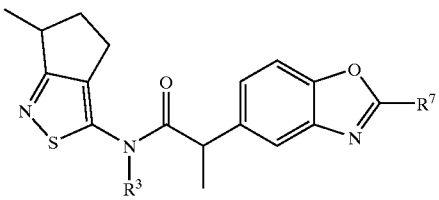

(96)

wherein $R^3$ and $R^7$ are as defined in Table 95.

TABLE 97

Table 97 provides 80 compounds of formula (97)

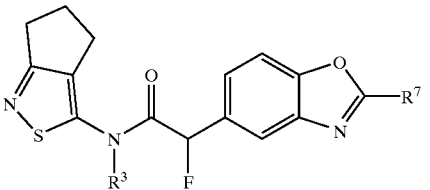

(97)

wherein $R^3$ and $R^7$ are as defined in Table 95.

TABLE 98

Table 98 provides 80 compounds of formula (98)

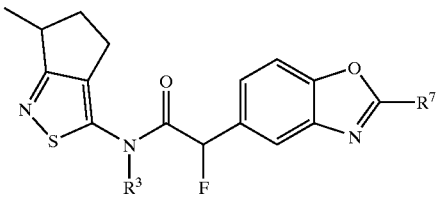

(98)

wherein $R^3$ and $R^7$ are as defined in Table 95.

TABLE 99

Table 99 provides 80 compounds of formula (99)

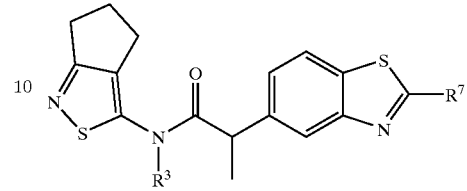

(99)

wherein $R^3$ and $R^7$ are as defined in Table 95.

TABLE 100

Table 100 provides 80 compounds of formula (100)

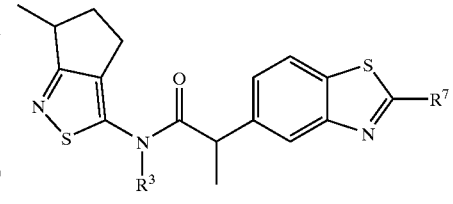

(100)

wherein $R^3$ and $R^7$ are as defined in Table 95.

TABLE 101

Table 101 provides 80 compounds of formula (101)

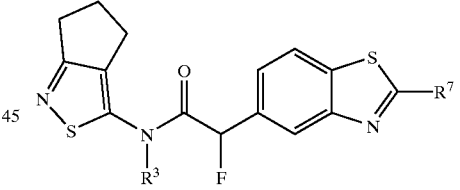

(101)

wherein $R^3$ and $R^7$ are as defined in Table 95.

TABLE 102

Table 102 provides 80 compounds of formula (102)

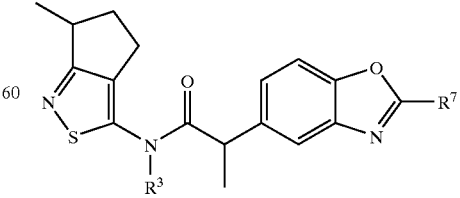

(102)

wherein $R^3$ and $R^7$ are as defined in Table 95.

The following abbreviations are used throughout this description:

| | |
|---|---|
| m.p. = melting point | ppm = part per million |
| s = singlet | b = broad |
| d = doublet | dd = doublet of doublets |
| t = triplet | q = quartet |
| m = multiplet | |

Table 103 shows selected melting point and selected NMR data, all with $CDCl_3$ as the solvent (unless otherwise stated; if a mixture of solvents is present, this is indicated as, for example, ($CDCl_3/d_6$-DMSO)), (no attempt is made to list all characterising data in all cases) for compounds of Tables 1–102.

TABLE 103

| Table No. | Compound No. | M.P. (/° C.) | NMR proton shifts(/ppm) ($CDCl_3$ unless otherwise stated) |
|---|---|---|---|
| 1 | 6 | 172–173 | 1.05(d,6H); 1.70(d,3H);2.31(m,1H); 2.35(s,3H); 2.82(d,2H); 4.00(q,1H); 7.29(dd,1H); 7.52(1H); 7.66(d,1H); 8.07(b,1H). |
| 1 | 7 | 199–200 | 1.08(s,9H); 1.70(d,3H); 2.36(s,3H); 2.84(s,2H); 3.98(q,1H); 7.28(dd,1H); 7.52(d,1H); 7.68(d,1H); 8.00(b,1H): |
| 1 | 8 | 148–150 | 1.70(d,3H); 2.39(s,3H); 3.84(q,2H); 4.04(q,1H); 7.40(dd,1H); 7.62(d,1H); 7.76(d,2H); 8.05(b,1H). |
| 1 | 10 | | 1.72(d,3H); 2.39(s,3H); 4.06(m,1H); 7.58(dd,1H); 7.71(d,1H); 7.91(d,1H); 8.1(b,1H). |
| 1 | 76 | | 1.04(d,6H); 1.14(t,3H); 1.52(d,3H); 2.29(m,1H); 2.49(s,3H); 2.79(d,2H); 3.55(m,2H); 3.86(b,1H): 5.08(b,2H); 6.97(b,1H); 7.34(b,2H). |
| 1 | 77 | | 1.10(s,9H); 1.13(t,3H); 1.52(d,3H); 2.48(s,3H); 2.81(s,2H); 3.54(m,2H); 3.87(b,1H); 5.07(bd,2H); 6.98(b,1H); 7.36(b,2H). |
| 1 | 78 | | 1.13(t,3H); 1.52(d,3H); 2.48(s,3H); 3.55(m,2H); 3.80(q,2H); 3.86(b,1H); 5.07(b,2H); 7.09(b,1H); 7.42(b,2H). |
| 1 | 80 | | 1.15(t,3H); 1.54(d,3H); 2.49(s,3H); 3.55(m,2H); 3.91(b,1H); 5.06(b,2H); 7.28(b,1H); 7.57(b,2H). |
| 1 | 81 | 154–155 | 1.26(t,3H); 1.70(d,3H); 2.69(s,3H); 2.71(q,2H); 4.02(q,1H); 7.30(dd,1H); 7.52(d,1H); 7.64(d,1H); 8.16(b,1H). |
| 1 | 86 | 156–157 | 1.05(d,6H); 1.26(t,3H); 1.70(d,3H); 2.31(m,1H); 2.71(q,2H); 2.83(d,2H); 4.01(q,1H); 7.31(dd,1H); 7.52(d,1H); 7.66(d,1H); 8.06(b,1H); |
| 1 | 87 | 150–151 | 1.10(s,9H); 1.26(t,3H); 1.70(d,3H); 2.84(s,2H); 2.71(q,2H); 4.01(q,1H); 7.30(dd,1H); 7.53(d,1H); 7.68(d,1H); 8.11(b,1H). |
| 1 | 88 | 160–161 | 1.27(t,3H); 1.69(d,3H); 2.72(q,2H); 3.83(q,2H); 4.03(q,1H); 7.41(dd,1H); 7.60(d,1H); 7.75(d,1H); 8.08(b,1H). |
| 1 | 90 | 157–158 | 1.28(t,3H); 1.73(d,3H); 2.73(q,2H); 4.07(q,1H); 7.59(dd,1H); 7.73(d,1H); 7.92(d,1H); 8.06(b,1H). |
| 1 | 156 | | 1.04(d,6H); 1.14(t,3H); 1.33(t,3H); 1.52(d,3H); 2.28(m,1H); 2.79(d,2H); 2.80(q,2H); 3.55(m,2H); 3.85(b,1H); 5.07(b,2H); 6.94(b,1H); 7.33(b,2H). |
| 1 | 157 | | 1.08(S,9H); 1.14(t,3H); 1.33(t,3H); 1.52(d,3H); 2.80(m,4H); 3.55(m,2H); 3.87(b,1H); 5.08(b,2H); 6.97(b,1H); 7.34(b,2H). |

TABLE 103-continued

| Table No. | Compound No. | M.P. (/° C.) | NMR proton shifts(/ppm) ($CDCl_3$ unless otherwise stated) |
|---|---|---|---|
| 1 | 159 | | 1.14(t,3H); 1.33(t,3H); 1.52(d,3H); 2.81(m,2H); 3.56(m,2H); 3.81(q,2H); 3.88(b,1H); 5.07(b,2H); 7.07(b,1H); 7.41(b,2H). |
| 1 | 160 | | 1.16(t,3H); 1.34(t,3H); 1.54(d,3H); 2.82(b,2H); 3.58(b,2H); 3.92(b,1H); 5.08(b,2H); 7.27(b,1H); 7.57(b ,2H). |
| 2 | 10 | 106–107 | 0.97(t,3H); 2.17(m,2H); 2.39(s,3H); 3.75(t,1H); 7.59(dd,1H); 7.61(d,1H); 7.9(d,1H); 8.14(b,1H); |
| 2 | 90 | 131–132 | 0.97(t,3H); 1.27(t,3H); 2.17(m,2H); 2.73(q,2H); 3.74(t,1H); 7.6(dd,1H); 7.7(d,1H); 7.9(d,1H); 8.13(b,1H). |
| 3 | 7 | 127–128 | 1.12(s,9H); 1.78(s,6H); 2.35(s,3H); 2.86(s,2H); 7.34(dd,1H); 7.54(d,1H); 7.80(d,1H); 7.8(b,1H). |
| 4 | 7 | | 0.88(t,3H); 1.12(s,9H); 1.74(s,3H); 2.24(m,2H); 2.35(s,2H); 2.85(s,2H); 7.30(dd,1H); 7.54(d,1H); 7.75(d,1H); 7.82(b,1H). |
| 5 | 6 | 106–106 | 1.03(d,6H); 2.3(m,1H); 2.45(s,3H); 2.82(d,2H); 6.18(d,1H); 7.42(dd,1H); 7.53(d,1H); 7.8(d,1H); 9.06(b,1h). |
| 5 | 7 | 125–126 | 1.08(s,9H); 2.43(s,3H); 2.83(s,2H); 6.18(d,1H); 7.43(dd,1H); 7.56(d,1H); 7.82(d,1H); 9.08(b,1H). |
| 5 | 10 | 134–135 | 2.45(s,3H); 6.26(d,1H); 7.72(dd,1H); 7.79(d,1H); 8.1(d,1H); 9.07(b,1H). |
| 5 | 77 | 90–92 | 1.10(s,9H); 1.15(t,3H); 2.45(b,3H); 2.82(s,2H); 3.58(b,2H); 5.10(b,2H); 5.94(bd,1H); 7.15(b,1H); 7.46(bm,2H). |
| 5 | 86 | 98–99 | 1.05(d,6H); 1.31(t,3H); 2.3(m,1H); 2.8(m,4H); 6.18(d,1H); 7.42(dd,1H); 7.54(d,1H); 7.8(d,1H); 9.08(b,1H). |
| 5 | 87 | 117–118 | 1.09(s,9H); 1.3(t,3H); 2.8(m,4H); 6.18(d,1H); 7.42(dd,1H); 7.55(d,1H); 7.8(d,1H); 9.08(b,1H). |
| 5 | 90 | 92–93 | 1.31(t,3H); 2.8(q,2H); 6.25(d,1H); 7.7(dd,1H); 7.78(d,1H); 8.08(d,1H); 9.08(b,1H). |
| 5 | 157 | | 1.1(b,9H); 1.14(b,3H); 1.35(b,3H); 2.8(b,4H); 3.62(b,2H); 5.3(b,2H); 5.95(bd,1H); 7.14(b,1H); 7.45(b,2H). |
| 5 | 160 | 88–89 | 1.15(t,3H); 1.3(t,3H); 2.8(b,2H); 3.6(bm,2H); 5.15(b,2H); 5.9(b,1H); 7.4(b,1H); 7.68(b,2H). |
| 6 | 7 | | 1.08(s,9H); 2.09(d,3H); 2.42(s,3H); 2.83(s,2H); 7.52(m,2H); 7.91(d,1H); 9.02(b,1H). |
| 7 | 7 | 80–81 | 1.06(s,9H); 2.41(s,3H); 2.79(s,2H); 4.57(b,1H); 5.52(s,1H); 7.43(dd,1H); 7.49(d,1H); 7.80(d,1H); 9.56(b,1H). |
| 9 | 86 | 89–90 | 1.04(d,6H); 1.32(t,3H); 2.3(m,1H); 2.8(m,4H); 3.5(s,3H); 5.01(s,1H); 7.38(dd,1H); 7.5(d,1H); 7.73(d,1H); 9.45(b,1H). |
| 10 | 7 | | 1.05(s,9H); 2.50(s,3H); 2.90(s,2H); 7.65(d,1H); 8.55(dd,1H); 8.90(d,1H); 9.90(b,1H). |
| 11 | 7 | 134–137 | 1.10(s,9H); 2.60(s,3H); 2.88(s,2H); 5.92(s,1H); 6.54(s,1H); 7.10(d,1H); 7.36(dd,1H); 7.78(d,1H); 8.35(b,1H). |
| 12 | 7 | 179–181 | 1.12(s,9H); 2.38(s,3H); 2.87(s,2H); 7.29(d,1H); 7.31(d,1H); 7.62(d,1H); 7.67(d,1H); 8.09(b,1H); 12.56(b,1H). |
| 13 | 7 | 171–173 | 1.08(s,9H); 2.42(s,3H); 2.82(s,2H); 4.14(s,3H); 6.96(s,1H); 7.32(dd,1H); 7.49(d,1H); 7.60(d,1H); 10.30(s,1H). |
| 14 | 7 | 158–159 | 1.14(s,9H); 2.30(s,3H); 2.75(b,6H); 2.88(s,2H); 7.30(dd,1H); 7.58(d,1H); 7.62(b,1H); 7.64(d,1H); 7.78(s,1H). |
| 15 | 7 | | Z-isomer: 1.14(s,9H); 1.30(t,3H); 2.36(s,3H); 2.87(s,2H); 3.35(q,2H); 6.90(d,1H); 7.29(dd,1H); 7.57(d,1H); 7.62(d,1H); 8.00(b,1H); 8.85(m,1H). |

TABLE 103-continued

| Table No. | Compound No. | M.P. (/° C.) | NMR proton shifts(/ppm) (CDCl₃ unless otherwise stated) |
|---|---|---|---|
| 15 | 7 | | E-isomer: 1.16(s,9H); 1.18(t,3H); 2.34(s,3H); 2.89(s,2H); 3.33(q,2H); 4.69(m,1H); 7.25(dd,1H); 7.65(d,1H); 7.68(d,1H); 7.70(b,1H); 7.88(d,1H). |
| 16 | 7 | 76–77 | Z-isomer: 1.12(s,9H); 2.35(s,3H); 2.86(s,2H); 3.80(s,3H); 4.04(d,2H); 6.78(d,1H); 7.30(dd,1H); 7.55(d,1H); 7.64(d,1H); 8.04(b,1H); 8.96(m,1H). |
| 16 | 7 | 85–86 | E-isomer: 1.14(s,9H); 2.34(s,3H); 2.88(s,2H); 3.76(s,3H); 3.98(d,2H); 4.92(m,1H); 7.30(dd,1H); 7.72(m,4H). |
| 17 | 7 | 206–208 | 1.14(s,9H); 2.31(s,3H); 2.88(s,2H); 3.09(m,4H); 3.56(m,4H); 7.28(dd,1H); 7.58–7.66(m,3H); 7.74(s,1H). |
| 18 | 7 | 159–161 | 1.09(s,9H); 2.35(s,3H); 2.80(s,2H); 3.14(m,1H); 3.62(m,1H); 4.00(t,1H); 6.90(m,2H); 7.07(m,2H); 7.28(dd,1H); 7.50(d,1H); 8.15(b,1H). |
| 19 | 7 | 160–162 | Z-isomer: 1.12(s,9H); 2.35(s,3H); 2.86(s,2H); 4.42(d,2H); 6.89(d,2H); 7.20–7.52(m,7H); 8.04(s,1H); 9.14(m,1H). |
| 19 | 7 | | E-isomer: 1.12(s,9H); 2.32(s,3H); 2.87(s,2H); 4.36(d,2H); 4.90(d,2H); 7.10–7.68(m,7H); 7.72(s,1H); 7.89(d,1H). |
| 20 | 7 | 151–153 | 1.10(s,9H); 2.35(s,3H); 2.84(s,2H); 3.15(m,2H); 4.27(m,1H); 7.32(dd,1H); 7.59(d,H); 7.70(d,1H); 8.48(b,1H). |
| 22 | 7 | | 1.10(s,9H); 1.35(dd,6H); 2.45(s,3H); 2.80(s,2H); 3.05(m,1H); 4.95(s,1H); 7.35(dd,1H); 7.50(d,1H); 7.70(d,1H); 9.80(b,1H). |
| 28 | 7 | 166 | 1.03(s,9H); 2.0(s,3H); 2.32(s,3H); 2.77(s,2H); 4.18(m,1H); 4.45(m,1H); 4.68(m,1H); 7.25(dd,1H); 7.44(d,1H); 7.62(d,1H); 8.42(b,1H). |
| 29 | 7 | | 1.1(s,9H); 2.1(s,6H); 2.41(s,3H); 2.82(s,2H); 4.54(d,2H); 4.93(d,2H); 7.2(dd,1H); 7.51(d,1H); 7.6(d,1H); 9.01(b,1H). |
| 30 | 7 | 104–105 | 1.09(s,9H); 1.30(t,3H); 2.42(s,3H); 2.84(2H); 4.23(m,4H); 6.79(t,1H); 7.35(dd,1H); 7.65(d,1H); 7.74(d,1H); 9.66(b,1H). |
| 39 | 86 | 176.8–184.7 | 1.05(d,6H); 1.25(t,3H); 1.72(d,3H); 2.24(m,1H); 2.72(q,2H); 3.01(d,2H); 4.03(q,1H); 7.36(dd,1H); 7.88(d,1H); 7.97(d,1H). |
| 39 | 87 | 211.7–211.8 | 1.1(s,9H); 1.27(t,3H); 1.74(d,3H); 2.73(q,2H); 3.02(s,2H); 4.03(q,m,1H); 7.37(dd,1H); 7.89(d,1H); 8.0(d,1H). |
| 39 | 156 | | 1.06(d,6H); 1.17(t,3H); 1.37(t,3H); 1.58(d,3H); 2.22(m,1H); 2.81(b,2H); 2.98(d,2H); 3.5–3.63(m,2H); 3.9(b,1H);4.9–5.3(b,2H); 7.05(b,1H); 7.62(b,1H); 7.75(b,1H). |
| 39 | 157 | | 1.11(s,9H); 1.14(t,3H); 1.35(t,3H); 157(d,3H); 2.8(b,2H); 3.0(s,2H); 3.55(m,2H); 3.91(b,1H); 5.53(b,2H); 7.05(b,1H); 7.65(b,1H); 7.7(d,3H). |
| 40 | 87 | | 1.0(t,3H); 1.11(s,9H); 1.3(t,3H); 2-2.1(m,1H); 2.3-2.4(m,1H); 2.72(q,2H); 3.03(s,2H); 3.75(t,3H); 7.38(dd,1H); 7.87(d,1H); 7.97(d,1H); 8.18(b,1H). |
| 42 | 7 | 146–146.6 | 1.11(s,9H); 2.48(s,3H); 3.03(s,2H); 6.17–6.29(d,1H); 7.48(dd,1H); 7.92(d,1H); 8.13(d,1H); 9.11(b,1H). |
| 42 | 87 | 117–132 | 1.1(s,9H); 1.3(t,3H); 2.81(q,2H); 3.03(s,2H); 6.61–6.28(d,1H); 7.48(dd,1H); 7.92(d,1H); 8.11(d,1H); 9.09(b,1H). |
| 81 | 7 | 237–238 | 1.11(s,9H); 2.45(s,3H); 2.85(s,2H); 6.67(d,1H); 7.54(m,2H); 7.92(d,1H); 7.98(d,1H); 8.26(b,1H). |

TABLE 103-continued

| Table No. | Compound No. | M.P. (/° C.) | NMR proton shifts(/ppm) (CDCl₃ unless otherwise stated) |
|---|---|---|---|
| 81 | 77 | 96–98 | 1.08(s,9H); 1.27(t,3H); 2.54(s,3H); 2.82(s,2H); 3.69(q,2H); 5.23(b,2H); 6.44(bd,1H); 7.38(dd,1H); 7.47(d,1H); 7.77(d,1H); 7.94(d,1H). |
| 82 | 7 | 170–171 | 1.08(s,9H); 2.38(s,3H); 2.80(s,2H); 2.90(t,2H); 3.29(t,2H); 7.17(dd,1H); 7.41(d1H); 7.52(d,1H); 8.34(b,1H). |
| 82 | 77 | | 1.08(s,9H); 1.18(t,3H); 2.48(s,3H); 2.60(b,2H); 2.81(s,2H); 3.10(t,2H); 3.54(q,2H); 5.08(b,2H); 7.10(bd,1H); 7.39(d,1H); 7.44(b,1H). |
| 83 | 7 | 137–138 | 1.09(s,9H); 1.38(d,3H); 2.37(s,3H); 2.82(s,2H); 2.88(m,2H); 3.07(m,1H); 7.11(dd,1H); 7.40(d,1H); 7.50(d,1H); 7.76(b,1H). |
| 86 | 7 | | 1.09(s,9H); 2.44(s,3H); 2.85(s,2H); 7.63(m,2H); 7.99(d,1H); 8.95(b,1H). |

The compounds of the invention may be made in a variety of ways.

For example, a compound of formula (I) which is a compound of formula (A) (where A, B, Z, R¹, R², R³, R⁴, R⁵, R⁶ and R⁷ are as defined above for a compound of formula (I) except that R³ is not H) may be made from a compound of formula (B) (where A, B, Z, R¹, R², R⁴, R⁵, R⁶ and R⁷ are as defined above for a compound of formula (I)) by treatment with an alkylating agent (such as an alkyl halide, dialkyl sulfate or trialkyloxonium salt), an acylating agent (such as an acid chloride) or a similar reagent (such as a carbamoyl chloride or sulfenyl chloride), optionally in the presence of a base. Frequently these reactions give rise to a mixture of a compound of formula (A) with a compound of formula (C) as an isomeric product. A compound of formula (A) may be separated from a compound of formula (C) and purified by routine techniques (such as recrystallisation, chromatography or trituration with a suitable solvent).

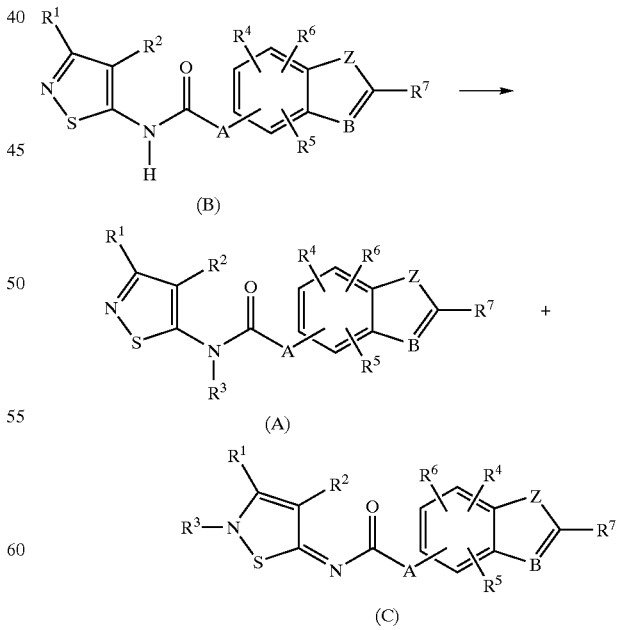

A compound of formula (A) (where A, B, Z, R¹, R², R⁴, R⁵, R⁶ and R⁷ are as defined above for a compound of formula (I) and where R³ is alkoxyalkyl or acyloxyalkyl)

may also be prepared from a compound of formula (B) (where A, B, Z, $R^1$, $R^2$, $R^4$, $R^5$, $R^6$ and $R^7$ are as defined above for a compound of formula (I)) by sequential reaction with formaldehyde and an alkylating or acylating agent.

A compound of formula (B) (where B, Z, $R^1$, $R^2$, $R^4$, $R^5$, $R^6$ and $R^7$ are as defined above for a compound of formula (I) and A is optionally substituted alkylene, alkenylene, alkynylene, alkylenoxy, alkylenamino or alkylenethio) may be prepared by reacting a compound of formula (II) (where $R^1$ and $R^2$ are as defined above for a compound of formula (I)) either with an appropriate compound of formula (III) (where B, Z, $R^4$, $R^5$, $R^6$ and $R^7$ are as defined above for a compound of formula (I); A is optionally substituted alkylene, alkenylene, alkynylene, alkylenoxy, alkylenamino or alkylenethio; and X is OH) preferably in the presence of a suitable coupling reagent (such as 1,3-dicyclohexylcarbodiimide, 1,3-diisopropylcarbodiimide, 1-(3-dimethylaminopropyl)-3-ethylcarbodiimide or 1,1'-carbonyldiimidazole) or with a suitable compound of formula (III) (where B, Z, $R^4$, $R^5$, $R^6$ and $R^7$ are as defined above for a compound of formula (I); A is optionally substituted alkylene, alkenylene, alkynylene, alkylenoxy, alkylenamino or alkylenethio; and X is halogen, acyloxy, alkoxy (especially methoxy), substituted alkoxy or aryloxy) optionally in the presence of a base (such as triethylamine or sodium methoxide) and in a suitable solvent (such as 1,1,2,2-tetrachloroethane, tetrahydrofuran, N,N-dimethylacetamide or mesitylene). A compound of formula (B) (where B, Z, $R^4$, $R^5$, $R^6$ and $R^7$ are as defined above for a compound of formula (I); and A is optionally substituted oxyalkylene) may be prepared in an analogous manner starting from a compound of formula (II) (where $R^1$ and $R^2$ are as defined above for a compound of formula (I)) and a suitable compound of formula (III) (where B, Z, $R^4$, $R^5$, $R^6$ and $R^7$ are as defined above for a compound of formula (I); A is optionally substituted oxyalkylene; and X is chloro).

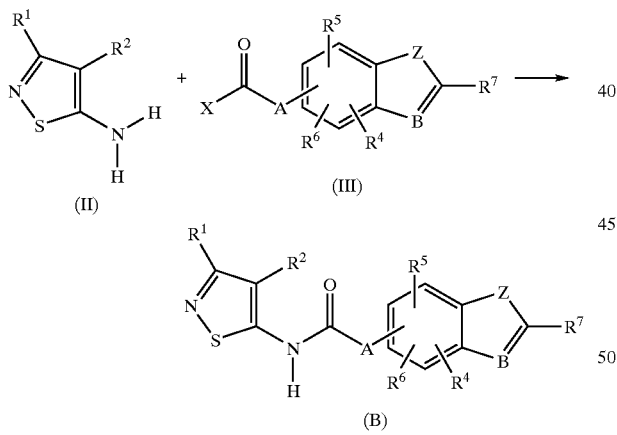

Compounds of formula (II) (where $R^1$ and $R^2$ are as defined above for a compound of formula (I)) are known compounds or may be made from known compounds by known methods.

A compound of formula (III) (where A, B, Z, $R^4$, $R^5$, $R^6$ and $R^7$ are as defined above for a compound of formula (I) and X is $C_{1-6}$ alkoxy [optionally substituted by halogen, $C_{1-3}$ alkoxy, $C_{1-3}$ alkylthio, tri($C_{1-3}$)alkylsilyl or aryl (itself optionally substituted by $C_{1-3}$ alkyl, $C_{1-3}$ alkoxy, halogen, cyano or nitro)]) may be prepared in a number of ways; the preferred method is dependent on the nature of its fused benzheterocyclic ring and on the nature of its moiety A—C(O)—X (where A and X are as defined above). For example, a suitable reagent Y—C(O)—X (where X is $C_{1-6}$ alkoxy [optionally substituted by halogen, $C_{1-3}$ alkoxy, $C_{1-3}$ alkylthio, tri($C_{1-3}$)alkylsilyl or aryl (itself optionally substituted by $C_{1-3}$ alkyl, $C_{1-3}$ alkoxy, halogen, cyano or nitro)]) and Y is a suitably reactive moiety, such as one of those described below) can be attached to a preformed fused heterocyclic ring. Examples of such procedures include, but are not restricted to, the following:

(i) Coupling a compound of formula (IV) (where B, Z, $R^4$, $R^5$, $R^6$ and $R^7$ are as defined above for a compound of formula (I) and T is hydroxy) with a compound of formula (V) [where X is $C_{1-6}$ alkoxy (optionally substituted by halogen, $C_{1-3}$ alkoxy, $C_{1-3}$ alkylthio, tri($C_{1-3}$)alkylsilyl or aryl (itself optionally substituted by $C_{1-3}$ alkyl, $C_{1-3}$ alkoxy, halogen, cyano or nitro)), $Y^1$ is optionally substituted $C_{1-6}$ alkylene and Hal is chloro, bromo or iodo] under basic conditions to give a compound of formula (III'):

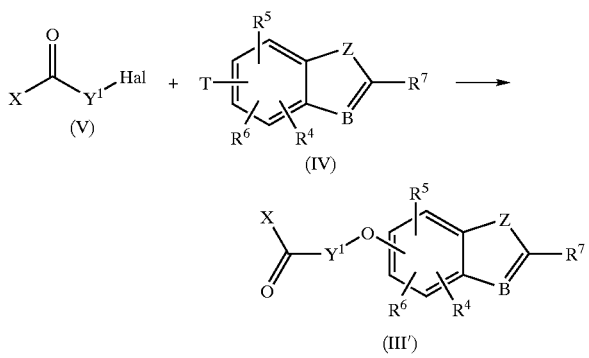

(ii) Coupling a suitably functionalised alkane (such as a malonate), alkene (such as an acrylate) or alkyne with a suitable fused heterocyclic halide (especially bromide or iodide) under transition-metal (especially Cu or Pd) mediated cross-coupling conditions. An example of this type of transformation is the reaction between a compound of formula (VI) [where $R^x$ and $R^y$ are as defined above for substituents on alkenylene, $Y^2$ is a single bond or is optionally substituted $C_{1-4}$ alkylene and X is $C_{1-6}$ alkoxy (optionally substituted by halogen, $C_{1-3}$ alkoxy, $C_{1-3}$ alkylthio, tri($C_{1-3}$)alkylsilyl or aryl (itself optionally substituted by $C_{1-3}$ alkyl, $C_{1-3}$ alkoxy, halogen, cyano or nitro))] and a compound of formula (IV) (where B, Z, $R^4$, $R^5$, $R^6$ and $R^7$ are as defined above for a compound of formula (I) and T is chlorine, bromine or iodine) under Pd(0) catalysis to give a compound of formula (III''):

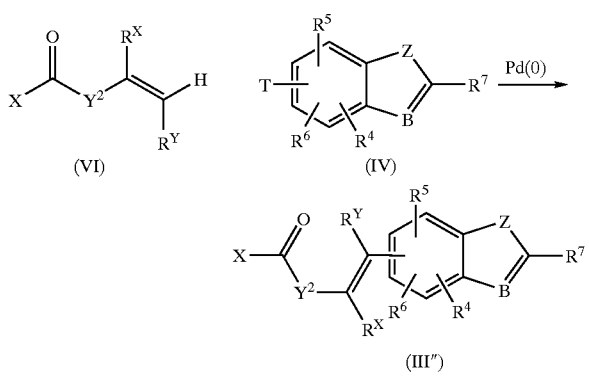

and (iii) Direct alkylation or acylation under, for example, Friedel-Craft conditions.

Certain compounds of formula (III) are amenable to modification to give further analogues. For example, a compound of formula (III) (where B, Z, $R^4$, $R^5$, $R^6$ and $R^7$ are as defined above for a compound of formula (I), X is $C_{1-6}$ alkoxy [optionally substituted by halogen, $C_{1-3}$ alkoxy, $C_{1-3}$ alkylthio, tri($C_{1-3}$)alkylsilyl or aryl (itself optionally substituted by $C_{1-3}$ alkyl, $C_{1-3}$ alkoxy, halogen, cyano or nitro)] and A is $C_{1-6}$ alkylene) undergoes reactions typical of aliphatic esters. Thus a compound of formula (IIIa) [where J is a single bond or a suitable alkylene moiety (such as $CH_2$)] may be reacted with a suitable base (such as lithium diisopropylamide, sodium hydride or lithium hexamethyldisilazide) in a suitable solvent (such as tetrahydrofuran) and then treated with an electrophilic reagent such as an alkylating agent (for example an alkyl halide, alkenylalkyl halide or arylalkyl halide), a halogenating agent (for example N-fluorobenzenesulfonimide) or a further compound with the general formula $R^f$—LG (where LG designates a suitable leaving group, such as a halide and $R^f$ is, for example, a sulfenyl or acyl moiety) to introduce $R^f$ as a new substituent This procedure may be repeated to introduce a second substituent, $R^g$ (which may be the same or different to $R^f$):

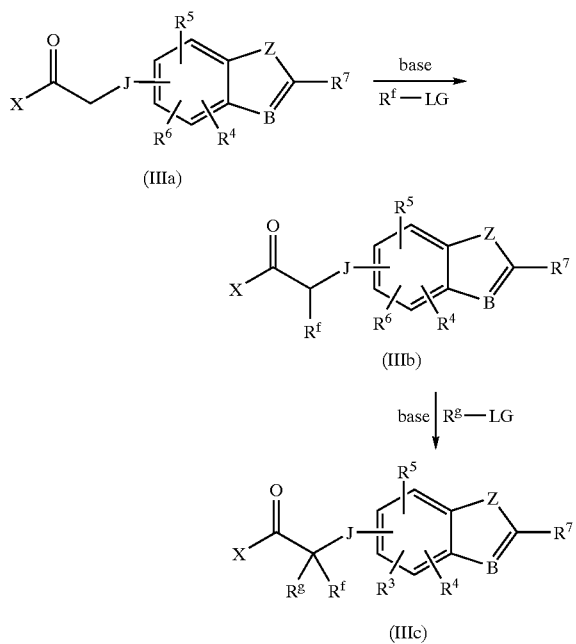

As expected, a compound of formula (III), bearing fragments which are sufficiently chemically reactive, undergoes reactions typical of those fragments. For example, a compound of formula (IIId) [where B, Z, $R^4$, $R^5$, $R^6$ and $R^7$ are as defined above for a compound of formula (I), X is $C_{1-6}$ alkoxy (optionally substituted by halogen, $C_{1-3}$ alkoxy, $C_{1-3}$ alkylthio, tri($C_{1-3}$)alkylsilyl or aryl (itself optionally substituted by $C_{1-3}$ alkyl, $C_{1-3}$ alkoxy, halogen, cyano or nitro)) and J is a single bond or a suitable alkylene moiety (such as $CH_2$)] will undergo certain reactions typical of α-ketoesters; for instance, reduction by a metal hydride (such as sodium borohydride) in a suitable solvent (such as ethanol) to give a corresponding alcohol:

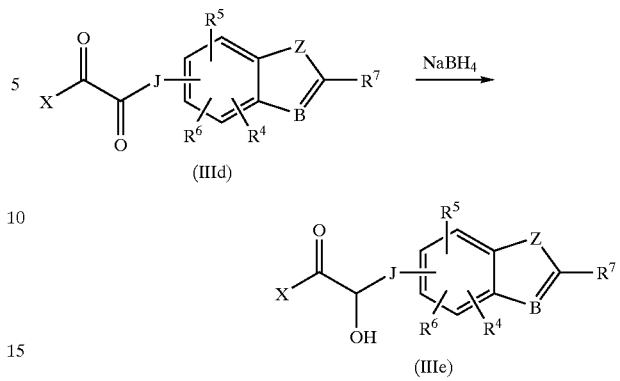

In an alternative preparation of a compound of formula (III) (where A, B, Z, $R^4$, $R^5$, $R^6$ and $R^7$ are as defined above for a compound of formula (I) and X is hydroxy or $C_{1-6}$ alkoxy [optionally substituted by halogen, $C_{1-3}$ alkoxy, $C_{1-3}$ alkylthio, tri($C_{1-3}$)alkylsilyl or aryl (itself optionally substituted by $C_{1-3}$ alkyl, $C_{1-3}$ alkoxy, halogen, cyano or nitro)]) the benzofused heterocyclic ring may be formed by ring synthesis from a suitably substituted benzene of formula (VII) (where Q and G are suitable precursors (atoms or groups) for the formation of the desired heterocyclic ring, A, $R^4$, $R^5$ and $R^6$ are as defined above for a compound of formula (I) and X is hydroxy or $C_{1-6}$ alkoxy [optionally substituted by halogen, $C_{1-3}$ alkoxy, $C_{1-3}$ alkylthio, tri($C_{1-3}$)alkylsilyl or aryl (itself optionally substituted by $C_{1-3}$ alkyl, $C_{1-3}$ alkoxy, halogen, cyano or nitro)]):

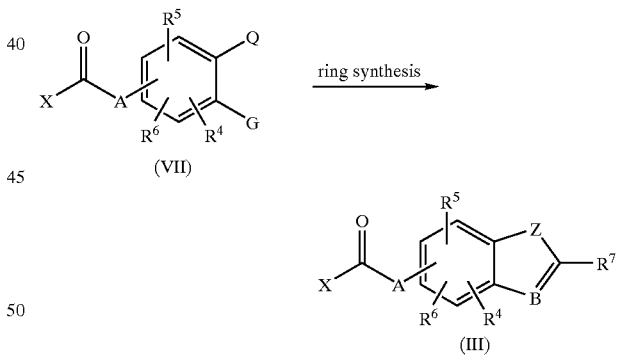

This methodology may be extended to the following transformation:

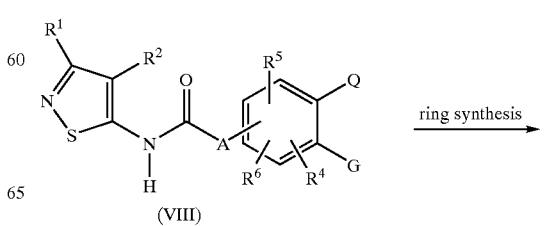

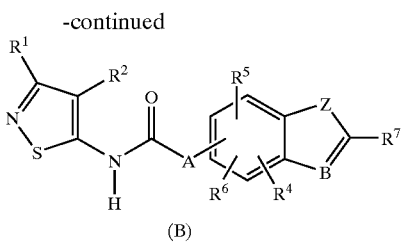

(B)

where A, B, Z, $R^1$, $R^2$, $R^4$, $R^5$, $R^6$ and $R^7$ are as defined above for a compound of formula (I) and Q and G are suitable precursors (atoms or groups) for the formation of the desired heterocyclic ring. For example, when Q is hydroxy and G is amino, treatment of a compound of formula (VIII) either with an acylating agent [such as an acid chloride or anhydride] optionally in the presence of a suitable base (such as triethylamine, potassium carbonate or pyridine) or with an acid (preferably in the presence of a coupling agent (such as 1,3-dicyclohexyl-carbodiimide, 1,3-diisopropylcarbodiimide, 1-(3-dimethylaminopropyl)-3-ethyl-carbodiimide or 1,1'-carbonyldiimidazole)) followed by cyclisation, optionally catalysed by an acid (such as para-toluenesulfonic acid), gives a benzoxazole:

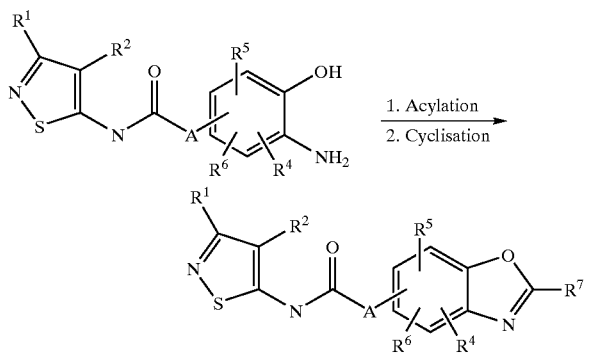

Similar reactions (where G is amino and Q is SH or amino) lead to a benzothiazole or a benzimidazole respectively. Indeed, the synthesis of a substituted benzimidazole, benzoxazole or benzothiazole from a substituted benzene is well known [see for example, Alan R. Katritzky and Charles W. Rees (Comprehensive Heterocyclic Chemistry, Vol. 6, Pergamon Press, 1984); Helmut M. Hugel, Synth. Commun. (15 (12), 1075–1080, (1985)); J. Scheigetz, R. Zboni and B. Roy, Synth. Commun., 25 (18), 2791–2806, (1995); David W. Dunwell, Delme Evans, Terence A. Hicks (J. Med. Chem., 1975, 18, No. 1, 53); Abdou O. Abdelhamid, Cyril Parkanyi, S. M. Khaledur Rashid and Winston D. Lloyd (J. Heterocyclic Chem., 25, 403, (1988)); Teruyuki Kondo, Sungbong Yang, Keun-Tae Huh, Masanobu Kobayashi, Shinju Kotachi and Yoshihisa Watanabe (Chemistry Letters, 1275, 1991); and Dale L. Boger (J. Org. Chem., 43, No 11, 2296, 1978)] and similar processes may be utilised in the synthesis of a compound of formula (III) (where A, B, Z, $R^4$, $R^5$, $R^6$ and $R^7$ are as defined above for a compound of formula (1) and X is hydroxy, halogen, acyloxy, alkoxy, substituted alkoxy or aryloxy) from appropriate starting materials. A benzothiopbene may be made from an appropriate thiophenol by a process similar to those described by Robert D Schuetz and Richard L Titus (J. Heterocycl. Chem., 4, No 4, 465 (1967); suitable thiophenols are known compounds or may be prepared by known methods from known compounds. A benzofuran may be made from an orthohalophenol, as described by Henning Lutjens and Peter J Scammells (Tetrahedron Letters 39 (1998), 6581–6584); Terence C Owen et al., (Tetrahedron Letters 30, No 13, 1597 (1989)); and Fred G Scbreiber and Robert Stevenson (J. C. S. Perkin 1, 90, 1977). An indole may be made from an ortho-haloaniline according to the methods of Cheng-yi Chen et al. (J. Org. Chem 1997, 62, 2676); Takao Sakamoto et al., (J. Org. Chem. 1997, 62, 6507); and Alan D. Adams et al. (WO9827974).

A compound of formula (I) (where A, B, Z, $R^1$, $R^2$, $R^4$, $R^5$, $R^6$ and $R^7$ are as defined above, Y is S and $R^3$ is H) may be prepared by reacting a compound of formula (I) (where A, B, Z, $R^1$, $R^2$, $R^4$, $R^5$, $R^6$ and $R^7$ are as defined above, Y is O and $R^3$ is H) with a suitable thionating agent (such as 2,4-bis(4-methoxyphenyl)-1,3-dithia-2,4-diphosphetane-2,4-disulfide (Lawesson's reagent), 2,4-bis(methylthio)-1,3-dithia-2,4-diphosphetane-2,4-disulfide (Davy reagent methyl), 2,4-bis(para-tolyl)-1,3-dithia-2,4-diphosphetane-2,4-disulfide (Davy reagent p-tolyl) or phosphorus pentasulfide) in a suitable solvent (such as toluene or fluorobenzene).

A compound of formula (IX) (where B, Z, $R^1$, $R^2$, $R^3$, $R^4$, $R^5$, $R^6$ and $R^7$ are as defined above for a compound of formula (I)) may be made by reacting a compound of formula (X) (where B, Z, $R^1$, $R^2$, $R^3$, $R^4$, $R^5$, $R^6$ and $R^7$ are as defined above) with N,N-dimethyl-formamide dialkyl acetal in a suitable solvent (such as toluene or N,N-dimethylformamide). Frequently this reaction produces a mixture of E- and Z-isomers which are sometimes separable by standard techniques (such as flash column chromatography and recrystallisation).

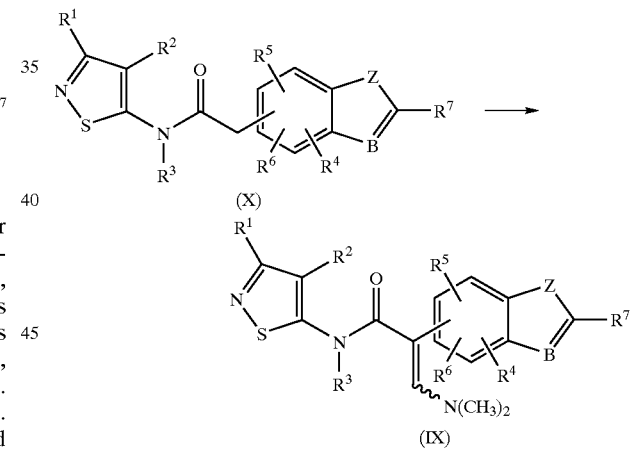

A compound of formula (X) ((where B, Z, $R^1$, $R^2$, $R^3$, $R^4$, $R^5$, $R^6$ and $R^7$ are as defined for a compound of formula (I)) may be treated in an analogous manner with a trialkylorthoformate to afford a compound of formula (XI) (where B, Z, $R^1$, $R^2$, $R^3$, $R^4$, $R^5$, $R^6$ and $R^7$ are as defined for a compound of formula (I) and $R^d$ is $C_{1-6}$ alkyl).

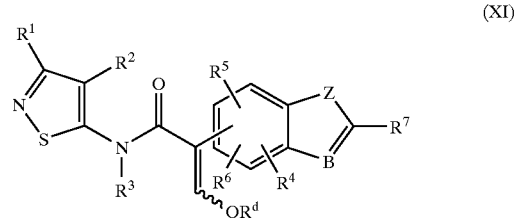

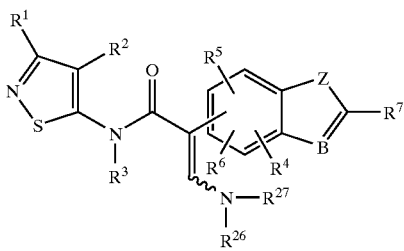

(XII)

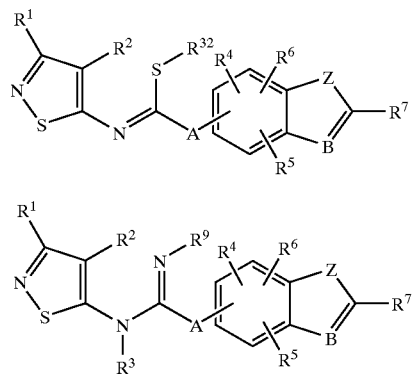

(XIV)

(XV)

A compound of formula (I) (where B, Z, $R^1$, $R^2$, $R^3$, $R^4$, $R^5$, $R^6$ and $R^7$ are as defined above for a compound of formula (I)) may be treated with an amine of formula ($HNR^{26}R^{27}$) (where $R^{26}$ and $R^{27}$ are as defined for a compound of formula (I)) to give a compound of formula (XII) (where B, Z, $R^1$, $R^2$, $R^3$, $R^4$, $R^5$, $R^6$ and $R^7$, $R^{26}$ and as defined above for a compound of formula (I)).

A compound of formula (IX) (where B, Z, $R^1$, $R^2$, $R^3$, $R^4$, $R^5$, $R^6$ and $R^7$ are as defined above for a compound of formula (I)) may be oxidised to a compound of formula (XIII) (where B, Z, $R^1$, $R^2$, $R^3$, $R^4$, $R^5$, $R^6$ and $R^7$ are as defined above for a compound of formula (I)) under known conditions.

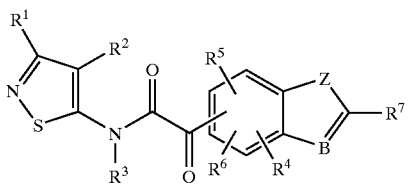

(XIII)

A compound of formula (I) (where Y is S, $R^3$ is H and A, B, Z, $R^1$, $R^2$, $R^4$, $R^5$, $R^6$ and $R^7$ are as defined above for a compound of formula (I)) may be treated with an electrophile (such as an alkyl halide, dialkyl sulfate, chloromethyl ether or trialkyloxonium salt) optionally in the presence of a base to give a compound of formula (XIV) (where $R^{32}$ is alkyl, alkenylalkyl, alkynylalkyl, cycloalkyl, alkoxyalkyl and A, B, Z, $R^1$, $R^2$, $R^4$, $R^5$, $R^6$ and $R^7$ are as defined above for a compound of formula (I)). Such a compound may be further treated with a compound of formula $R^9$—$NH_2$ (where $R^9$ is as defined above for a compound of formula (I)) optionally in the presence of a mercuric salt (such as mercuric chloride), according to known procedures to give a compound of formula (XV) (where $R^3$ is H and A, B, Z, $R^1$, $R^2$, $R^4$, $R^5$, $R^6$ and $R^7$ are as defined above for a compound of formula (I)). Such a compound may be treated with an alkylating agent, an acylating agent or similar electrophile to give a compound of formula (XV) [where A, B, Z, $R^1$, $R^2$, $R^4$, $R^5$, $R^6$ and $R^7$ are as defined above for a compound of formula (I) and $R^3$ is as defined above for a compound of formula (I) (except that $R^3$ is not H)] in an analogous manner to that previously described for the formation of a compound of formula (A) from a compound of formula (B).

The compounds of formula (I) can be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be combated and controlled by the use of the invention compounds include those pests associated with agriculture (which term includes the growing of crops for food and fibre products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

Examples of pest species which may be controlled by the compounds of formula (I) include: *Myzus persicae* (aphid), *Aphis gossypii* (aphid), *Aphis fabae* (aphid), Lygus spp. (capsids), Dysdercus spp. (capsids), *Nitaparvata lugens* (planthopper), *Nephotettixc incticeps* (leafhopper), Nezara spp. (stinkbugs), Euschistus spp. (stinkbugs), Leptocorisa spp. (stinkbugs), *Frankliniella occidentalis* (thrip), Thrips spp. (thrips), *Leptinotarsa decemlineata* (Colorado potato beetle), *Anthonomus grandis* (boll weevil), Aonidella spp. (scale insects), Trialeurodes spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), Agrotis spp. (cutworms), *Chilo suppressalis* (rice stem borer), *Locusta migratoria* (locust), *Chortiocetes terminifera* (locust), Diabrotica spp. (rootworms), *Panonychus ulmi* (European red mite), *Panonychus citri* (citrus red mite), *Tetranychus urticae* (two-spotted spider mite), *Tetranychus cinnabamus* (carmine spider mite), *Phyllocoptruta oleivora* (citrus rust mite), *Polyphagotarsonemus latus* (broad mite), Brevipalpus spp. (flat mites), *Boophilus microplus* (cattle tick), *Dermacentor variabilis* (American dog tick), *Ctenocephalides felis* (cat flea), Liriomyza spp. (leafminer), *Musca domestica* (housefly), *Aedes aegypti* (mosquito), Anopheles spp. (mosquitoes), Culex spp. (mosquitoes), Lucillia spp. (blowflies), *Blattelia germanica* (cockroach), *Periplaneto americana* (cockroach), *Blatta orientalis* (cockroach), termites of the Mastotermitidae (for example Mastotermes spp.), the Kalotermitidae (for example Neotermes spp.), the Rhinotermitidae (for example *Coptotermes formosanus, Reticulitermes flavipes, R. speratu, R.*

*virginicus, R. hesperus,* and *R. santonensis*) and the Termitidae (for example *Globitermes sulphureus*), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodpholus* spp. (banana burrowing nematodes), *Tylenchulus* spp.(citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

The compounds of formula (I) are also active fungicides and may be used to control one or more of the following pathogens: *Pyricularia oryzae* (*Magnaporthe grisea*) on rice and wheat and other Pyricularia spp. on other hosts; *Puccinia recondita, Puccinia striiformis* and other rusts on wheat, *Puccinia hordei, Puccinia striiformis* and other rusts on barley, and rusts on other hosts (for example turf, rye, coffee, pears, apples, peanuts, sugar beet, vegetables and ornamental plants); *Erysiphe cichoracearum* on cucurbits (for example melon); *Erysiphe graminis* (powdery mildew) on barley, wheat, rye and turf and other powdery mildews on various hosts, such as *Sphaerotheca macularis* on hops, *Sphaerotheca fusca* (*Sphaerotheca fuliginea*) on cucurbits (for example cucumber), *Leveillula taurica* on tomatoes, aubergine and green pepper, *Podosphaera leucotricha* on apples and *Uncinula necator* on vines; *Cochliobolus* spp., *Helminthosporium* spp., *Drechslera* spp. (*Pyrenophora* spp.), *Rhynchosporium* spp., *Mycosphaerella graminicola* (*Septoria tritici*) and *Phaeosphaeria nodorum* (*Stagonospora nodorum* or *Septoria nodorum*), *Pseudocercosporella herpotrichoides* and *Gaeumannomyces graminis* on cereals (for example wheat, barley, rye), turf and other hosts; *Cercospora arachidicola* and *Cercosporidium personatum* on peanuts and other Cercospora spp. on other hosts, for example sugar beet, bananas, soya beans and rice; *Botrytis cinerea* (grey mould) on tomatoes, strawberries, vegetables, vines and other hosts and other Botrytis spp. on other hosts; *Alternaria* spp. on vegetables (for example carrots), oil-seed rape, apples, tomatoes, potatoes, cereals (for example wheat) and other hosts; *Venturia* spp. (including *Venturia inaequalis* (scab)) on apples, pears, stone fruit, tree nuts and other hosts; *Cladosporium* spp. on a range of hosts including cereals (for example wheat) and tomatoes; *Monilinia* spp. on stone fruit, tree nuts and other hosts; *Didymella* spp. on tomatoes, turf, wheat, cucurbits and other hosts; *Phoma* spp. on oil-seed rape, turf, rice, potatoes, wheat and other hosts; *Aspergillus* spp. and *Aureobasidium* spp. on wheat, lumber and other hosts; *Ascochyta* spp. on peas, wheat, barley and other hosts; *Stemphylium* spp. (*Pleospora* spp.) on apples, pears, onions and other hosts; summer diseases (for example bitter rot (*Glomerella cingulata*), black rot or frogeye leaf spot (*Botryosphaeria obtusa*), Brooks fruit spot (*Mycosphaerella pomi*), Cedar apple rust (*Gymnosporangium juniperi-virginianae*), sooty blotch (*Gloeodes pomigena*), flyspeck (*Schizothyrium pomi*) and white rot (*Botryosphaeria dothidea*)) on apples and pears; *Plasmopara viticola* on vines; other downy mildews, such as *Bremia lactucae* on lettuce, Peronospora spp. on soybeans, tobacco, onions and other hosts, *Pseudoperonospora humuli* on hops and *Pseudoperonospora cubensis* on cucurbits; *Pythium* spp. (including *Pythium ultimum*) on turf and other hosts; *Phytophthora infestans* on potatoes and tomatoes and other Phytophthora spp. on vegetables, strawberries, avocado, pepper, ornamentals, tobacco, cocoa and other hosts; *Thanatephorus cucumeris* on rice and turf and other Rhizoctonia spp. on various hosts such as wheat and barley, peanuts, vegetables, cotton and turf; *Sclerotinia* spp. on turf, peanuts, potatoes, oil-seed rape and other hosts; *Sclerotium* spp. on turf, peanuts and other hosts; *Gibberella fujikuroi* on rice; *Colletotrichum* spp. on a range of hosts including turf, coffee and vegetables; *Laetisaria fuciformis* on turf; *Mycosphaerella* spp. on bananas, peanuts, citrus, pecans, papaya and other hosts; *Diaporthe* spp. on citrus, soybean, melon, pears, lupin and other hosts; *Elsinoe* spp. on citrus, vines, olives, pecans, roses and other hosts; *Verticillium* spp. on a range of hosts including hops, potatoes and tomatoes; *Pyrenopeziza* spp. on oil-seed rape and other hosts; *Oncobasidium theobromae* on cocoa causing vascular streak dieback; *Fusarium* spp., *Typhula* spp., *Microdochium nivale,* *Ustilago* spp., *Urocystis* spp., *Tilletia* spp. and *Claviceps purpurea* on a variety of hosts but particularly wheat, barley, turf and maize; *Ramularia* spp. on sugar beet, barley and other hosts; post-harvest diseases particularly of fruit (for example *Penicillium digitatum, Penicillium italicum* and *Trichoderma viride* on oranges, *Colletotrichum musae* and *Gloeosporium musarum* on bananas and *Botrytis cinerea* on grapes); other pathogens on vines, notably *Eutypa lata, Guignardia bidwellii, Phellinus igniarus, Phomopsis viticola, Pseudopeziza tracheiphila* and *Stereum hirsutum*; other pathogens on trees (for example *Lophodermium seditiosum*) or lumber, notably *Cephaloascus fragrans,* Ceratocystis spp., *Ophiostoma piceae,* Penicillium spp., *Trichoderma pseudokoningii, Trichoderma viride, Trichoderma harzianum, Aspergillus niger, Leptographium lindbergi* and *Aureobasidium pullulans*; and fungal vectors of viral diseases (for example *Polymyxa graminis* on cereals as the vector of barley yellow mosaic virus (BYMV) and *Polymyxa betae* on sugar beet as the vector of rhizomania).

A compound of formula (I) may move acropetally, basipetally or locally in plant tissue to be active against one or more fungi. Moreover, a compound of formula (I) may be volatile enough to be active in the vapour phase against one or more fungi on the plant.

The invention therefore provides a method of combating and controlling insects, acarines, nematodes or molluscs which comprises applying an insecticidally, acaricidally, nematicidally or molluscicidally effective amount of a compound of formula (I), or a composition containing a compound of formula (I), to a pest, a locus of pest, or to a plant susceptible to attack by a pest, and a method of combating and controlling fungi which comprises applying a fungicidally effective amount of a compound of formula (I), or a composition containing a compound of formula (I), to a plant, to a seed of a plant, to the locus of the plant or seed, to soil or to any other growth medium (for example a nutrient solution). The compounds of formula (I) are preferably used against insects, acarines, nematodes or fungi.

The term "plant" as used herein includes seedlings, bushes and trees. Furthermore, the fungicidal method of the invention includes protectant, curative, systemic, eradicant and antisporulant treatments.

As fungicides, the compounds of formula (I) are preferably used for agricultural, horticultural and turfgrass purposes in the form of a composition.

In order to apply a compound of formula (I) as an insecticide, acaricide, nematicide or molluscicide to a pest, a locus of pest, or to a plant susceptible to attack by a pest, or, as a fungicide to a plant, to a seed of a plant, to the locus of the plant or seed, to soil or to any other growth medium, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests or fungi such that a compound of formula (I) is applied at a rate of from 0.1 g 10 kg per hectare, preferably from 1 g to 6 kg per hectare, more preferably from 1 g to 1 kg per hectare.

When used in a seed dressing, a compound of formula (I) is used at a rate of 0.0001 g to 10 g (for example 0.001 g or 0.05 g), preferably 0.005 g to 10 g, more preferably 0.005 g to 4 g, per kilogram of seed.

In another aspect the present invention provides an insecticidal, acaricidal, nematicidal, molluscicidal or fungicidal composition comprising an insecticidally, acaricidally, nematicidally, molluscicidally or fungicidally effective amount of a compound of formula (I) and a suitable carrier or diluent therefor. The composition is preferably an insecticidal, acaricidal, nematicidal or fungicidal composition.

In a still further aspect the invention provides a method of combating and controlling pests or fungi at a locus which comprises treating the pests or fungi or the locus of the pests or fungi with an insecticidally, acaricidally, nematicidally, molluscicidally or fungicidally effective amount of a composition comprising a compound of formula (I). The compounds of formula (I) are preferably used against insects, acarines, nematodes or fungi.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), microemulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$–$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in in ECs or in EWs. An ME may be either an oil-in-water or a water-in-oil system (which system is present may be determined by conductivity measurements)

and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurised, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal or fungicidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapour or applied through distribution or incorporation of a composition (such as a granular composition or a composition packed in a water-soluble bag) in soil or an aqueous environment A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilisers (for example nitrogen-, potassium- or phosphorus-containing fertilisers). Suitable formulation types include granules of fertiliser. The mixtures suitably contain up to 25% by weight of the compound of formula (I).

The invention therefore also provides a fertiliser composition comprising a fertiliser and a compound of formula (I).

The compositions of this invention may contain other compounds having biological activity, for example micronutrients or compounds having similar or complementary fungicidal activity or which possess plant growth regulating, herbicidal, insecticidal, nematicidal or acaricidal activity.

By including another fungicide, the resulting composition may have a broader spectrum of activity or a greater level of intrinsic activity than the compound of formula (I) alone. Further the other fungicide may have a synergistic effect on the fungicidal activity of the compound of formula (I).

The compound of formula (I) may be the sole active ingredient of the composition or it may be admixed with one or more additional active ingredients such as a pesticide, fungicide, synergist, herbicide or plant growth regulator where appropriate. An additional active ingredient may provide a composition having a broader spectrum of activity or increased persistence at a locus; synergise the activity or complement the activity (for example by increasing the speed of effect or overcoming repellency) of the compound of formula (I); or help to overcome or prevent the development of resistance to individual components. The particular additional active ingredient will depend upon the intended utility of the composition. Examples of suitable pesticides include the following:

a) Pyrethroids, such as permethrin, cypermethrin, fenvalerate, esfenvalerate, deltamethrin, cyhalothrin (in particular lambda-cyhalothrin), bifenthrin, fenpropathrin, cyfluthrin, tefluthrin, fish safe pyrethroids (for example ethofenprox), natural pyrethrin, tetramethrin, s-bioallethrin, fenfluthrin, prallethrin or 5-benzyl-3-furylmethyl-(E)-(1R,3S)-2,2-dimethyl-3-(2-oxothiolan-3-ylidenemethyl)cyclopropane carboxylate;

b) Organophosphates, such as, profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;

c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;

d) Benzoyl ureas, such as diflubenzuron, triflumuron, hexaflumuron, flufenoxuron or chlorfluazuron;

e) Organic tin compounds, such as cyhexatin, fenbutatin oxide or azocyclotin;

f) Pyrazoles, such as tebufenpyrad and fenpyroximate;

g) Macrolides, such as avermectins or milbemycins, for example abamectin, emamectin benzoate, ivermectin, milbemycin, spinosad or azadirachtin;

h) Hormones or pheromones;

i) Organochlorine compounds such as endosulfan, benzene hexachloride, DDT, chlordane or dieldrin;

j) Amidines, such as chlordimeform or amitraz;

k) Fumigant agents, such as chloropicrin, dichloropropane, methyl bromide or metam;

l) Chloronicotinyl compounds such as imidacloprid, thiacloprid, acetamiprid, nitenpyram or thiamethoxam;

m) Diacylhydrazines, such as tebufenozide, chromafenozide or methoxyfenozide;

n) Diphenyl ethers, such as diofenolan or pyriproxifen;

o) Indoxacarb;

p) Chlorfenapyr, or q) Pymetrozine.

In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorobenzilate; or growth regulators, such as hydramethylnon, cyromazine, methoprene, chlorfluazuron or diflubenzuron).

Examples of fungicidal compounds which may be included in the composition of the invention are (E)-N-methyl-2-[2-(2,5-dimethylphenoxymethyl)phenyl]-2-methoxy-iminoacetamide (SSF-129), 4bromo-2-cyano-N,N-dimethyl-6-trifluoromethylbenzimidazole-1-sulphonamide, α-[N-(3-chloro-2,6-xylyl)-2-methoxyacetiamido]-γ-butyrolactone, 4-chloro-2-cyano-N,N-dimethyl-5-p-tolylimidazole-1-sulfonamide (IKF-916, cyamidazosulfamid), 3-5-dichloro-N-(3-chloro-1-ethyl-1-methyl-2-oxopropyl)-4-methylbenzamide (RH-7281, zoxamide), N-alkyl-4,5,-dimethyl-2-trimethylsilylthiophene-3-carboxamide (MON65500), N-(1-cyano-1,2-dimethylpropyl)-2-(2,4-dichlorophenoxy) propionanide ($AC_{382042}$), N-(2-methoxy-5-pyridyl)-cyclopropane carboxamide, acibenzolar (CGA245704), alanycarb, aldimorph, anilazine, azaconazole, azoxystrobin, benalaxyl, benomyl, biloxazol, bitertanol, blasticidin S, bromuconazole, bupirimate, captafol, captan, carbendazim, carbendazim chlorhydrate, carboxin, carpropamid, carvone, CGA41396, CGA41397, chinomethionate, chlorothalonil, chlorozolinate, clozylacon, copper containing compounds such as copper oxychloride, copper oxyquinolate, copper sulphate, copper tallate and Bordeaux mixture, cymoxanil, cyproconazole, cyprodinil, debacarb, di-2-pyridyl disulphide 1,1'-dioxide, dichlofluanid, diclomezine, dicloran, diethofencarb, difenoconazole, difenzoquat, diflumetorim, O,O-di-iso-propyl-S-benzyl thiophosphate, dimefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimol, ethyl(Z)-N-benzyl-N([methyl(methyl-thioethylideneaminooxycarbonyl)amino]thio)-β-alaninate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinam, fludioxonil, flumetover, fluoroimide, fluquinconazole, flusilazole, flutolanil, flutriafol, folpet, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, kasugamycin, kresoximmethyl, LY186054, LY211795, LY248908, mancozeb, maneb, mefenoxam, mepanipyrim, mepronil, metalaxyl, metconazole, metiram, metiram-zinc, metominostrobin, myclobutanil, neoasozin, nickel dimethyldithiocarbamate, nitrothal-isopropyl, nuarimol, ofurace, organomercury compounds, oxadixyl, oxasulfuron, oxolinic acid, oxpoconazole, oxycarboxin, pefurazoate, penconazole, pencycuron, phenazin oxide, phosetyl-Al, phosphorus acids, phthalide, picoxystrobin (ZA1963), polyoxin D, polyram, probenazole, prochloraz, procymidone, propamocarb, propiconazole, propineb, propionic acid, pyrazophos, pyrifenox, pyrimethanil, pyroquilon, pyroxyfur, pyrrolnitrin, quaternary ammonium compounds, quinomethionate, quinoxyfen, quintozene, sipconazole (F-155), sodium pentachlorophenate, spiroxamine, streptomycin, sulphur, tebuconazole, tecloftalam, tecnazene, tetraconazole, thiabendazole, thifuzamid, 2-(thiocyanomethylthio) benzothiazole, thiophanate-methyl, thiram, timibenconazole, toiclofos-methyl, tolyifluanid, triadimefon, triadimenol, triazbutil, triazoxide, tricyclazole, tridemorph, trifloxystrobin (CGA279202), triforine, triflumizole, triticonazole, validamycin A, vapam, vinclozolin, zineb and ziram.

The compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The invention is illustrated by the following Examples:

EXAMPLE 1

This Example illustrates the preparation of N-(4-chloro-3-methylisothiazol-5-yl)-[2-(2,2-dimethylpropyl)benzoxazol-5-yl]acetamide.

Step 1
Preparation of 5-amino-4-chloro-3-methylisthiazole

5-Amino-3-methylisothiazole hydrochloride (250 g, 1.66 mole) was suspended in dichloromethane(1.25 l) and stirred at 8° C. Sulfuryl chloride(146.8 ml; 1.83 mole) was added dropwise over 1 hour and during this addition the temperature of the reaction mixture was maintained between 10 and 15° C. As the sulfuryl chloride was added the suspended particles dissolved and a dark oil began to fall out of solution. The resultant two-phase mixture was stirred at 10° C. for 15 minutes. The mixture was cooled to below 10° C. and quenched by careful addition of aqueous potassium carbonate solution (367.3 g, 2.66 mole, of potassium carbonate in 1 l of water). The two phases were separated and the aqueous layer extracted with dichloromethane (600 ml+400 ml). The combined organic layers were dried over anhydrous magnesium sulfate, filtered and the filtrate was concentrated in vacuo. The residue was slurried in hexane (~500 ml) for 1 hour, filtered and dried to give 5-amino-4-chloro-3-methylisothiazole as a red-brown-solid (228.7 g, 93%), m.p. 69–71° C.

$^1$H NMR (CDCl$_3$) δ: 2.3 (3H,s); 4.6(2H, bs)ppm.

Step 2
Preparation of methyl(4-hydroxyphenyl)acetate

Hydrogen chloride was bubbled through a solution of (4-hydroxyphenyl) acetic acid (25 g, 0.16 mole) in methanol (100 ml) at room temperature. An exotherm resulted in the solution refluxing for about 10 minutes. The mixture was allowed to cool to room temperature and the solvent was evaporated in vacuo to afford methyl(4-hydroxyphenyl)acetate as a yellow oil (27.5 g) which crystallised on seeding, m.p. 46–52° C.

$^1$H NMR (CDCl$_3$) δ: 3.57(2H,s); 3.71(3H,s); 6.0(1H,b); 6.76 (2H,m); 7.10(2H,m)ppm.

Step 3
Preparation of methyl(4-hydroxy-3-nitrophenyl)acetate

Nitric acid (69% by weight, 16M, 20 ml) was added dropwise to a solution of methyl (4-hydroxyphenyl)acetate [from step 2] (50.0 g, 0.3 mole) in acetic acid (500 ml), maintaining the temperature of the reaction below 15° C. by external cooling. (An induction period was observed for this reaction.) Once gas chromatographic analysis had confirmed that the reaction was complete, the mixture was carefully quenched into water (2l) with vigorous stirring. An emulsion formed which subsequently crystallised. After filtration, washing with water and drying, the desired product was obtained as a yellow powder.

$^1$H NMR (CDCl$_3$) δ: 3.63(2H,s); 3.72(3H,s); 7.14(1H,d); 7.52(1H,dd); 8.02(1H,d); 10.5(1H,s)ppm.

Step 4
Preparation of methyl(3-amino-4-hydroxyphenyl)acetate

Methyl(4-hydroxy-3-nitrophenyl)acetate [from step 3] (48.9 g, 0.23 mole) and 5% palladium on carbon were suspended in methanol and the resulting mixture was hydrogenated until all the starting material had been consumed. The reaction mixture was filtered to remove the catalyst and the filtercake was washed with methanol. The combined filtrate and washings were concentrated in vacuo, affording methyl(3-amino-4-hydroxyphenyl)acetate as a solid (41.0 g).

$^1$H NMR (d$_6$-DMSO) δ: 3.51(2H,s); 4.45(2H,b); 6.20(1H, dd); 6.40(1H,d); 6.49(1H,d); 8.87(1H,b)ppm.

Step 5
Preparation of methyl[3-(2,2-dimethylpropionamido)-4-hydroxyphenyl]acetate Sodium hydrogen carbonate (19 g, 0.23 mol) was suspended in 1,2-dimethoxyethane (180 ml), and methyl(3-amino-4-hydroxyphenyl)acetate [from step 4] (26.3 g, 0.145 mole) was added. To this mixture was added, dropwise, a solution of tert-butylacetyl chloride in 1,2-dimethoxyethane (45 ml), over 2 hours. Once the addition was complete, the mixture was stirred at room temperature for 1 hour. The mixture was filtered, the inorganic solid washed with ethyl acetate (3×50 ml) and the filtrate and washings were combined and concentrated. Trituration of the product with hexane gave methyl [3-(2,2-dimethylpropionamido)-4-hydroxyphenyl]acetate (40.1 g) as an off-white solid, m.p. 112–113° C.

$^1$H NMR (CDCl$_3$) δ: 1.1(9H,s); 2.30(2H,s); 3.51(2H,s); 3.70(3H,s); 6.9–7.0(3H,m); 7.55(1H,b); 8.95(1H,b)ppm.

Step 6
Preparation of methyl[(2,2-dimethylpropyl)benzoxazol-5-yl]acetate para-Toluenesulphonic acid (1.5 g) in toluene (120 ml) was stirred and heated to reflux with a Dean & Stark™ assembly fitted to remove water. After 1 hour at reflux the solution was cooled to ~80° C. and methyl[3-(2,2-dimethylpropionamido)-4-hydroxyphenyl]acetate [from step 5] (20.0 g, 0.07 mole) was added portionwise. The reaction mixture was then heated at reflux for 6 hours, cooled, diluted with hexane (200 ml) and filtered through a plug of silica gel, eluting with ethyl acetate. The filtrate was evaporated in vacuo to give methyl[(2,2-dimethylpropyl)benzoxazol-5yl]acetate (17.5 g) as an oil.

$^1$H NMR (CDCl$_3$) δ: 1.1(9H,s); 2.8(2H,s); 3.7(3H,s); 3.74(2H,s); 7.4(3H,m)ppm.

Step 7
Preparation of [(2,2-dimethylpropyl)benzoxazol-5-yl]acetic Acid

Methyl[(2,2-dimethylpropyl)benzoxazol-5-yl]acetate [from step 6] (5.00 g, 0.0185 mole) was dissolved in methanol (5 ml) and then a solution of sodium hydroxide (0.81 g, 0.0204 mole) in water (5 ml) was added slowly over 20 minutes, maintaining the temperature below 25° C. by external cooling. Once the addition was complete, the mixture was allowed to stir at room temperature for 1 hour. The reaction mixture was poured slowly into water (50 ml) and concentrated hydrochloride acid was added until the pH of the mixture was below pH6. The mixture was stirred for 1 hour then filtered and the solid was washed thoroughly with water and dried. Trituration with hexane gave [(2,2-dimethylpropyl)benzoxazol-5yl]acetic acid (4.51 g) as a white solid, m.p. 108–109° C.

$^1$H NMR (CDCl$_3$) δ: 1.05(9H,s); 2.80(2H,s); 3.77(2H,s); 7.42(3H,m)ppm.

Step 8
Preparation of N-(4-chloro-3-methylisothiazol-5-yl)-[2-(2,2-dimethylpropyl)benzoxazol-5-yl]acetamide

[2-(2,2-Dimethylpropyl)benzoxazol-5-yl]acetic acid [from step 7] (0.800 g, 0.003 mole) was suspended in dichloromethane (10 ml) and N,N-dimethylformamide (one drop) and oxalyl chloride (0.451 g, 0.004 mole) were added sequentially. The mixture was stirred for 2 hour and then the solvent was removed in vacuo. The residue was taken up in xylene (10 ml), 5-amino-4-chloro-3-methylisothiazole [from step 1] (0.829 g, 0.006 mole) was added and then the mixture was heated under reflux for 2 hours. The mixture was cooled to room temperature, diluted with ethyl acetate and washed with brine. The organic solution was dried over anhydrous magnesium sulfate, filtered and the filtrate was evaporated in vacuo. The residue was further purified by flash column chromatography on silica gel, eluting with a 2:1 mixture of hexane:ethyl acetate, to give N-(4-chloro-3-methylisothiazol-5-yl)-[2-(2,2-dimethylpropyl)benzoxazol-5-yl]acetamide (0.325 g) as a pale orange solid, m.p. 144–145° C.

$^1$H NMR (CDCl$_3$) δ: 1.1(9H,s); 2.35(3H,s); 2.85(2H,s); 3.95(2H,s); 7.25(1H,dd); 7.55(1H,d); 7.65(1H,d); 8.1(1H,b) ppm.

EXAMPLE 2

This Example illustrates the preparation of Compound No. 7 of Table No. 11.

N-(4-Chloro-3-methylisothiazol-5-yl)-(2-[2,2-dimethylpropyl]benzoxazol-5-yl)acetamide [prepared as in Example 1] (0.38 g) in dry N,N-dimethylformamide (3 ml) under an atmosphere of nitrogen was stirred at ambient temperature then sodium hydride (0.200 g, 80% dispersion in mineral oil) was added. The mixture was stirred for 15 minutes then chloromethyl pivalate (0.166 g) was added. The mixture was heated to 80–85° C. for 3 hours, further sodium hydride (0.100 g, 80% dispersion in mineral oil) was added, the mixture was heated for a further 3 hours and then cooled to ambient temperature. The solution was diluted with water (50 ml), acidified with dilute hydrochloric acid to give a fawn solid which was filtered from solution and then sucked to dryness. The solid was fractionated by HPLC (silica, hexane/ethyl acetate at 5:1 by volume) to give the required product as a colourless solid (0.050 g).

EXAMPLE 3

This Example illustrates the preparation of Compound No. 7 of Table No. 22.

To a stirred solution of N-(4-chloro-3-methylisothiazol-5-yl)-(2-[2,2-dimethylpropyl]benzoxazol-5-yl)acetamide (0.21 g) [prepared as in Example 1] in dry N,N-dimethylformamide (2.5 ml) under an atmosphere of nitrogen at ambient temperature was added sodium hydride (0.21 g, 80% dispersion in mineral oil). The mixture was stirred for 0.5 hour then 1-methylethylsulfenyl chloride (0.078 g) was added dropwise. The mixture was stirred for 2 hours then the solvent was evaporated under reduced pressure. The residue was fractionated by chromatography (silica, hexane/ethyl acetate 2:1 by volume) to give the required product (0.021 g), as a pale yellow gun.

EXAMPLE 4

This Example illustrates the preparation of Compound No. 7 of Table No. 10.

To a stirred solution of N-(4-chloro-3-methylisothiazol-5-yl)-(2-[2,2-dimethylpropyl]benzoxazol-5-yl)acetamide (0.25 g) [prepared as in Example 1] in dry N,N-diethylformamide (2.5 ml) under an atmosphere of nitrogen at ambient temperature was added sodium hydride (0.21 g, 80% dispersion in mineral oil). The mixture was stirred for 0.2 hour, morpholine sulfenyl chloride [ref. EP 216423] (0.11 g) was added dropwise over 0.2 hour and then the mixture was stirred for a further 4.5 hours. The solvent was evaporated under reduced pressure and the residue was fractionated by chromatography (silica, hexane/ethyl acetate 2:1 by volume) to give the required product, 0.057 g, as a yellow solid.

EXAMPLE 5

This Example illustrates the preparation of Compound No. 7 of Table No. 14.

N-(4-Choro-3-methylisothiazol-5-yl)-[2-(2,2-dimethylpropyl)benzoxazol-5-yl]acetamide (2.5 g, 0.0066 mole) [prepared as in Example 1] and N,N-dimethylformamide dimethylacetal (1.5 g, 0.013 mole) were added to a mixture of N,N-dimethylformamide (5 ml) and toluene (20 ml) and the resulting mixture was heated to 110° C. for 4 hours. The mixture as cooled to room temperature and the solvent was evaporated in vacuo. The residue was taken up in ethyl acetate and washed sequentially with brine and water, dried over anhydrous magnesium sulfate, filtered and the filtrate evaporated in vacuo. The residue was further purified by flash column chromatography, eluting with ethyl acetate:hexane at 1:1 by volume. Further flash column chromatography, eluting with ethyl acetate:dichloromethane at 1:9 by volume gave N-(4-chloro-3-methylisothiazol-5-yl)-α-[(dimethylamino)methylene]-[2-(2,2-dimethylpropyl)benzoxazol-5-yl]acetamide (0.78 g) as a single geometrical isomer.

EXAMPLE 6

This Example illustrates the preparation of Compound No. 7 of Table No. 15.

A mixture of N-(4-chloro-3-methylisothiazol-5-yl)-α-[(dimethylamino)methylene]-[2-(2,2-dimethylpropyl) benzoxazol-5-yl]acetamide (0.20 g, 0.00046 mole) [from Example 5] and ethylamine hydrochloride (0.0225 g, 0.0028 mole) in tetrahydrofuran (4 ml) and water (1 ml) was heated for 24 hours at 60° C. The mixture was cooled to room temperature, the solvent was evaporated in vacuo and the residue partitioned between ethyl acetate and saturated aqueous sodium bicarbonate solution. The organic extract was dried over anhydrous magnesium sulfate, filtered and the filtrate was evaporated in vacuo. Further purification by flash column chromatography, eluting with ethyl acetate-:hexane at 2:3 by volume, gave N-(4-chloro-3-methylisothiazol-5-yl)-α-[(ethylamino)methylene]-[2-(2,2-dimeth-ylpropyl)benzoxazol-5-yl]acetamide as a colourless solid (0.17 g). Analysis by $^1$H NMR showed the product comprised a mixture of E- and Z-isomers.

By similar procedures, Compound No. 7 of Table No. 16 (E- and Z-isomers), Compound No. 7 of Table No. 17 and Compound No. 7 of Table No. 19 (E- and Z-isomers) were each made individually.

EXAMPLE 7

This Example illustrates the preparation of Compound No. 7 of Table No. 1.
Step 1
Preparation of methyl 2-[2-(2,2-dimethylpropyl) benzoxazol-5-yl]propionate Methyl[2-(2,2-dimethylpropyl)benzoxazol-5-yl]acetate (8.0 g, 0.031 mole) [prepared as in Example 1, step 6] was dissolved in dry tetrahydrofuran (200 ml) and the solution was cooled to −78° C. Lithium diisopropylamide (2.0 molar solution in tetrahydrofuran/ethylbenzene/heptane, 15.4 ml, 0.031 mole) was added dropwise, maintaining the reaction temperature below −60° C., and once the addition was complete the mixture was stirred for 1 hour. Methyl iodide (38.4 g, 0.27 mole) was added dropwise, at such a rate that the reaction temperature was maintained below −60° C., and once the addition was complete the mixture was stirred for 1 hour. The cooling bath was removed and the mixture was stirred for 3 hours, allowed to warm to room temperature, at which it was kept overnight. The reaction was quenched with water, acidified with dilute aqueous hydrochloric acid and extracted with ethyl acetate. The organic extract was dried over anhydrous magnesium sulfate, filtered and the filtrate evaporated in vacuo. Further purification by flash column chromatography, eluting with ethyl acetate:hexane at 1:7 by volume gave methyl 2-[2-(2,2-methylpropyl)benzoxazol-5-yl]propionate (6.6 g).

$^1$H NMR (CDCl$_3$) δ: 1.08(9H,s); 1.54(3H,d); 2.81(2H,s); 3.6 (3H,s); 3.84(1H,q); 7.26(1H,dd); 7.43(1H,d); 7.62(1H, d)ppm.
Step 2
Preparation of N-(4-Chloro-3-methylisothiazol-5-yl)-2-[2-(2,2-dimethylpropyl)benzoxazol-5-yl]propionamide Lithium diisopropylamide (2.0 molar solution in tetrahydrofuran/ethylbenzene/heptane, 1.46 ml, 0.0029 mole) was added dropwise to a chilled solution of 5-amino-4-chloro-3-methylisothiazole (0.44 g, 0.0029 mole) [preparation as in Example 1, Step 1] in tetrahydrofuran (20 ml) and the solution was stirred at 0° C. for 1 hour. A solution of methyl 2-[2-(2,2-dimethylpropyl)benzoxazol-5-yl]propionate (0.80 g, 0.0029 mole) [from previous step] in tetrahydrofuran (5 ml) was added dropwise and once the addition was complete the mixture was stirred at 0° C. for 30 minutes and then at room temperature overnight. The mixture was quenched with water, acidified with aqueous ammonium chloride solution and extracted with ethyl acetate. The organic extract was dried over anhydrous magnesium sulfate, filtered and the filtrate evaporated in vacuo. Further purification by flash column chromatography, eluting with ethyl acetate:hexane at 1:4 by volume gave N-(4-chloro-3-methylisothiazol-5-yl)-2-[2-(2, 2-dimethylpropyl)benzoxazol-5-yl]propionamide as a colourless solid.

By similar procedures, Compound No. 7 of Table No. 3, Compound No. 7 of Table No. 4 and Compound No. 7 of Table No. 18 were each made individually.

EXAMPLE 8

This Example illustrates the preparation of Compound No. 7 of Table No. 5.
Step 1
Preparation of methyl[2-(2,2-diethylpropyl)benzoxazol-5-yl]fluoroacetate A solution of lithium diisopropylamide (2.0M solution in tetrahydrofuran/ethylbenzene/heptane, 3.85 ml, 0.0077 mol) was added dropwise to a solution of methyl [2-(2,2-diethylpropyl)benzoxazol-5-yl]acetate (2.0 g, 0.0077 mol) in tetrahydrofuran (40 ml) at −78° C. under a nitrogen atmosphere and the mixture was stirred at −78° C. for 1 hour. A solution of N-fluorobenzenesulfonimide (2.42 g, 0.0077 mol) in tetrahydrofuran (10 ml) was added dropwise and the mixture was stirred at −70° C. for a further 1 hour. The cooling bath was removed and the mixture allowed to warm to room temperature over a period of 20 hours. The reaction mixture was diluted with water, acidified with dilute aqueous hydrochloric acid and extracted with ethyl acetate. The organic extracts were combined, washed with water, dried over anhydrous magnesium sulfate, filtered and the filtrate was evaporated in vacuo. The residue was purified by flash column chromatography on silica gel, eluting with ethyl acetate:dichloromethane 5:95, and was further purified by column chromatography on silica gel, eluting with ethyl acetate:hexane 1:3, to give methyl [2-(2,2-dimethylpropyl) benzoxazol-5-yl]fluoroacetate (1.4 g).

$^1$H NMR (CDCl$_3$) δ: 1.08(s,9H); 2.83(s,2H); 3.79(s,3H); 5.90(d,1H); 7.43(dd,1H); 7.53(d,1H); 7.80(d,1H)ppm.
Step 2

5-Amino-4-chloro-3-methylisothiazole (0.41 g, 0.0028 mol) was added to a suspension of sodium methoxide (0.34 g, 0.0063 mol) in tetrahydrofuran (5 ml) and the mixture was stirred at room temperature for 30 minutes. A solution of methyl[2-(2,2-dimethylpropyl)benzoxazol-5-yl] fluoroacetate (0.70 g, 0.0025 mol) in tetrahydrofuran (3 ml) was added dropwise and the mixture was stirred at room temperature for 3 days. The mixture was diluted with water, neutralised with saturated aqueous ammonium chloride solution and extracted with ethyl acetate. The organic extracts were combined, dried over anhydrous magnesium sulfate, filtered and the filtrate was evaporated in vacuo. The residue was purified by flash column chromatography on silica gel, eluting with ethyl acetate:hexane 1:1, to give the desired product (0.48 g).

EXAMPLE 9

This Example illustrates the preparation of Compound No. 8 of Table No. 1.
Step 1
Preparation of methyl 4-methoxyphenylacetate A solution of methyl 4-hydroxyphenylacetate (25.0 g, 0.147 mol) in tetrahydrofuran (50 ml) was added dropwise to a stirred suspension of sodium hydride (4.45 g of an 80% dispersion in oil, 0.147 mol) in tetrahydrofuran (150 ml) and the mixture was stirred for 90 minutes. A solution of methyl iodide (20.9 g, 0.47 mol) in tetrahydrofuran (50 ml) was added dropwise and the mixture was stirred overnight at room temperature. The solvent was removed in vacuo, and the residue was partitioned between water and ethyl acetate. The organic extract was washed with brine, dried over anhydrous magnesium sulfate, filtered and the filtrate was evaporated in vacuo. The residue was purified by chromatography on silica gel, eluting with ethyl acetate:hexane 1:9, to give methyl 4-methoxyphenylacetate (22.0 g) as a colourless oil.

$^1$H NMR (CDCl$_3$) δ: 3.57(s,2H); 3.68(s,3H); 3.8(s,3H); 6.87(m,2H); 7.20(m,2H)ppm.

Step 2

Preparation of methyl 2-(4-methoxyphenyl)propionate

A solution of lithium diisopropylamide (2.0M solution in tetrahydrofuran/ethylbenzene/heptane, 34.0 ml, 0.0667 mol) was added dropwise to a solution of methyl 4-methoxyphenylacetate (12.0 g, 0.0667 mol) in tetrahydrofuran (150 ml) at −70° C. under a nitrogen atmosphere and the mixture was stirred at −70° C. for 1 hour. A solution of methyl iodide (9.5 g, 0.0667 mol) in tetrahydrofuran (20 ml) was added dropwise and the mixture was stirred at −70° C. for a further 1 hour. The cooling bath was removed and the mixture was allowed to warm to room temperature overnight. The reaction was quenched with water, acidified with dilute aqueous hydrochloric acid and extracted with ethyl acetate. The organic extract was washed with brine, dried over anhydrous magnesium sulfate, filtered and the filtrate was evaporated in vacuo. The residue was purified by flash column chromatography on silica gel, eluting with ethyl acetate:hexane 1:9, to give methyl 2-(4-methoxyphenyl) propionate (8.8 g) as a colourless oil.

$^1$H NMR (CDCl$_3$) δ: 1.48(d,3H); 3.67(s,3H); 3.69(q,1H); 3.79(s,3H); 6.86(m,2H); 7.22(m,2H)ppm.

Step 3

Preparation of N-(4-chloro-3-methylisothiazol-5-yl)-2-(4-methoxyphenyl)propionanide 5-Amino-4-chloro-3-methylisothiazole (7.4 g, 0.050 mol) was added to a suspension of sodium methoxide (6.1 g, 0.112 mol) in tetrahydrofuran (160 ml) and the mixture was stirred at room temperature for 20 minutes. A solution of methyl 2-(4-methoxyphenyl)propionate (8.8 g, 0.045 mol) in tetrahydrofuran (40 ml) was added dropwise and the mixture was stirred for 3 hours at room temperature. The reaction was quenched with water, acidified with dilute aqueous hydrochloric acid and extracted with ethyl acetate. The organic extract was washed with brine, dried over anhydrous magnesium sulfate, filtered and the filtrate was evaporated in vacuo. The residue was purified by flash column chromatography on silica gel, eluting with ethyl acetate:dichloromethane 2.5:97.5, to give N-(4-chloro-3-methylisothiazol-5-yl)-2-(4-methoxyphenyl)propionamide (12.5 g) as a colourless solid.

$^1$H NMR (CDCl$_3$) δ: 1.63(d,3H); 2.35(s,3H); 3.83(s,3H); 3.83(q,1H); 6.95(m,2H); 7.28(m,2H); 7.98(b,1H)ppm.

Step 4

Preparation of N-(4-chloro-3-methylisothiazol-5-yl)-2(4-hydroxyphenyl)propionamide Boron tribromide (1.0 M solution in dichloromethane, 110 ml, 0.11 mol) was added dropwise to a stirred solution of N-(4-chloro-3-methylisothiazol-5-yl)-2-(4-methoxyphenyl)propionamide (125 g, 0.040 mol) in dichloromethane (200 ml) at −70° C. Once the addition was complete the cooling bath was removed and the mixture was allowed to warm to room temperature overnight. The mixture was cooled to 0° C. and excess methanol added cautiously. The solvent was evaporated in vacuo, and the residue was partitioned between ethyl acetate and brine. The organic layer was dried over anhydrous magnesium sulfate, filtered and the filtrate was evaporated in vacuo to give N-(4-chloro-3-methylisothiazol-5-yl)-2-(4-hydroxyphenyl) propionamide (11.8 g), which was used without further purification in the next step.

$^1$H NMR (CDCl$_3$) δ: 1.62(d,3H); 2.38(s,3H); 3.83(q,1H); 5.51(b,1H); 6.90(m,2H); 7.23(m,2H); 7.98(b,1H)ppm.

Step 5

Preparation of N-(4-chloro-3-methylisothiazol-5-yl)-2-(4-hydroxy-3-nitrophenyl)propionamide Ferric nitrate nonahydrate (16.16 g, 0.04 mol) was added to a solution of N-(4-chloro-3-methylisothiazol-5-yl)-2-(4-hydroxyphenyl)propionamide (11.8 g, 0.04 mol) in ethanol (100 ml) and the mixture was stirred and warmed at 50 ° C. for 2½ hours. The mixture was cooled to room temperature and the solvent removed in vacuo. The residue was partitioned between 2M aqueous hydrochloric acid and ethyl acetate and the organic phase was dried over anhydrous magnesium sulfate, filtered and the filtrate was evaporated in vacuo. Purification by flash column chromatography on silica gel, eluting with ethyl acetate:dichloromethane 5:95, gave N-(4-chloro-3-methylisothiazol-5-yl)-2-(4-hydroxy-3-nitrophenyl)propionamide (11.1 g) as a yellow solid.

$^1$H NMR (CDCl$_3$) δ: 1.66(d,3H); 2.38(s,3H); 3.93(q,1H); 7.21(d,1H); 7.65(dd,1H); 8.10(d,1H); 8.41(b,1H); 10.55(s, 1H)ppm.

Step 6

Preparation of N-(4-chloro-3-methylisothiazol-5-yl)-2-(3-amino-4-hydroxyphenyl)propionamide A mixture of N-(chloro-3-methylisothiazol-5-yl)-2-(4-hydroxy-3-nitrophenyl)propionamide (11.0 g, 0.0322 mol) and 3% platinum on carbon in N,N-dimethylformamide (100 ml) was hydrogenated at 15 bar (15×10$^5$ Nm$^{-2}$) for 6 hours at room temperature. The catalyst was removed by filtration and the filtrate evaporated in vacuo to give N-(4-chloro-3-methylisothiazol-5-yl)-2-(3-amino-4-hydroxyphenyl)propionamide (9.0 g) as an off-white solid, m.p.222–223° C.

$^1$H NMR (D$^6$-DMSO/CDCl$_3$) δ: 1.08(d,3H); 1.96(s,3H); 2.90(b,2H); 3.62(q,1H); 6.14(dd,1H); 6.30(m,2H); 8.33(b, 1H); 10.1(b,1H)ppm.

Step 7

Preparation of N-(4-chloro-3-methylisothiazol-5-yl)-2-[4-hydroxy-3-(3,3,3-trifluoropropionamido)phenyl] propionamide A mixture of N-(4-chloro-3-methylisothiazol-5-yl)-2-(3-amino-4-hydroxyphenyl)propionamide (0.65 g, 0.002 mol), 3,3,3-trifluoropropionic acid (0.267 g, 0.002 mol) and 1-(3-diethylaminopropyl)-3-ethylcarbodiimide hydrochloride (0.40 g, 0.002 mol) was stirred in N,N-dimethylacetamide (8 ml) at room temperature for 7 hours and was then allowed to stand at room temperature overnight. The reaction was quenched with water and extracted with ethyl acetate. The organic extract was washed with water, dried over anhydrous magnesium sulfate, filtered and the filtrate was evaporated in vacuo. The residue was purified by flash column chromatography on silica gel, eluting with ethyl acetate:hexane 1:1, to give N-(4-chloro-3-methylisothiazol-5-yl)-2-[4-hydroxy-3-(3,3,3-trifluoropropionamido)phenyl] propionamide (0.62 g) as a white solid.

$^1$H NMR (CDCl$_3$) δ: 1.54(d,3H); 2.37(d,3H); 3.36(q,2H); 3.96 (q,1H); 6.98(d,1H); 7.04(dd,1H); 7.86(d,1H)ppm.

Step 8

A mixture of N-(4-chloro-3-methylisothiazol-5-y)-2-[4-hydroxy-3-(3,3,3-trifluoropropionamido)phenyl]

propionamide (0.58 g, 0.0014 mol) and para-toluenesulfonic acid (0.02 g) in 1,1,2,2-tetrachloroethane was heated at reflux for 26 hours. The mixture was cooled to room temperature and the solvent evaporated in vacuo. The residue was purified by flash column chromatography on silica gel, eluting with ethyl acetate:hexane 35:65, to give the desired product (0.255 g) as a pale yellow solid.

EXAMPLE 10

This Example illustrates the preparation of Compound No. 78 of Table No. 1.

A solution of N,O-bis(trimethylsilyl)acetamide (0.141 g, 0.000 mol) in dichloromethane (1 ml) was added to a solution of N-(4-chloro-3-methylisothiazol-5-yl)-2-[2-(2,2, 2-trifluoroethyl)benzoxazol-5-yl]propionamide (0.236 g, 0.0006 mol) in dichloromethane (4 ml) and the mixture was stirred at room temperature for 15 minutes. Chloromethylethyl ether (0.11 g, 0.001 mol) was added and stirring was continued for 24 hours. Further quantities of N,O-bis (trimethylsilyl)acetamide (0.141 g, 0.0007 mol) and chloromethylethyl ether (0.11 g, 0.001 mol) were added and stirring was continued for 6 hours. The reaction was quenched with saturated aqueous sodium bicarbonate solution and extracted with ethyl acetate. The organic extract was washed with brine, dried over anhydrous magnesium sulfate, filtered and the filtrate was evaporated in vacuo. Purification by flash column chromatography on silica gel, eluting initially with ethyl acetate:hexane 1:4 and then with ethyl acetate:hexane 45:55, gave the desired product (0.04 g) as an oil.

EXAMPLE 11

This Example illustrates the preparation of Compound No. 10 of Table No. 1.
Step 1
Preparation of methyl(3-heptafluorobutyramido-4-hydroxyphenyl)acetate Sodium bicarbonate (51 g, 0.607 mol) was suspended in 1,2-dimethoxyethane (180 ml), and methyl(3-amino-4-hydroxyphenyl)acetate (58.26 g, 0.32 mol) was added, followed by a further quantity of 1,2-dimethoxyethane (75 ml). To this mixture was added, dropwise, a solution of heptafluorobutyryl chloride (112.5 g, 0.48 mol) in 1,2-dimethoxyethane (140 ml), at such a rate that the reaction temperature was maintained at 19–20° C. Once the addition was complete, the mixture was stirred at room temperature for 1½ hours. The reaction mixture was filtered and the solid was taken up in ethyl acetate and washed with saturated aqueous bicarbonate solution and brine. The organic phase was dried over anhydrous magnesium sulfate, filtered and the filtrate was evaporated in vacuo. The residue was taken up in acetone (450 ml) and water (450 ml) was added. The mixture was stirred for 1½ hours, during which time an oil separated. The aqueous acetone was decanted and a further quantity (250 ml) of water was added to the oil. The mixture was stirred for 1 hour, during which time the desired product crystallised; it was collected by filtration, washed with water and dried to give methyl(3-heptafluorobutyramido-4-hydroxyphenyl)acetate (87.0 g).

$^1$H NMR (d$^6$-DMSO/CDCl$_3$) δ: 3.56(s,2H); 3.69(s,3H); 6.95(m,2H); 8.1(d,1H); 8.83(b,1H); 9.51(s,1H)ppm.
Step 2
Preparation of methyl(2-heptafluoropropylbenzoxazol-5-yl)acetate A mixture of methyl(3-heptafluorobutyramido-4-hydroxyphenyl)acetate (20.0 g, 0.053 mol) and para-toluenesulfonic acid (1.71 g) in toluene (150 ml) was heated at reflux (a Dean & Stark™ assembly was fitted to remove water) for 24 hours. The mixture was cooled to room temperature and the mixture was diluted with ethyl acetate (150 ml). The mixture was washed with saturated aqueous sodium bicarbonate solution and brine, dried over anhydrous magnesium sulfate, filtered and the filtrate was evaporated in vacuo. The residue was purified by column chromatography on silica gel, eluting with dichloromethane to give methyl (2-heptafluoropropylbenzoxazol-5-yl)acetate (12.9 g) as an off-white solid.

$^1$H NMR (CDCl$_3$) δ: 3.71(s,3H); 3.8(s,2H); 7.48(dd,1H); 7.63(d,1H); 7.8(d,1H)ppm.
Step 3
Preparation of methyl 2(2-heptafluoropropylbenzoxazol-5-yl)propionate A solution of lithium diisopropylamide (2.0M solution in tetrahydrofuran/ethyl benzene/heptane, 15.32 ml, 0.0306 mol) was added dropwise to a solution of methyl(2-heptafluoropropylbenzoxazol-5-yl)acetate (11.0 g, 0.0306 mol) in tetrahydrofuran (175 ml) at −70° C. under a nitrogen atmosphere and the mixture was stirred at −70° C. for 1 hour. A solution of methyl iodide (39.1 g, 0.275 mol) in tetrahydrofuran (25 ml) was added dropwise and the mixture was stirred at −70° C. for a further 1 hour. The cooling bath was removed and the mixture was allowed to warm to room temperature over a period of 3 hours. The reaction was quenched with water, acidified with dilute aqueous hydrochloric acid and extracted with ethyl acetate. The organic extract was washed with brine, dried over anhydrous magnesium sulfate, filtered and the filtrate was evaporated in vacuo to give methyl 2-(2-heptafluoropropylbenzoxazol-5-yl)propionate (11.6 g) as a reddish oil, which was used without further purification in the next step.

$^1$H NMR (CDCl$_3$) δ: 1.56(d,3H); 3.67(s,3H); 3.9(q,1H); 7.5(dd,1H); 7.62(d,1H); 7.82(d,1H)ppm.
Step 4
Preparation of 2-(2heptafluoropropylbenzoxazol-5-yl) propionic Acid A mixture of methyl 2-(2-heptafluoropropylbenzoxazol-5-yl)propionate (11.6 g, 0.0311 mol), hexamethyldisilane (6.81 g, 0.047 mol) and iodine (11.85 g, 0.047 mol) was stirred in refluxing toluene (110 ml) for 6 hours. The mixture was cooled to room temperature, diluted with ethyl acetate and washed sequentially with water, saturated aqueous sodium thiosulfate solution and brine. The organic phase was dried over anhydrous magnesium sulfate, filtered and the filtrate was evaporated in vacuo. The residue was purified by column chromatography on silica gel, eluting initially with dichloromethane and then with ethyl acetate:dichloromethane 1:4, to give 2-(2-heptafluoropropylbenzoxazol-5-yl)propionic acid (6.3 g).

$^1$H NMR (CDCl$_3$) δ: 1.6(d,3H); 3.9(q,1H); 7.52(dd,1H); 7.64(d,1H); 7.87(d,1H)ppm.
Step 5

Oxalyl chloride (4.46 g, 0.035 mol) was added dropwise to a solution of 2-(2-heptafluoropropylbenzoxazol-5-yl) propionic acid (6.3 g, 0.0176 mol) in dichloromethane (60 ml) and the mixture was stirred at room temperature overnight. The solvent was evaporated in vacuo and the residue was dissolved in 1,2-dichloroethane (70 ml) and warmed to reflux. A solution of 5-amino-4-chloro-3-methylisothiazole (3.12 g, 0.021 mol) in 1,2-dichloroethane (30 ml) was added dropwise over 30 minutes to the refluxing mixture and the mixture was heated at reflux for a further 5 hours. The mixture was cooled to room temperature and the solid was collected by filtration, washed with 1,2-dichloroethane and diethyl ether and dried to give the desired product (6.4 g).

Resolution of Enantiomers of Compound 10 of Table 1

Racemic N-(4-chloro-3-methylisothiazol-5-yl)-2-[(2-heptafluoropropyl)benzoxazol-5-yl]propionamide (0.05 g) was dissolved in 60 ml of 2-methylpentane:propan-2-ol 90:10 and loaded onto a Chiralcel OT™ column (0.46 cm×25 cm) in aliquots of ca.0.008 ml. The chromatographic system was equilibrated and run using a mobile phase of 2-methylpentane:propan-2-ol (95:5) at 2 ml/min and fractions were collected and assesed by analytical HPLC under the conditions described immediately above.

Enantiomer A (0.029 g) eluted first; enantiomer B (0.016 g) eluted second. Fractions containing mixtures of enantiomers were discarded.

EXAMPLE 12

This Example illustrates the preparation of Compound No. 80 of Table No. 1.

A solution of N,O-bis(trimethylsilyl)acetamide (0.50 g, 0.00245 mol) was added to a solution of N-(4-chloro-3-methylisothiazol-5-yl)-2-[2-heptafluoropropylbenzoxazol-5-yl]propionamide (1.00 g, 0.002 mol) in dichloromethane (10 ml) and the mixture was stirred at room temperature for 15 minutes. Chloromethylethyl ether (0.386 g, 0.004 mol) was added and stirring was continued for 48 hours. The reaction mixture was diluted with dichloromethane and poured into water. The organic phase was washed with brine, dried over anhydrous magnesium sulfate, filtered and the filtrate was evaporated in vacuo. The residue was purified by flash column chromatography on silica gel, eluting initially with ethyl acetate:hexane 4:1 and subsequently with a gradient elution to ethyl acetate:hexane 1:1, to give the desired product (0.057 g).

EXAMPLE 13

This Example illustrates the preparation of Compound No. 7 of Table No. 82.
Step 1
Preparation of N-(2-hydroxy-5-bromophenyl)-3,3-dimethylbutyramide A solution of tert-butylacetyl chloride (2.7 g, 0.020 mol) in diethyl ether (20 ml) was added dropwise to a solution of 2-amino-4bromophenol (3.8 g, 0.020 mol) and triethylamine (2.1 g, 0.020 mol) in diethyl ether (160 ml) and the mixture was stirred at room temperature for 3 hours. The mixture was filtered and the filtrate was evaporated in vacuo. Purification by flash column chromatography on silica gel, eluting initially with ethyl acetate:dichloromethane 1.5:98.5 and then with ethyl acetate:dichloromethane 2.5:97.5, gave N-(2-hydroxy-5-bromophenyl)-3,3-dimethylbutyramide (1.8 g).

$^1$H NMR (CDCl$_3$) δ: 1.12(s,9H); 2.32(s,2H); 6.90(d,1H); 7.17(d,1H); 7.22(dd,1H); 7.32(b,1H); 8.69(s,1H)ppm.
Step 2
Preparation of 2-(2,2-dimethylpropyl)-5-bromobenzoxazole A mixture of N-(2-hydroxy-5-bromophenyl)-3,3-dimethylbutyrade (1.75 g, 0.006 mol) and para-toluenesulfonic acid (0.05 g) was heated in refluxing 1,1,2,2-tetrachloroethane (40 ml) for 24 hours. The mixture was cooled to room temperature, the solvent removed in vacuo and the residue purified by flash column chromatography on silica gel, eluting with ethyl acetate:hexane 5:95, to give 2-(2,2-dimethylpropyl)-5-bromobenzoxazole (1.38 g).

$^1$H NMR (CDCl$_3$) δ: 1.08(s,9H); 2.22(s,2H); 7.38(d,1H); 7.41(dd,1H); 7.82(d,1H)ppm.

Step 3
Preparation of ethyl 3-[2-(2,2-dimethylpropyl)benzoxazol-5-yl]propenoate

A mixture of 2-(2,2-diethylpropyl)-5-bromobenzoxazole (0.60 g, 0.00225 mol), ethyl acrylate (1.08 g, 0.0108 mol), palladium acetate (0.051 g, 0.00023 mol), trintolylphosphine (0.135 g,0.0045 mol) and N,N-diisopropylethylamine (0.585 g, 0.0045 mol) was heated at 100° C. for 6 hours. The mixture was cooled to room temperature, diluted with water and extracted with ethyl acetate. The organic extracts were dried over anhydrous magnesium sulfate, filtered and the filtrate was evaporated in vacuo. The residue was purified by flash column chromatography on silica gel, eluting with ethyl acetate:dichloromethane 3:97, to give ethyl 3-[2-(2,2-dimethylpropyl)benzoxazol-5-yl]propenoate (0.634 g).

$^1$H NMR (CDCl$_3$) δ: 1.10(s,9H); 1.35(t,3H); 2.83(s,2H); 4.29(q,2H); 6.45(d,1H); 7.50(s,2H); 7.80(d,1H); 7.85(s,1H) ppm.
Step 4
Preparation of ethyl 3-[2-(2,2-dimethylpropyl)benzoxazol-5-yl]propenoate A solution of ethyl 3-[2-(2,2-diethylpropyl)benzoxazol-5-yl]propenoate (0.500 g, 0.00174 mol) in ethanol (30 ml) was hydrogenated at 4.0 bar ($4×10^5$ Nm$^{-2}$) over 5% Pd on C for 4 hours at room temperature and then at 5.5 bar ($5.5×10^5$ Nm$^{-2}$) for 6 hours. The catalyst was removed by filtration and the filtrate was evaporated in vacuo. The residue was purified by flash column chromatography on silica gel, eluting with ethyl acetate:dichloromethane 3:97, to give ethyl 3-[2-(2,2-dimethylpropyl)benzoxazol-5-yl] propanoate (0.465 g).

$^1$H NMR (CDCl$_3$) δ: 1.08(s,9H); 1.24(t,3H); 2.67(t,2H); 2.80(s,2H); 3.06(t,2H); 4.14(q,2H); 7.14(dd, 1H); 7.40(d, 1H); 7.51(d,1H)ppm.
Step 5

5-Amino-4-chloro-3-methylisothiazole (0.225 g, 0.00152 mol) was added to a suspension of sodium methoxide (0197 g, 0.00365 mol) in tetrahydrofuran (8 ml) and the mixture was stirred at room temperature for 20 minutes. A solution of ethyl 3-[2-(2,2-dimethylpropyl)benzoxazol-5-yl] propanoate (0.400 g, 0.00138 mol) in tetrahydrofuran (2 ml) was added dropwise and the mixture was then stirred at room temperature for 20 hours. The mixture was diluted with water, acidified with saturated aqueous ammonium chloride solution and extracted with ethyl acetate. The organic extracts were combined, washed with brine, dried over anhydrous magnesium sulfate, filtered and the filtrate was evaporated in vacuo. The residue was purified by flash column chromatography on silica gel, eluting with ethyl acetate:dichloromethane 15:85, to give the desired product (0.49 g).

By similar procedures, Compound No. 83 of Table No. 7 and Compound No. 86 of Table No. 7 were each made individually.

EXAMPLE 14

This Example illustrates the preparation of Compound No. 86 of Table No. 39.
Step 1
Preparation of methyl 4-fluoro-3-nitrophenylacetate 4-Fluoro-3-nitrophenylacetic acid (31.0 g, 0.156 mol) was added to a mixture of concentrated sulfuric acid (1.6 ml) and methanol (160 ml) and the mixture was stirred for 3 days at room temperature. Most of the solvent was removed in vacuo and the residue was partitioned between diethyl ether and water. The organic phase was washed with saturated aqueous sodium bicarbonate solution and brine, dried over anhydrous magnesium sulfate, filtered and the filtrate was evaporated in vacuo to give methyl 4-fluoro-3-nitrophenylacetate (27.2 g) as a yellow oil.

$^1$H NMR (CDCl$_3$) δ3.72(s,2H); 3.75(s,3H); 7.27(dd,1H); 7.58(m,1H); 8.01(dd,1H)ppm.

Step 2
Preparation of methyl 3-amino-4-fluorophenylacetate

Iron powder (8.1 g) was added to a solution of methyl 4-fluoro-3-nitrophenylacetate (27.24 g, 0.128 mol) in a mixture of concentrated hydrochloric acid (1.5 ml), isopropanol (265 ml) and water (26.5 ml) and the mixture was stirred at room temperature for 1 hour. A second portion of iron powder (8.1 g) was added and the mixture was heated to reflux for 1 hour. A further quantity of concentrated hydrochloric acid was added and the mixture was refluxed for a further 1 hour. The mixture was cooled to room temperature, filtered through a plug of Hyflo® diatomaceous earth and the filtrate was evaporated in vacuo to give methyl 3-amino-4-fluorophenylacetate (22.98 g) which was used without further purification in the next step.

Step 3
Preparation of methyl 4-fluoro-3-(3-methylbutyramido) phenylacetate

Isovaleryll chloride (2.93 ml, 2.90 g, 0.024 mol) was added, dropwise, to a chilled (ice-bath) solution of methyl 3-amino-4-fluorophenylacetate (4.00 g, 0.022 mol) in pyridine (16 ml) and, once the addition was complete, the cooling bath was removed and the reaction mixture was stirred at room temperature for 30 minutes. The mixture was diluted with water and extracted with ethyl acetate. The organic extract was washed with water, dried over anhydrous magnesium sulfate, filtered and the filtrate was evaporated in vacuo. Trituration with dichloromethane/hexane gave methyl 4-fluoro-3-(3-methylbutyramido)phenylacetate (4.88 g) as a pale brown solid.

$^1$H NMR (CDCl$_3$) δ: 1.03(d,6H); 2.22(m,1H); 2.26(s,2H); 3.6(s,2H); 3.69(s,3H); 6.98(m,1H); 7.03(dd,1H); 7.33(b,1H); 8.39(d,1H)ppm.

Step 4
Preparation of methyl[2-(2-methylpropyl)benzothiazol-5-yl]acetate 2,4-bis(4-Methoxyphenyl)-1,3-dithia-2,4-phosphetane-2,4-disulfide (7.39 g, 0.018 mol) was added, portionwise, to a solution of methyl 4-fluoro-3-(3-methylbutyramido) phenylacetate (4.88 g, 0.018 mol) in refluxing 1,2-dimethoxyethane (70 ml) and, once the addition was complete, the mixture was refluxed for 3 hours. The mixture was cooled to room temperature, poured into water and extracted with dichloromethane. The organic phase was dried over anhydrous magnesium sulfate, filtered and the filtrate was evaporated in vacuo. The residue was passed through a plug of silica gel, eluting with ethyl acetate:hexane 1:1, and fractions containing the desired product were combined and evaporated in vacuo. The residue (5.92 g) was taken up in N,N-dimethylacetamide (48 ml) and potassium carbonate (5.776 g, 0.042 mol) was added and then the mixture was heated to 110° C. for 2 hours. The mixture was cooled to room temperature, poured into water and extracted with dichloromethane. The organic extract was washed with brine, dried over anhydrous magnesium sulfate, filtered and the filtrate was evaporated in vacuo. The residue was further purified by flash column chromatography on silica gel, eluting with ethyl acetate:hexane 1:4, to give methyl[2-(2-methylpropyl)benzothiazol-5-yl]acetate (2.01 g).

$^1$H NMR (CDCl$_3$) δ1.07(d,6H); 2.23(m,1H); 3.00(d,2H); 3.71(s,3H); 3.78(s,2H); 7.29(dd,1H); 7.79(d,1H); 7.88(d,1H)ppm.

Step 5
Preparation of methyl 2-[2-(2-methylpropyl)benzothiazol-5-yl]propionate

A solution of lithium diisopropylamide (2.0M solution in tetrahydrofran/ethylbenzene/heptane, 2.09 ml, 0.0042 mol) was added, dropwise, to a solution of methyl[2-(2-methylpropyl)benzothiazol-5-yl]acetate (1.1 g, 0.0042 mol) in tetrahydrofuran (27 ml) at −78° C. under a nitrogen atmosphere and the mixture was stirred at below −60° C. for 1 hour. Methyl iodide (2.29 ml, 0.037 mol) was added, dropwise, and the mixture was stirred at below −60° C. for a further 1 hour. The cooling bath was removed and the mixture was allowed to warm to room temperature over a period of 1 hour. The mixture was diluted with water, acidified with 2M aqueous hydrochloric acid and extracted with ethyl acetate. The organic extract was dried over anhydrous magnesium sulfate, filtered and the filtrate evaporated in vacuo to give methyl 2-[2-(2-methylpropyl) benzothiazol-5-yl]propionate (1.15 g) which was used without further purification in the next step.

$^1$H NMR (CDCl$_3$) δ: 1.04(d,6H); 1.58(d,3H); 2.22(m,1H); 2.98(d,2H); 3.67(s,3H); 3.87(q,1H); 7.31(dd,1H); 7.79(d,1H); 7.91(d,1H)ppm.

Step 6
Preparation of N-(4-chloro-3-ethylisothiazol-5-yl)-2-[2-(2-methylpropyl)benzothiazol-5-yl]propionamide 5-Amino-4-chloro-3-ethylisothiazole (0.81 g, 0.005 mol) was added to a suspension of sodium methoxide (0.56 g, 0.010 mol) in tetrahydrofuran (5 ml) and the mixture stirred at room temperature for 25 minutes. A solution of methyl 2-[2-(2-methylpropyl)benzothiazol-5-yl]propionate (1.15 g, 0.004 mol) in tetrahydrofuran (4 ml) was added dropwise and the mixture stirred at room temperature for 1½ hours. The mixture was diluted with saturated aqueous ammonium chloride solution and extracted with dichloromethane. The organic extract was dried over anhydrous magnesium sulfate, filtered and the filtrate evaporated in vacuo. Trituration with diethyl ether gave the desired product (1.06 g).

EXAMPLE 15

This Example illustrates the preparation of Compound No. 156 of Table No. 39.

A mixture of N,O-bis(trimethylsilyl)acetamide (0.533 ml, 0.439 g, 0.0022 mol), N-(4-chloro-3-ethylothiazol-5-yl)-2-[2-(2-methylpropyl)benzothiazol-5-yl]propionamide (0.800 g, 0.002 mol) and chloromethylethyl ether (0.365 ml, 0.358 g, 0.0038 mol) in dichloromethane (10 ml) was stirred at room temperature for 5½ hours. The reaction mixture was diluted with dichloromethane and washed with saturated aqueous sodium bicarbonate solution. The organic phase was dried over anhydrous magnesium sulfate, filtered and the filtrate was evaporated in vacuo. The residue was purified by column chromatography on silica gel, eluting with ethyl acetate:hexane 1:4, to give the desired product (0.278 g).

EXAMPLE 16

This Example illustrates the preparation of Compound No. 7 of Table No. 6.

Step 1
Preparation of methyl 2-[2-(2,2-dimethylpropyl) benzoxazol-5-yl]-2-fluoropropionate A solution of lithium diisopropylamide (2.0M solution in tetrahydrofuran/ethylbenzene/heptane, 4.55 ml, 0.009 mol) was added, dropwise, to a solution of methyl 2-[2-(2,2-dimethylpropyl)benzoxazol-5-yl]propionate (2.5 g, 0.009 mol) in tetrahydrofran (65 ml) at −70° C. under a nitrogen atmosphere and the mixture was stirred at −70° C. for 1 hour. A solution of N-fluorobenzensulfonimide (2.9 g. 0.009 mol) in tetrahydrofuran (15 ml) was added and the mixture was stirred at −70° C. for a further 1 hour. The cooling bath was removed and the reaction mixture was allowed to warm to room temperature, with stirring over 1½ hours. The mixture was quenched with water, acidified with dilute aqueous hydrochloric acid and extracted with ethyl acetate. The organic extract was washed with brine, dried over anhydrous magnesium sulfate, filtered and the filtrate was evaporated in vacuo. The residue was purified by flash column chromatography on silica gel, eluting with ethyl acetate:dichloromethane 1:99, to give methyl 2-[2-(2,2-dimethylpropyl) benzoxazol-5-yl]-2-fluoropropionate (2.06 g).

$^1$H NMR (CDCl$_3$) δ: 1.08(s,9H); 2.00(d,3H); 2.82(s,2H); 3.78(s,3H); 7.48(m,2H); 7.74(d,1H)ppm.

Step 2
Preparation of N-(4-chloro-3-methylisothiazol-5-yl)-2-[2-(2,2-dimethylpropyl)benzoxazol-5-yl]-2-fluoropropionamide 5-Amino-4-chloro-3-methylisothiazole (0.28 g, 0.00188 mol) was added to a suspension of sodium methoxide (0.24 g, 0.004 mol) in tetrahydrofuran (6 ml) and the mixture was stirred at room temperature for 20 minutes. A solution of methyl 2-[2-(2,2-dimethylpropyl)benzoxazol-5-yl]-2-fluoropropionate (0.50 g, 0.00171 mol) in tetrahydrofuran (2 ml) was added, dropwise, and the mixture was stirred at room temperature for 3 hours. The mixture was diluted with water, acidified with saturated aqueous ammonium chloride solution and extracted with ethyl acetate. The organic extract was dried over anhydrous magnesium sulfate, filtered and the filtrate was evaporated in vacuo. The residue was purified by flash column chromatography on silica gel, eluting with ethyl acetate:hexane 12:88, to give the desired product (0.575 g) as a pale yellow gum.

EXAMPLE 17

This Example illustrates the pesticidal/insecticidal properties of compounds of formula (I). The activities of individual compounds of formula (I) were determined using a variety of pests. The pests were treated with a liquid composition containing 500 parts per million (ppm) by weight of a compound of formula (I). Each composition was made by dissolving the compound in an acetone and ethanol (50:50 by volume) mixture and diluting the solution with water containing 0.05% by volume of a wetting agent, SYNPERONIC NP8, until the liquid composition contained the required concentration of the compound. SYNPERONIC is a registered trade mark.

The test procedure adopted with regard to each pest was essentially the same and comprised supporting a number of the pests on a medium, which was usually a substrate, a host plant or a foodstuff on which the pests feed, and treating either or both the medium and the pests with a composition. Pest mortality was assessed usually between two and five days after treatment.

In each test against peach potato aphids (*Myzus persicae*), Chinese cabbage leaves were infested with aphids, the infested leaves were sprayed with a test composition and pest mortality was assessed after three days.

Similar tests were conducted against, independently, two-spotted spider mites (*Tetranychus urticae*), fruit flies (*Drosophila melanogaster*), tobacco budworms (*Heliothis virescens*), diamond back moth (*Plutella xylostella*) and corn root worm (*Diabrotica balteata*).

Tests were also conducted against root knot nematodes (*Meloidogyne incognita*) using an in vitro test in which nematodes were suspended in a liquid composition which had been prepared as described above except that it contained a concentration of 12.5 ppm by weight of a compound of formula (I) and it contained no SYNPERONIC NP8.

Results from these tests are displayed in Table 104, in which each mortality (score) is designated as 9, 5 or 0 wherein 9 indicates 80–100% mortality, 5 indicates 40–79% mortality represents less than 40% mortality; and Dm represents *Drosophila melanogaster*; Mp represents *Myzus persicae*, Hv represents *Heliothis virescens*; Px represents *Plutella xylostella*, represents *Tetranychus urticae*; Db represents *Diabrotica balteata*; and Mi represents *Meloidogyne incognita*.

TABLE 104

| Table Number | Compound Number | Dm | Mp | Hv | Px | Tu | Db | Mi |
|---|---|---|---|---|---|---|---|---|
| 1 | 6 | 0 | 0 | | 9 | | 9 | 0 |
| 1 | 7 | | 5 | | | | | |
| 1 | 8 | 0 | 5 | 9 | 9 | | 9 | 0 |
| 1 | 10 | 0 | 0 | 9 | | | 5 | 0 |
| 1 | 76 | 9 | 9 | 5 | 9 | | 9 | 5 |
| 1 | 77 | 0 | 9 | 9 | 9 | | 9 | 0 |
| 1 | 78 | 9 | 9 | 9 | 9 | | 9 | 0 |
| 1 | 80 | 0 | 5 | 9 | 9 | | 9 | 0 |
| 1 | 81 | 9 | 9 | | 9 | | 9 | 0 |
| 1 | 86 | 9 | 9 | | 9 | | 9 | 0 |
| 1 | 87 | 9 | 9 | | 9 | | 9 | 0 |
| 1 | 88 | 0 | 9 | | 9 | | 9 | 0 |
| 1 | 90 | 0 | 0 | | 9 | | 9 | 0 |
| 1 | 156 | | 9 | | | | | 0 |
| 1 | 157 | 0 | 9 | 9 | 9 | | 9 | 0 |
| 1 | 159 | 9 | 9 | | 9 | | 9 | 0 |
| 1 | 160 | 9 | 9 | | 9 | | 9 | 0 |
| 2 | 10 | 0 | 5 | 9 | | | 9 | 0 |
| 2 | 90 | 0 | 0 | 9 | | | 0 | 0 |
| 4 | 7 | | 5 | | | | | |
| 5 | 6 | 9 | 9 | | 9 | | 9 | 9 |
| 5 | 7 | | 9 | | | 9 | | |
| 5 | 10 | 9 | 9 | 9 | 9 | | 9 | 0 |
| 5 | 77 | 0 | 9 | 5 | 9 | | 9 | 0 |
| 5 | 86 | 9 | 9 | 9 | 9 | | | |
| 5 | 87 | 9 | 9 | 9 | 9 | | | |
| 5 | 90 | 9 | 9 | | 9 | | 9 | 0 |
| 5 | 157 | 9 | 9 | 9 | 9 | | 9 | 55 |
| 5 | 160 | 0 | 9 | | 9 | | 9 | 0 |
| 6 | 7 | 5 | 9 | 9 | | | 9 | 0 |
| 7 | 7 | 9 | 0 | | 9 | 9 | | 9 |
| 9 | 86 | 5 | 9 | 9 | 9 | | 9 | 5 |
| 10 | 7 | | 9 | | 9 | 0 | | 0 |
| 12 | 7 | 0 | 0 | | 9 | 9 | 9 | 0 |
| 13 | 7 | 0 | 9 | | 0 | | | |
| 14 | 7 | | 9 | | | 9 | | |
| 15 | 7 | | 9 | | | 9 | | |
| 16 | 7 | | 9 | | | 9 | | |
| | (Z isomer) | | | | | | | |
| 16 | 7 | | 5 | | | 9 | | |
| | (E isomer) | | | | | | | |
| 17 | 7 | | 9 | | | 0 | | |
| 19 | 7 | | 5 | | | 9 | | |
| 19 | 7 | | 9 | | | 9 | | |
| 20 | 7 | 0 | 5 | 0 | 9 | 9 | 0 | 0 |
| 22 | 7 | | 0 | | | 9 | | |
| 28 | 7 | 0 | 5 | 9 | | | 0 | 0 |
| 30 | 7 | | 9 | | | | | |
| 39 | 86 | 0 | 5 | 9 | 9 | | 9 | |
| 39 | 87 | 0 | 0 | 9 | 9 | | 9 | 0 |
| 39 | 156 | 0 | 9 | 9 | 9 | | | |
| 39 | 157 | 0 | 9 | 9 | 9 | | 9 | |
| 40 | 87 | 0 | 0 | 0 | 0 | | 5 | 0 |
| 42 | 7 | 9 | 9 | 9 | 5 | | 9 | 0 |
| 42 | 87 | 9 | 9 | 9 | 9 | | 9 | 0 |

TABLE 104-continued

| Table Number | Compound Number | Dm | Mp | Hv | Px | Tu | Db | Mi |
|---|---|---|---|---|---|---|---|---|
| 81 | 77 | 0 | 0 | 0 | 0 | 0 | 9 | 0 |
| 82 | 77 | 0 | 9 | 0 | 0 |   |   | 0 |

EXAMPLE 18

This Example illustrates the fungicidal properties of compounds of formula (I). The compounds were tested against a variety of foliar fungal diseases of plants. The technique employed as as follows.

Plants were grown in John Innes Potting Compost (No.1 or 2) in 4 cm diameter, 3.5 cm depth minipots. The test compounds were individually formulated as a solution either in acetone or acetone/ethanol (1:1 by volume) which was diluted in deionised water to a concentration of 100 ppm (that is, 1 mg of compound in a final volume of 10 ml) immediately before use. When foliar sprays were applied to monocotyledonous crops, TWEEN 20 (0.1% by volume) was added TWEEN is a registered trade mark.

Individual compounds of formula (I) were applied as a foliar (Folr) application (where the chemical solution was applied to the foliage of the test plants by spraying the plant to maximum droplet retention.)

These tests were carried out against *Uncinula necator* (UNCINE), on vines; *Venturia inaequalis* (VENTIN) on apples; *Phytophthora infestans lycopersici* (PHYTIN) on tomatoes; *Puccinia recondita* (PUCCRT), on wheat; and *Pyricularia oryzae* (PYRIOR) on rice. Each treatment was applied to two or more replicate plants for *Phytophthora infestans lycopersici* and *Uncinula necator*. For tests on *Puccinia recondita* and *Pyricularia oryzae* two replicate pots each containing 6 to 10 plants were used for each treatment. The plants were inoculated one day before (Erad) or one day after (Prot) chemical application. The *Phytophthora infestans lycopersici, Puccinia recondita* and *Pyricularia oryzae* plants were inoculated with a calibrated fungal spore suspension. The *Uncinula necator* plants were inoculated using a 'blowing' inoculation technique.

After chemical application and inoculation, the plants were incubated under high humidity conditions and then put into an appropriate environment to allow infection to proceed, until the disease was ready for assessment. The time period between chemical application and assessment varied from five to fourteen days according to the disease and environment However, each individual disease was assessed after the same time period for all compounds.

Assessments were performed on each of two leaves on each of the replicate plants for *Phytophthora infestans lycopersici*. Assessments were performed on a single leaf of each of the replicate plants for *Uncinula necator*. For *Puccinia recondita* and *Pyricularia recondita* assessments were carried out collectively on the plants in each replicate pot.

The disease level present (that is, the percentage leaf area covered by actively sporulating disease) was assessed visually. For each treatment, the assessed values for all its replicates were meaned to provide mean disease values. Untreated control plants were assessed in the same manner. The data were then processed by the method, described hereinafter, to provide PRCO (Percentage Reduction from Control) values.

An example of a typical calculation is as follows:

Mean disease level for treatment A=25%

Mean disease level on untreated controls=85%

$$PRCO = 100 - \frac{\{\text{Mean disease level for treatment } A\}}{\{\text{Mean disease level on untreated controls}\}} \times 100$$
$$= 100 - \left(\frac{25}{85} \times 100\right) = 70.6$$

The PRCO is then rounded to the nearest whole number, therefore, in this particular example, the PRCO result is 71. It is possible for negative PRCO values to be obtained. Results are displayed in Table 105.

TABLE 105

| TABLE NO. | COMPOUND NO. | UNCINE Erad | PYRIOR Prot | PUCCRT Prot | PHYTIN Prot | UNCINE Prot | VENTIN Prot |
|---|---|---|---|---|---|---|---|
| 1 | 7 | 100 | 24 | 85 |   |   |   |
| 3 | 7 | 91 |   | 19 | 20 |   |   |
| 4 | 7 | 14 | 0 | 8 | 68 | 61 |   |
| 14 | 7 | 100 | 92 | 98 | 0 |   | 85 |
| 11 | 7 |   | 66 | 27 | 50 | 73 |   |
| 16 | 7 (Z-isomer) | 100 | 70 | 99 |   |   |   |
| 16 | 7 (E-isomer) | 100 | 80 | 100 |   |   | 79 |
| 15 | 7 | 100 | 57 | 100 |   |   | 53 |

Key to Table 105:
VENTIN = *Venturia inaequalis*
PHYTIN = *Phytophthora infestans lycopersici*
PUCCRT = *Puccinia recondita*
PYRIOR = *Pyricularia oryzae*
UNCINE = *Uncinula necator*

EXAMPLE 19

This Example illustrates the fungicidal properties of compounds of formula (I). The compounds were tested against a variety of foliar fungal diseases of plants. The techniques employed were as follows.

Plants were grown either in John Innes Potting Compost (No.1 or 2) in 4 cm diameter, 3.5 cm depth minipots or on an artificial, cellulose based growing medium. The test compounds were individually formulated as a solution either in acetone or acetone/ethanol (1:1 by volume) which was diluted in reverse osmosis water to a concentration of 100 ppm (that is, 1 mg of compound in a final volume of 10 ml) immediately before use. When foliar sprays were applied to monocotyledonous crops, TWEEN 20 (0.1% by volume) was added. TWEEN is a registered trade mark.

Individual compounds of formula (I) were applied as a foliar (Prot) application (where the chemical solution was applied to the foliage of the test plants by spraying the foliage to maximum droplet retention) or as a systemic (Syst) application (where the chemical was added to a small beaker in which the test plant pots were standing).

These tests were carried out against *Plasmopara viticola* (PLASVI) on vines; *Phytophthora infestans lycopersici* (PHYTIN) on tomatoes; and *Blumeria graminis* f.sp. *tritici* (ERYSGT), *Stagonospora nodorum* (LEPTNO) and *Puccinia thricina* (PUCCRT) on wheat. Each treatment was applied to two or more replicate plants for *Plasmopara viticola* and *Phytophthora infestans tycopersici* and in all tests where the cellulose growing medium was employed. In minipot tests on *Blumeria graminis* f.sp. *tritici, Stagonospora nodorum* and *Puccinia triticina*, two replicate pots each containing 6 to 10 plants were used for each treatment The plants were inoculated with a calibrated fungal spore either 6 hours or one day after chemical application.

After chemical application and inoculation, the plants were incubated under high humidity conditions and then put into an appropriate environment to allow infection to proceed, until the disease was ready for assessment. The *Blumeria graminis* f.sp. *tritici* plants were inoculated using a 'shake' inoculation technique. For *Plasmopara viticola*, the plants were reincubated under high humidity conditions for 24 hours prior to assessment. The time period between chemical application and assessment varied from five to nine days according to the disease and environment. However, each individual disease was assessed after the same time period for all the compounds tested against that particular disease.

Assessments were performed on a single leaf of each of the two replicate plants for *Piasmopara viticola* and on each of two leaves on each of the replicate plants for *Phytophthora infestans lycopersici*. For *Blumeria graminis* f.sp. *tritici, Stagonospora nodorum* and *Puccinia triticina*, assessments were carried out collectively on the plants in each replicate minipot or cellulose medium.

The disease level present (that is, the percentage leaf area covered by actively sporulating disease) was assessed visually. For each treatment, the assessed values for all its replicates were meaned to provide mean disease values. Untreated control plants were assessed in the same manner. The data were then processed by either of two alternative methods, described below, each providing its own PRCO (Percentage Reduction from Control) value. All assessments on plants grown on cellulose media (and some grown in soil) used method 1.

METHOD 1

This method uses banded assessment values.

The mean disease values are banded in the manner shown below. If the disease level value falls exactly mid-way between two of the points, the result will be the lower of the two points.

| 0 = | 0% disease present | 10 = | 5.1–10% disease present |
| 1 = | 0.1–1% disease present | 20 = | 10.1–20% disease present |
| 3 = | 1.1–3% disease present | 30 = | 20.1–30% disease present |
| 5 = | 3.1–5% disease present | 60 = | 30.1–60% disease present |
| | | 90 = | 60.1–100% disease present |

An example of a typical banded calculation is as follows:
Mean disease level for treatment A=25%
Therefore banded mean disease level for treatment A=30
Mean disease level on untreated controls=85%
Therefore banded mean disease level on untreated controls=90

$$PRCO = 100 - \frac{\{\text{Banded Mean disease level for treatment } A\}}{\{\text{Mean disease level on untreated controls}\}} \times 100$$

$$= 100 - \left(\frac{30}{90} \times 100\right) = 66.7$$

The PRCO is then rounded to the nearest whole number, therefore, in this particular example, the PRCO result is 67.

METHOD 2

This method uses unbanded assessment values (that is, the mean disease values are used in the PRCO calculation without a banding step).

An example of a typical unbanded calculation is as follows:
Mean disease level for treatment A=25%
Mean disease level on untreated controls=85%

$$PRCO = 100 - \frac{\{\text{Mean disease level for treatment } A\}}{\{\text{Mean disease level on untreated controls}\}} \times 100$$

$$= 100 - \left(\frac{25}{85} \times 100\right) = 70.6$$

The PRCO is then rounded to the nearest whole number; therefore, in this particular example, the PRCO result is 71.
It is possible for negative PRCO values to be obtained.
Results are displayed in Table 106.

TABLE 106

| TABLE NO. | COMPOUND NO. | PLASVI Prot | ERYSGT Prot | PUCCRT Prot | PHYTIN Prot |
|---|---|---|---|---|---|
| 14 | 7 | | 83 | | |
| 5 | 7 | 98 | 100 | 96 | |
| 20 | 7 | 100 | | | 72 |
| 12 | 7 | 100 | 78 | 97 | |
| 30 | 7 | | 100 | | |
| 28 | 7 | 97 | 98 | | |
| 13 | 7 | 100 | | | 100 |

Key to Table 106:
ERYSGT = *Blumeria graminis* f.sp. *tritici*
PLASVI = *Plasmopara viticola*
PHYTIN = *Phytophthora infestans lycopersici*
PUCCRT = *Puccinia recondita*

We claim:
1. A compound of formula (I):

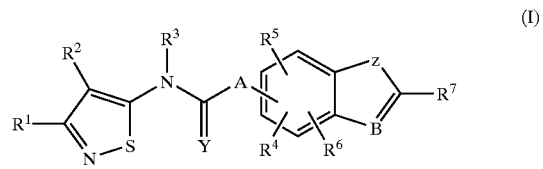

where A is optionally substituted $C_{1-6}$ alkylene, optionally substituted $C_{2-6}$ alkenylene, optionally substituted $C_{2-6}$ alkynylene, optionally substituted cyoalkylene, optionally substituted $C_{1-6}$ alkylenoxy, optionally substituted oxy($C_{1-6}$)alkylene, optionally substituted $C_{1-6}$ alkylenethio, optionally substituted thio($C_{1-6}$)alkylene, optionally substituted $C_{1-6}$ alkylenamino, optionally substituted amino($C_{1-6}$) alkylene, optionally substituted [$C_{1-6}$ alkyleneoxy($C_{1-6}$) alkylene], optionally substituted [$C_{1-6}$ alkylenethio($C_{1-6}$)

alkylene], optionally substituted [$C_{1-6}$ alkylenesulfinyl ($C_{1-6}$)alkyene], optionally substituted [$C_{1-6}$ alkylenesulfonyl ($C_{1-6}$)alkylene] or optionally substituted [$C_{1-6}$ alkyleneamino($C_{1-6}$)alkylene]; provided that A is not $CH_2$ or $CH_2O$; B is N,N-oxide or $CR^8$; Y is O, S or $NR^9$; Z is O, S or $NR^{10}$; $R^1$ is hydrogen, halogen, optionally substituted $C_{1-6}$ alkyl; optionally substituted $C_{2-6}$ alkenyl, optionally substituted $C_{2-6}$ alkynyl, optionally substituted $C_{1-6}$ alkoxy, optionally substituted $C_{1-6}$ alkylthio, optionally substituted $C_{3-7}$ cycoalkyl, cyano, nitro or $SF_5$; $R^2$ is hydrogen, halogen, optionally substituted $C_{1-6}$ alkyl, optionally substituted $C_{2-6}$ alkenyl, optionally substituted $C_{2-6}$ alkynyl, optionally substituted $C_{1-6}$ alkoxy, optionally substituted $C_{1-6}$ alkylthio, optionally substituted $C_{1-6}$ alkylsulfinyl, optionally substituted $C_{1-6}$ alkylsulfonyl, cyano, nitro, formyl, optionally substituted $C_{1-6}$ alkylcarbonyl, optionally substituted $C_{1-6}$ alkoxycarbonyl, $SF_5$ or $R^{11}ON=C(R^{12})$; or $R^1$ and $R^2$ together with the atoms to which they are attached may be joined to form a five, six or seven-membered saturated or unsaturated, carbocyclic or heterocyclic ring which may contain one or two heteroatoms selected from O, N or S and which is optionally substituted by $C_{1-6}$ alkyl, $C_{1-6}$ haloalkyl or halogen; $R^3$ is hydrogen, optionally substituted $C_{1-10}$ alkyl, optionally substituted $C_{2-6}$ alkenyl($C_{1-6}$)alkyl], optionally substituted [$C_{2-6}$ alkynyl($C_{1-6}$)alkyl], optionally substituted $C_{3-7}$ cycloalkyl, optionally substituted $C_{1-10}$ alkylcarbonyl, optionally substituted $C_{1-10}$ alkoxycarbonyl, formyl, optionally substituted $C_{1-10}$ alkylaminocarbonyl, optionally substituted di($C_{1-10}$)alkylaminocarbonyl, optionally substituted phenoxycarbonyl, optionally substituted $C_{1-6}$ alkylthio, optionally substituted $C_{1-6}$ alkylsulfinyl, optionally substituted $C_{1-6}$ alkylsulfonyl, optionally substituted $C_{1-6}$ arylthio, optionally substituted $C_{1-6}$ arylsulfinyl, optionally substituted $C_{1-8}$ arylsulfonyl or $R^{13}R^{14}NS(O)_p$; p is 0, 1 or 2; $R^4$, $R^5$ and $R^6$ are, independently, hydrogen, halogen, optionally substituted $C_{1-6}$ alkyl, optionally substituted $C_{1-6}$ alkoxy, optionally substituted $C_{1-6}$ alkylthio, optionally substituted $C_{1-6}$ alkylsulfinyl, optionally substituted $C_{1-6}$ alkylsulfonyl, cyano, nitro, optionally substituted $C_{1-6}$ alkylcarbonyl, optionally substituted $C_{1-6}$ alkoxycarbonyl or $SF_5$; $R^7$ is hydrogen, halogen, cyano, optionally substituted $C_{1-20}$ alkyl, optionally substituted $C_{2-20}$ alkenyl, optionally substituted $C_{2-20}$ alkynyl, optionally substituted $C_{3-7}$ cycloalkyl, optionally substituted $C_{5-6}$ cycloalkenyl, formyl, optionally substituted $C_{1-20}$ alkoxycarbonyl, optionally substituted $C_{1-20}$ alkylcarbonyl, aminocarbonyl, optionally substituted $C_{1-20}$ alkylaminocarbonyl, optionally substituted di($C_{120}$)alkylaminocarbonyl, optionally substituted aryloxycarbonyl, optionally substituted arylcarbonyl, optionally substituted arylaminocarbonyl, optionally substituted N—($C_{1-6}$)alkyl-N-arylaminocarbonyl, optionally substituted diarylaminocarbonyl, optionally substituted heteroaryloxycarbonyl, optionally substituted heteroarylcarbonyl, optionally substituted heteroarylaminocarbonyl, optionally substituted N—($C_{1-6}$)alkyl-N-heteroarylaminocarbonyl, optionally substituted diheteroarylaminocarbonyl, optionally substituted phenyl, optionally substituted heteroaryl, optionally substituted heterocyclyl, SH, optionally substituted $C_{1-20}$ alkylthio, optionally substituted $C_{1-20}$ alkylsulfinyl, optionally substituted $C_{1-20}$ alkylsulfonyl, optionally substituted arylthio, optionally substituted arylsulfinyl, optionally substituted arylsulfonyl, $R^{15}O$, $R^{16}R^{17}N$ or $R^{18}ON=C(R^{19})$; $R^8$ is hydrogen, halogen, nitro, cyano, optionally substituted $C_{1-8}$ alkyl, optionally substituted $C_{2-6}$ alkenyl, optionally substituted $C_{2-6}$ alkynyl, optionally substituted $C_{3-7}$ cycloalkyl, optionally substituted $C_{1-6}$ alkoxycarbonyl, optionally substituted $C_{1-6}$ alkylcarbonyl, optionally substituted $C_{1-6}$ alkylaminocarbonyl, optionally substituted di($C_{1-6}$) alkylaminocarbonyl, optionally substituted phenyl or optionally substituted heteroaryl; $R^9$ is hydrogen, cyano, nitro, optionally substituted $C_{1-6}$ alkyl, optionally substituted $C_{3-7}$ cycloalkyl, optionally substituted ($C_{2-6}$)alkenyl ($C_{1-6}$)alkyl, optionally substituted ($C_{2-6}$)alkynyl($C_{1-6}$)alkyl, optionally substituted phenyl, optionally substituted heteroaryl, optionally substituted $C_{1-6}$ alkylcarbonyl, optionally substituted $C_{1-6}$ alkoxycarbonyl, optionally substituted $C_{1-6}$ alkylamino, optionally substituted di($C_{1-6}$) alkylamino, optionally substituted $C_{1-8}$ alkylcarbonylamino, optionally substituted $C_{1-6}$ alkoxycarbonylamino, optionally substituted $C_{1-6}$alkoxy, optionally substituted $C_{1-6}$ alkylthio, optionally substituted $C_{1-8}$ alkylsulfinyl, optionally substituted $C_{1-8}$ alkylsulfonyl, optionally substituted arylthio, optionally substituted arylsulfinyl, optionally substituted arylsulfonyl or $C_{1-6}$ alkylcarbonyloxy; $R^{10}$ is hydrogen, cyano, optionally substituted $C_{1-8}$ alkyl, optionally substituted [$C_{2-6}$ alkenyl($C_{1-6}$)alkyl], optionally substituted [$C_{2-6}$ alkynyl($C_{1-6}$)alkyl], optionally substituted $C_{3-7}$ cycloalkyl, optionally substituted ($C_{3-7}$ cycloalkyl($C_{1-6}$)alkyl], $C_{1-6}$ alkoxy($C_{1-6}$)alkyl, optionally substituted $C_{1-6}$ alkoxycarbonyl, optionally substituted $C_{1-6}$ alkylcarbonyl, optionally substituted $C_{1-6}$ alkylaminocarbonyl, optionally substituted di($C_{1-6}$)alkylaminocarbonyl, optionally substituted phenyl, optionally substituted heteroaryl, optionally substituted alkylsulfonyl or optionally substituted arylsulfonyl; $R^{11}$ and $R^{12}$ are, independently, hydrogen, optionally substituted phenyl ($C_{1-2}$)alkyl or optionally substituted $C_{1-20}$ alkyl; $R^{12}$ and $R^{19}$ are, independently, hydrogen, optionally substituted phenyl or optionally substituted $C_{1-6}$ alkyl; $R^{13}$ and $R^{14}$ are, independently, optionally substituted $C_{1-6}$ alkyl; or $R^{13}$ and $R^{14}$ together with the N atom to which they are attached form a five, six or seven-membered heterocyclic ring which may contain one or two further heteroatoms selected from O, N and S and which is optionally substituted by one or two independently selected $C_{1-6}$ alkyl groups; $R^{15}$ is hydrogen, optionally substituted $C_{1-20}$ alkyl, optionally substituted [$C_{2-20}$ alkenyl($C_{1-6}$)alkyl], optionally substituted [$C_{2-20}$ alkynyl($C_{1-6}$)alkyl], optionally substituted $C_{3-7}$ cycloalkyl, optionally substituted aryl, optionally substituted heteroaryl, optionally substituted heterocyclyl, ($C_{1-6}$) alkylCH=N, optionally substituted arylCH=N, optionally substituted [aryl($C_{1-6}$)alkyl]CH=N, optionally substituted heteroarylCH=N, optionally substituted [heterocyclyl ($C_{1-6}$)alkyl]CH=N, optionally substituted arylC(CH$_3$)N, optionally substituted heteroarylC(CH$_3$)=N or optionally substituted di($C_{1-6}$)alkylC=N; and $R^{16}$ and $R^{17}$ are, independently, hydrogen, optionally substituted $C_{1-20}$ alkyl, optionally substituted $C_{3-7}$ cycloalkyl, optionally substituted [$C_{2-20}$ alkenyl($C_{1-6}$)alkyl], optionally substituted [$C_{2-20}$ alkynyl($C_{1-6}$)alkyl], optionally substituted $C_{1-20}$ alkoxycarbonyl, optionally substituted phenoxycarbonyl, formyl, optionally substituted $C_{1-20}$ alkylcarbonyl, optionally substituted $C_{1-20}$ alkylsulfonyl or optionally substituted phenylsulfonyl.

2. A compound of formula (I) according to claim 1 which is a compound of formula (IA):

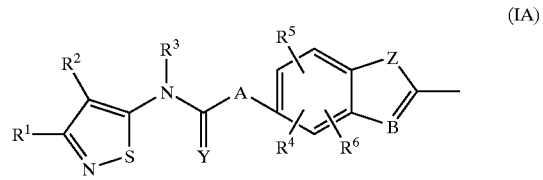

(IA)

wherein A, B, Y, Z, $R^1$, $R^2$, $R^3$, $R^4$, $R^5$, $R^6$ and $R^7$ are as claimed in claim 1.

3. A compound of formula (I) as claimed in claim 1 where A is $C_{1-6}$ alkylene, $C_{1-6}$ alkenylene. $C_{1-6}$ alkylenoxy, oxy($C_{1-6}$)alkylene or $C_{1-6}$ alkylenamino, each of which is optionally substituted by $C_{1-3}$ alkyl, $C_{1-3}$ haloalkyl, $C_{1-3}$ cyanoalkyl, halogen, $C_{1-3}$ alkoxy, $C_{1-6}$ alkoxycarbonyl, cyano, =O, =NR$^{20}$ or =CR$^{21}$R$^{22}$; where R$^{20}$ is $C_{1-6}$ alkyl, OR$^{23}$ or NR$^{24}$R$^{25}$; R$^{23}$ is $C_{1-6}$ alkyl or phenyl($C_{1-2}$)alkyl (where the phenyl group is optionally substituted by halo, nitro, cyano, $C_{1-6}$ alkyl, $C_{1-8}$ haloalkyl, $C_{1-6}$ alkoxy or $C_{1-6}$ haloalkoxy); R$^{24}$ and R$^{25}$ are, independently, hydrogen, $C_{1-8}$ alkyl or phenyl (which may be optionally substituted by halo, nitro, cyano, $C_{1-6}$ alkyl, $C_{1-6}$ haloalkyl, $C_{1-6}$ alkoxy or $C_{1-6}$ haloalkoxy); R$^{21}$ is hydrogen, $C_{1-6}$ alkyl or $C_{1-6}$ haloalkyl; R$^{22}$ is hydrogen, $C_{1-6}$ alkyl, $C_{1-6}$ haloalkyl, $C_{1-6}$ alkoxy, cyano, $C_{1-6}$ alkoxycarbonyl, $C_{1-6}$ alkylcarbonyl or NR$^{26}$R$^{27}$; and R$^{26}$ and R$^{27}$ are, independently, hydrogen, $C_{1-8}$ alkyl, $C_{3-7}$ cycloalkyl, $C_{3-6}$ alkenyl, $C_{3-6}$ alkynyl, $C_{2-6}$ haloalkyl, $C_{1-6}$ alkoxy($C_{1-6}$)alkyl, $C_{1-6}$ alkoxycarbonyl($C_{1-6}$)alkyl, carboxy($C_{1-6}$)alkyl or phenyl($C_{1-2}$)alkyl; or R$^{26}$ and R$^{27}$ together with the N atom to which they are attached form a five, six or seven-membered heterocyclic ring which may contain one or two further heteroatoms selected from O, N or S and which may be optionally substituted by one or two $C_{1-6}$ alkyl groups; provided that A is not CH$_2$ or CH$_2$O.

4. A compound of formula (I) as claimed in claim 1 where Y is O or S.

5. A compound of formula (I) as claimed in claim 1 where R$^1$ is hydrogen, halogen, $C_{1-6}$ alkyl, $C_{1-6}$ cyanoalkyl, haloalkyl, $C_{3-7}$ cycloalkyl($C_{1-4}$)alkyl, $C_{1-6}$ alkoxy($C_{1-6}$)alkyl, $C_{2-6}$ alkenyl, $C_{2-6}$ alkynyl, $C_{1-6}$ alkoxy, $C_{1-6}$ haloalkoxy, $C_{1-6}$ alkylthio, $C_{1-6}$ haloalkylthio, $C_{3-6}$ cycloalkyl, cyano, nitro or SF$_5$.

6. A compound of formula (I) as claimed in claim 1 where R$^2$ is hydrogen, halogen, $C_{1-6}$ alkyl, $C_{1-6}$ haloalkyl, $C_{1-6}$ alkoxy($C_{1-8}$)alkyl, $C_{2-6}$ alkenyl, $C_{1-6}$ alkynyl, $C_{1-8}$ alkoxy, $C_{1-6}$ haloalkoxy, $C_{1-6}$ alkylthio, $C_{1-6}$ haloalkylthio, $C_{1-6}$ alkylsulfinyl, $C_{1-6}$ haloalkylsulfinyl, $C_{1-6}$ alkylsulfonyl, $C_{1-6}$ haloalkylsulfonyl, cyano, nitro, formyl, $C_{1-6}$ alkylcarbonyl, $C_{1-6}$ alkoxycarbonyl or CH=NOR$^{11}$; or R$^1$ and R$^2$ together with the atoms to which they are attached may be joined to form a five, six or seven-membered saturated or unsaturated, carbocyclic or heterocyclic ring which may contain one or two heteroatoms selected from O, N or S and which is optionally substituted by $C_{1-6}$ alkyl, $C_{1-6}$ haloalkyl or halogen; where R$^{11}$ is phenyl($C_{1-2}$)alkyl (wherein the phenyl group is optionally substituted by halo, nitro, cyano, $C_{1-6}$ alkyl, $C_{1-6}$ haloalkyl, $C_{1-6}$ alkoxy or $C_{1-6}$ haloalkoxy) or $C_{1-6}$ alkyl.

7. A compound of formula (I) as claimed in claim 1 where R$^3$ is hydrogen, $C_{1-10}$ alkyl, $C_{1-6}$ alkylcarbonyloxy($C_{1-6}$)alkyl, benzoyloxymethyl (where the phenyl ring is optionally substituted with halogen or $C_{1-4}$ alkyl), $C_{1-6}$ alkoxy($C_{1-6}$)alkyl (where the alkyl group is optionally substituted by aryl or $C_{1-4}$ alkoxycarbonyl), $C_{2-6}$ alkenyloxy($C_{1-4}$)alkyl, $C_{2-6}$ alkynyloxy($C_{1-4}$)alkyl, benzyloxy($C_{1-4}$)alkyl (where the phenyl ring is optionally substituted with halogen or $C_{1-4}$ alkyl), $C_{3-7}$ cycloalkyl-($C_{1-4}$)alkyl, heteroaryl($C_{1-3}$)alkyl (where the heteroaryl group is optionally substituted with halogen), tri($C_{1-4}$)alkylsilyl($C_{1-6}$)alkyl, $C_{2-6}$ alkenyl($C_{1-6}$)alkyl (especially allyl), $C_{2-6}$ haloalkenyl($C_{1-6}$)alkyl, $C_{1-4}$ alkoxycarbonyl($C_{2-6}$)alkenyl-($C_{1-8}$)alkyl, $C_{2-6}$ alkynyl($C_{1-6}$)alkyl, tri($C_{1-4}$)alkylsilyl($C_{2-6}$)alkynyl($C_{1-6}$)alkyl or $C_{1-10}$ alkylcarbonyl.

8. A compound of formula (I) as claimed in claim 1 where R$^4$, R$^5$ and R$^6$ are, independently, hydrogen, halogen, $C_{1-6}$ alkyl, $C_{1-6}$ haloalkyl, $C_{1-8}$ alkoxy, $C_{1-6}$ haloalkoxy, $C_{1-6}$ alkylthio, $C_{1-6}$ haloalkylthio, $C_{1-6}$ alkylsulfinyl, $C_{1-6}$ haloalkylsulfinyl, $C_{1-6}$ alkylsulfonyl, $C_{1-6}$ haloalkylsulfonyl, cyano, nitro, $C_{1-6}$ alkylcarbonyl or $C_{1-6}$ alkoxycarbonyl.

9. A compound of formula (I) as claimed in claim 1 where R$^7$ is cyano, $C_{1-8}$ alkyl, $C_{1-6}$ haloalkyl, $C_{1-8}$ cyanoalkyl, $C_{3-7}$ cycloalkyl($C_{1-6}$)alkyl, $C_{5-6}$ cycloalkenyl-($C_{1-6}$)alkyl, $C_{1-6}$ alkoxy($C_{1-6}$)alkyl, $C_{3-6}$ alkenyloxy($C_{1-6}$)alkyl, $C_{3-6}$ alkynyloxy-($C_{1-6}$)alkyl, aryloxy($C_{1-6}$)alkyl, $C_{1-6}$ carboxyalkyl, $C_{1-6}$ alkylcarbonyl($C_{1-6}$)alkyl, $C_{2-6}$ alkenylcarbonyl($C_{1-6}$)alkyl, $C_{2-6}$ alkynylcarbonyl($C_{1-6}$)alkyl, $C_{1-6}$ alkoxycarbonyl-($C_{1-6}$)alkyl, $C_{3-6}$ alkenyloxycarbonyl($C_{1-6}$)alkyl, $C_{3-6}$ alkynyloxycarbonyl($C_{1-6}$)alkyl, aryloxycarbonyl($C_{1-6}$)alkyl, $C_{1-6}$ alkylthio($C_{1-6}$)alkyl, $C_{1-6}$ alkylsulfinyl($C_{1-6}$)alkyl, $C_{1-6}$ alkylsulfonyl($C_{1-6}$)alkyl, aminocarbonyl($C_{1-6}$)alkyl, $C_{1-6}$ alkylaminocarbonyl-($C_{1-8}$)alkyl, di($C_{1-6}$) alkylaminocarbonyl($C_{1-6}$)alkyl, phenyl($C_{1-4}$)alkyl (wherein the phenyl group is optionally substituted by halo, nitro, cyano, $C_{1-6}$ alkyl, $C_{1-6}$ haloalkyl, $C_{1-6}$ alkoxy or $C_{1-6}$ haloalkoxy), heteroaryl($C_{1-4}$)alkyl (where the heteroaryl group is optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyl($C_{1-4}$)alkyl (where the heterocyclyl group is optionally substituted by halo, cyano, $C_{1-6}$ alkyl, $C_{1-6}$ haloalkyl, $C_{1-6}$ alkoxy or $C_{1-6}$ haloalkoxy), $C_{2-6}$ alkenyl, $C_{2-6}$ haloalkenyl, $C_{1-6}$ cyanoalkenyl, $C_{5-6}$ cycloalkenyl, aminocarbonyl-($C_{2-6}$)alkenyl, $C_{1-6}$ alkylaminocarbonyl ($C_{1-6}$)alkenyl, di($C_{1-6}$)alkylaminocarbonyl-($C_{1-6}$)alkenyl, phenyl($C_{2-4}$)alkenyl (wherein the phenyl group is optionally substituted by halo, nitro, cyano, $C_{1-6}$ alkyl, $C_{1-6}$ haloalkyl, $C_{1-6}$ alkoxy or $C_{1-6}$ haloalkoxy), $C_{2-6}$ alkynyl, aminocarbonyl($C_{2-6}$)alkynyl, alkylaminocarbonyl($C_{1-6}$) alkynyl, di($C_{1-6}$) alkylaminocarbonyl($C_{1-6}$)alkynyl, $C_{3-7}$ cycloalkyl, $C_{3-7}$ halocycloalkyl, $C_{3-7}$ cyanocycloalkyl, $C_{1-3}$ alkyl($C_{3-7}$)cycloalkyl, $C_{1-3}$ alkyl($C_{3-7}$)halocycloalkyl, $C_{5-6}$ cycloalkenyl, formyl, $C_{1-6}$ alkoxycarbonyl, $C_{1-6}$ alkylcarbonyl, aminocarbonyl, $C_{1-6}$ alkylaminocarbonyl, di($C_{1-6}$)alkylaminocarbonyl, phenyl (optionally substituted by halo, nitro, cyano, $C_{1-6}$ alkyl, $C_{1-6}$ haloalkyl, $C_{1-6}$ alkoxy or $C_{1-6}$ haloalkoxy), heteroaryl (optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyl (optionally substituted by halo, nitro, cyano, $C_{1-6}$ alkyl, $C_{1-6}$ haloalkyl, $C_{1-6}$ alkoxy or $C_{1-6}$ haloalkoxy), $C_{1-6}$ alkylthio, R$^{15}$O, R$^{16}$R$^{17}$N or R$^{18}$ON=C(R$^{19}$); where R$^{15}$ is hydrogen, $C_{1-6}$ alkyl, $C_{1-6}$ haloalkyl, $C_{1-6}$ cyanoalkyl, $C_{1-6}$ alkoxy($C_{1-6}$)alkyl, phenyl ($C_{1-4}$)alkyl, (wherein the phenyl group is optionally substituted by halo, nitro, cyano, $C_{1-6}$ alkyl, $C_{1-6}$ haloalkyl, $C_{1-6}$ alkoxy or $C_{1-6}$ haloalkoxy), heteroaryl($C_{1-4}$)alkyl (wherein the heteroaryl group is optionally substituted by halo, nitro, cyano, $C_{1-6}$ alkyl, $C_{1-6}$ haloalkyl, $C_{1-6}$ alkoxy or $C_{1-6}$ haloalkoxy), heterocyclyl($C_{1-4}$)alkyl (wherein the heterocyclyl group is optionally substituted by halo, nitro, cyano, $C_{1-6}$ alkyl, $C_{1-6}$ haloalkyl, $C_{1-6}$ alkoxy or $C_{1-6}$ haloalkoxy), $C_{1-6}$ alkoxycarbonyl($C_{1-6}$)alkyl, $C_{2-6}$ alkenyl, $C_{2-6}$ alkynyl or N=C(CH$_3$)$_2$; R$^{19}$ is phenyl (optionally substituted by halo, nitro, cyano, $C_{1-6}$ alkyl, $C_{1-6}$ haloalkyl, $C_{1-6}$ alkoxy or $C_{1-6}$ haloalkoxy), $C_{1-6}$ alkyl or $C_{1-6}$ haloalkyl; R$^{16}$ and R$^{17}$ are, independently, hydrogen, $C_{1-6}$ alkyl, $C_{3-7}$cyoalkyl ($C_{1-4}$)alkyl, $C_{2-6}$ haloalkyl, $C_{1-6}$ alkoxy($C_{1-6}$)alkyl, $C_{3-7}$ cycloalkyl, $C_{3-6}$ alkenyl, $C_{3-6}$ alkynyl or $C_{1-6}$ alkoxycarbonyl; and R$^{18}$ is phenyl($C_{1-2}$)alkyl (wherein the phenyl group is optionally substituted by halo, nitro, cyano, $C_{1-6}$ alkyl, $C_{1-6}$ haloalkyl, $C_{1-6}$ alkoxy or $C_{1-6}$ haloalkoxy) or $C_{1-6}$ alkyl.

10. A fungicidal, insecticidal, acaricidal, molluscicidal or nematicidal composition comprising a fungicidally, insecticidally, acaricidally, molluscicidally or nematicidally effective amount of a compound of formula (I) as claimed in claim 1 and a carrier or diluent therefor.

11. A method of combating and controlling fungi comprising applying to a plant, to a seed of a plant, to the locus of the plant or seed or to the soil a fungicidally effective amount of a composition as claimed in claim 10.

12. A method of combating and controlling insects, acarines, nematodes or molluscs which comprises applying to a pest, to a locus of a pest, or to a plant susceptible to attack by a pest an insecticidally, acaricidally, nematicidally or molluscicidally effective amount of a composition as claimed in claim 10.

* * * * *